United States Patent
Fabian, Jr.

(10) Patent No.: US 11,883,303 B2
(45) Date of Patent: Jan. 30, 2024

(54) SPINE SURGERY METHOD AND INSTRUMENTATION

(71) Applicant: VERTEBRATION, INC., Powell, OH (US)

(72) Inventor: Henry F. Fabian, Jr., Steamboat Springs, CO (US)

(73) Assignee: VERTEBRATION, INC., Powell, OH (US)

( * ) Notice: Subject to any disclaimer, the term of this patent is extended or adjusted under 35 U.S.C. 154(b) by 303 days.

(21) Appl. No.: 17/138,176

(22) Filed: Dec. 30, 2020

(65) Prior Publication Data

US 2021/0196480 A1 Jul. 1, 2021

Related U.S. Application Data

(60) Provisional application No. 62/954,972, filed on Dec. 30, 2019.

(51) Int. Cl.
*A61F 2/44* (2006.01)
*A61F 2/46* (2006.01)

(52) U.S. Cl.
CPC ............ *A61F 2/4611* (2013.01); *A61F 2/442* (2013.01); *A61F 2/4684* (2013.01); *A61F 2002/4622* (2013.01)

(58) Field of Classification Search
CPC ........ A61F 2/445; A61F 2/446; A61F 2/4465; A61F 2/447; A61F 2/4611; A61F 2002/30179; A61F 2002/30545; A61F 2002/30538; A61F 2002/30556
See application file for complete search history.

(56) References Cited

U.S. PATENT DOCUMENTS

| | | |
|---|---|---|
| 2,417,114 A | 3/1947 | Killham |
| 2,907,189 A | 10/1959 | Fleig |
| 3,867,728 A | 2/1975 | Stubstad et al. |
| 4,309,777 A | 1/1982 | Patil |
| 4,349,921 A | 9/1982 | Kuntz |
| 4,401,112 A | 8/1983 | Rezaian |
| 4,501,269 A | 2/1985 | Bagby |
| 4,553,273 A | 11/1985 | Wu |
| 4,643,178 A | 2/1987 | Nastari et al. |
| 4,714,469 A | 12/1987 | Kenna |
| 4,743,256 A | 5/1988 | Brantigan |
| 4,759,769 A | 7/1988 | Hedman et al. |
| 4,772,287 A | 9/1988 | Ray et al. |
| 4,820,305 A | 4/1989 | Harms et al. |
| 4,834,757 A | 5/1989 | Brantigan |

(Continued)

FOREIGN PATENT DOCUMENTS

| | | |
|---|---|---|
| EP | 0773088 A1 | 5/1997 |
| EP | 1506753 B1 | 2/2005 |

(Continued)

OTHER PUBLICATIONS

International Preliminary Examining Authority; IPRP; PCT/US2012/022637; dated Feb. 1, 2013; 6 pages.

*Primary Examiner* — Jan Christopher L Merene
(74) *Attorney, Agent, or Firm* — Timothy D. Bennett; Emerson Thomson Bennett

(57) ABSTRACT

Surgical instrumentation may be used to insert a spinal implant into an intradiscal space while in a non-deployed condition and then deploy the spinal implant within the intradiscal space.

14 Claims, 77 Drawing Sheets

(56) References Cited

U.S. PATENT DOCUMENTS

| | | |
|---|---|---|
| 4,863,477 A | 9/1989 | Monson |
| 4,878,915 A | 11/1989 | Brantigan |
| 4,932,969 A | 6/1990 | Frey et al. |
| 4,932,975 A | 6/1990 | Main et al. |
| 4,946,378 A | 8/1990 | Hirayama et al. |
| 4,961,740 A | 10/1990 | Ray et al. |
| 5,002,576 A | 3/1991 | Fuhrmann et al. |
| 5,015,247 A | 5/1991 | Michelson |
| 5,055,104 A | 10/1991 | Ray |
| 5,071,437 A | 12/1991 | Steffee |
| 5,123,926 A | 6/1992 | Pisharodi |
| 5,156,839 A | 10/1992 | Pennell et al. |
| 5,192,327 A | 3/1993 | Brantigan |
| 5,246,458 A | 9/1993 | Graham |
| 5,314,477 A | 5/1994 | Marnay |
| 5,368,600 A | 11/1994 | Failla et al. |
| 5,397,364 A | 3/1995 | Kozak et al. |
| 5,439,464 A | 8/1995 | Shapiro |
| 5,484,437 A | 1/1996 | Michelson |
| 5,505,732 A | 4/1996 | Michelson |
| 5,571,192 A | 11/1996 | Schonhoffer |
| 5,665,122 A | 9/1997 | Kambin |
| 5,772,661 A | 6/1998 | Michelson |
| 5,782,919 A | 7/1998 | Zdeblick et al. |
| 5,785,647 A | 7/1998 | Tompkins et al. |
| 5,976,187 A | 11/1999 | Richelsoph |
| 6,080,155 A | 6/2000 | Michelson |
| 6,093,205 A | 6/2000 | McLeod et al. |
| 6,093,207 A | 7/2000 | Pisharodi |
| 6,159,211 A | 12/2000 | Boriani et al. |
| 6,159,214 A | 12/2000 | Michelson |
| 6,193,757 B1 | 2/2001 | Foley et al. |
| 6,200,348 B1 | 3/2001 | Biedermann et al. |
| 6,206,922 B1 | 3/2001 | Zdeblick et al. |
| 6,228,022 B1 | 5/2001 | Friesem et al. |
| 6,264,657 B1 | 7/2001 | Urbahns et al. |
| 6,283,966 B1 | 9/2001 | Houfburg |
| 6,332,887 B1 | 12/2001 | Knox |
| 6,395,031 B1 | 5/2002 | Foley et al. |
| 6,395,034 B1 | 5/2002 | Suddaby |
| 6,402,785 B1 | 6/2002 | Zdeblick et al. |
| 6,409,766 B1 | 6/2002 | Brett |
| 6,471,724 B2 | 10/2002 | Zdeblick et al. |
| 6,488,710 B2 | 12/2002 | Besselink |
| 6,514,260 B1 | 2/2003 | Zdeblick et al. |
| 6,524,318 B1 | 2/2003 | Longhini et al. |
| 6,554,836 B2 | 4/2003 | Michelson |
| 6,565,574 B2 | 5/2003 | Michelson |
| 6,575,981 B1 | 6/2003 | Boyd et al. |
| 6,599,292 B1 | 7/2003 | Ray |
| 6,626,943 B2 | 9/2003 | Eberlein et al. |
| 6,648,895 B2 | 11/2003 | Burkus et al. |
| 6,652,533 B2 | 11/2003 | O'Neil |
| 6,695,851 B2 | 2/2004 | Zdeblick et al. |
| 6,695,857 B2 | 2/2004 | Gifford, III et al. |
| 6,706,068 B2 | 3/2004 | Feree |
| 6,709,458 B2 | 3/2004 | Michelson |
| 6,712,818 B1 | 3/2004 | Michelson |
| 6,712,819 B2 | 3/2004 | Zucherman et al. |
| 6,712,825 B2 | 3/2004 | Aebi et al. |
| 6,716,247 B2 | 4/2004 | Michelson |
| 6,719,794 B2 | 4/2004 | Gerber et al. |
| 6,723,096 B1 | 4/2004 | Dorchak et al. |
| 6,723,109 B2 | 4/2004 | Solingen |
| 6,730,127 B2 | 5/2004 | Michelson |
| 6,733,535 B2 | 5/2004 | Michelson |
| 6,740,087 B2 | 5/2004 | Knox |
| 6,743,234 B2 | 6/2004 | Burkus et al. |
| 6,746,484 B1 | 6/2004 | Liu et al. |
| 6,749,636 B2 | 6/2004 | Michelson |
| 6,755,841 B2 | 6/2004 | Fraser et al. |
| 6,758,849 B1 | 7/2004 | Michelson |
| 6,761,723 B2 | 7/2004 | Buttermann et al. |
| 6,767,367 B1 | 7/2004 | Michelson |
| 6,770,074 B2 | 8/2004 | Michelson |
| 6,773,460 B2 | 8/2004 | Jackson |
| 6,793,679 B2 | 9/2004 | Michelson |
| 6,808,537 B2 | 10/2004 | Michelson |
| 6,814,737 B2 | 11/2004 | Cauthen |
| 6,814,756 B1 | 11/2004 | Michelson |
| 6,824,565 B2 | 11/2004 | Muhanna et al. |
| 6,827,740 B1 | 12/2004 | Michelson |
| 6,830,570 B1 | 12/2004 | Frey et al. |
| 6,830,574 B2 | 12/2004 | Heckele et al. |
| 6,833,006 B2 | 12/2004 | Foley et al. |
| 6,835,208 B2 | 12/2004 | Marchosky |
| 6,849,093 B2 | 2/2005 | Michelson |
| 6,863,673 B2 | 3/2005 | Gerbec et al. |
| 6,893,465 B2 | 5/2005 | Huang |
| 6,902,566 B2 | 6/2005 | Zucherman et al. |
| 6,902,579 B2 | 6/2005 | Harms et al. |
| 6,908,485 B2 | 6/2005 | Crozet et al. |
| 6,923,814 B1 | 8/2005 | Hildebrand et al. |
| 6,932,844 B2 | 8/2005 | Ralph et al. |
| 6,942,698 B1 | 9/2005 | Jackson |
| 7,048,766 B2 | 5/2006 | Ferree |
| 7,060,073 B2 | 6/2006 | Frey et al. |
| 7,066,960 B1 | 6/2006 | Dickman |
| 7,070,598 B2 | 7/2006 | Lim et al. |
| 7,081,120 B2 | 7/2006 | Li et al. |
| 7,083,650 B2 | 8/2006 | Moskowitz et al. |
| 7,084,766 B2 | 8/2006 | Sayegh et al. |
| 7,087,055 B2 | 8/2006 | Lim et al. |
| 7,090,680 B2 | 8/2006 | Bonati et al. |
| 7,128,760 B2 | 10/2006 | Michelson |
| 7,156,849 B2 | 1/2007 | Dunbar et al. |
| 7,163,561 B2 | 1/2007 | Michelson |
| 7,179,294 B2 | 2/2007 | Eisermann et al. |
| 7,195,643 B2 | 3/2007 | Jackson |
| 7,195,645 B2 | 3/2007 | Disilvestro et al. |
| 7,204,853 B2 | 4/2007 | Gordon et al. |
| 7,208,014 B2 | 4/2007 | Ralph et al. |
| 7,316,714 B2 | 1/2008 | Gordon et al. |
| 7,318,839 B2 | 1/2008 | Malberg et al. |
| 7,326,251 B2 | 2/2008 | McCombe et al. |
| 7,335,208 B2 | 2/2008 | Cavagna et al. |
| 7,621,658 B2 | 11/2009 | Zdeblick et al. |
| 7,645,232 B2 | 1/2010 | Shluzas |
| 7,686,805 B2 | 3/2010 | Michelson |
| 8,062,373 B2 | 11/2011 | Fabian, Jr. |
| 8,066,709 B2 | 11/2011 | Michelson |
| 8,070,754 B2 | 12/2011 | Fabian et al. |
| 8,075,593 B2 | 12/2011 | Hess |
| 8,236,058 B2 | 8/2012 | Fabian et al. |
| 8,579,977 B2 | 11/2013 | Fabian |
| 8,986,384 B2 * | 3/2015 | Malberg ............... A61F 2/442 623/17.11 |
| 9,271,843 B2 | 3/2016 | Fabian et al. |
| 9,421,113 B2 | 8/2016 | Fabian |
| 2002/0045904 A1 | 4/2002 | Fuss et al. |
| 2002/0045944 A1 | 4/2002 | Muhanna et al. |
| 2002/0055745 A1 | 5/2002 | McKinley et al. |
| 2003/0114860 A1 | 6/2003 | Cavagna et al. |
| 2003/0139812 A1 | 7/2003 | Garcia et al. |
| 2004/0153089 A1 | 8/2004 | Zdeblick et al. |
| 2004/0210313 A1 | 10/2004 | Michelson |
| 2004/0225295 A1 | 11/2004 | Zubok et al. |
| 2004/0230100 A1 | 11/2004 | Shluzas |
| 2004/0230309 A1 | 11/2004 | DiMauro et al. |
| 2004/0236331 A1 | 11/2004 | Michelson |
| 2004/0249388 A1 | 12/2004 | Michelson |
| 2005/0209698 A1 | 9/2005 | Gordon et al. |
| 2006/0030860 A1 | 2/2006 | Peterman |
| 2006/0096275 A1 | 5/2006 | Robel et al. |
| 2007/0073398 A1 | 3/2007 | Fabian et al. |
| 2008/0109005 A1 | 5/2008 | Trudeau et al. |
| 2008/0243255 A1 | 10/2008 | Butler et al. |
| 2008/0287957 A1 | 11/2008 | Hester et al. |
| 2008/0300601 A1 | 12/2008 | Fabian et al. |
| 2009/0048676 A1 | 2/2009 | Fabian, Jr. |
| 2009/0054988 A1 | 2/2009 | Hess |
| 2009/0138055 A1 | 5/2009 | Altarac et al. |
| 2009/0270873 A1 | 10/2009 | Fabian |
| 2009/0326543 A1 | 12/2009 | Fabian, Jr. |

(56) References Cited

U.S. PATENT DOCUMENTS

| | | |
|---|---|---|
| 2011/0276141 A1 | 11/2011 | Caratsch |
| 2011/0301711 A1 | 12/2011 | Palmatier et al. |
| 2012/0029645 A1 | 2/2012 | Fabian et al. |
| 2012/0197299 A1 | 8/2012 | Fabian, Jr. |
| 2012/0265310 A1 | 10/2012 | Fabian |
| 2013/0030535 A1 | 1/2013 | Foley et al. |
| 2013/0166031 A1 | 6/2013 | Caratsch |
| 2013/0268077 A1 | 10/2013 | You et al. |
| 2013/0310939 A1 | 11/2013 | Fabian et al. |
| 2014/0163684 A1 | 6/2014 | Donner et al. |
| 2018/0360617 A1* | 12/2018 | Fabian .................. A61F 2/4684 |
| 2020/0054459 A1 | 2/2020 | Smith et al. |

FOREIGN PATENT DOCUMENTS

| | | |
|---|---|---|
| EP | 2062555 A1 | 5/2009 |
| FR | 2717068 | 9/1995 |
| WO | 9814142 A1 | 4/1998 |
| WO | 200101895 A1 | 1/2001 |
| WO | 200205733 A1 | 1/2002 |

\* cited by examiner

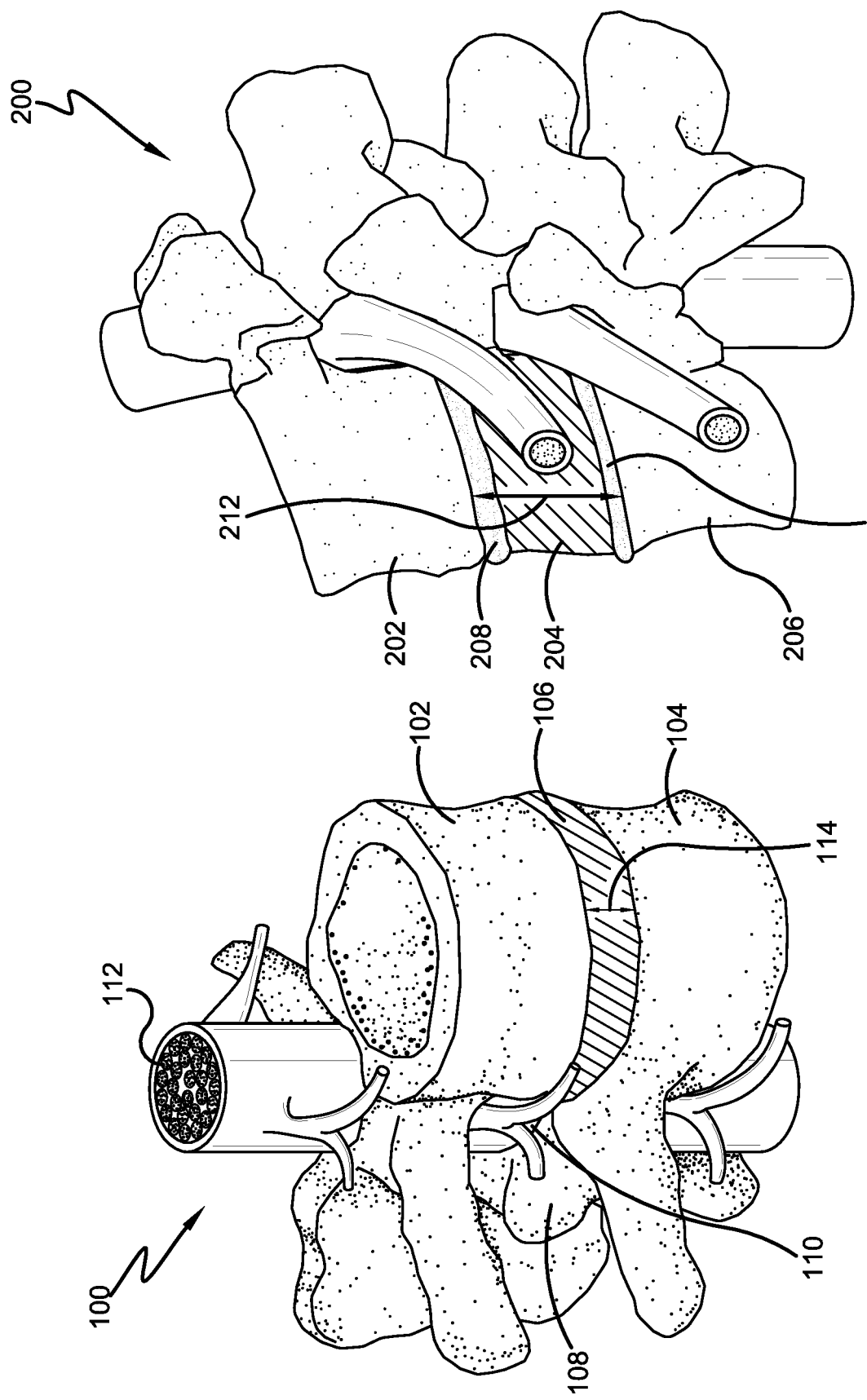

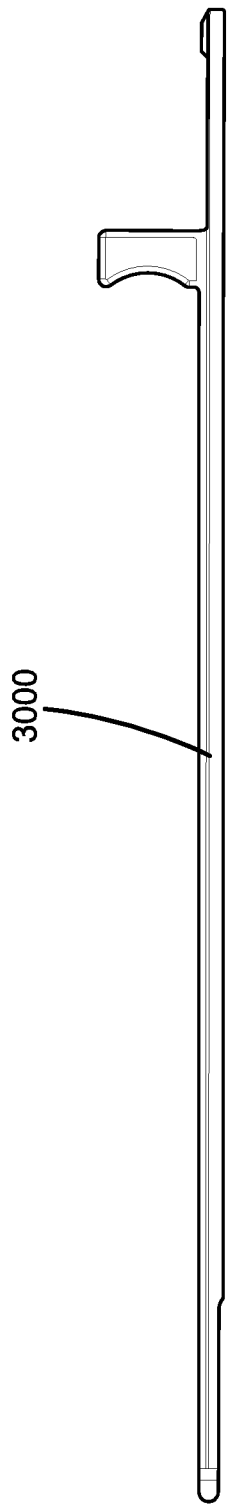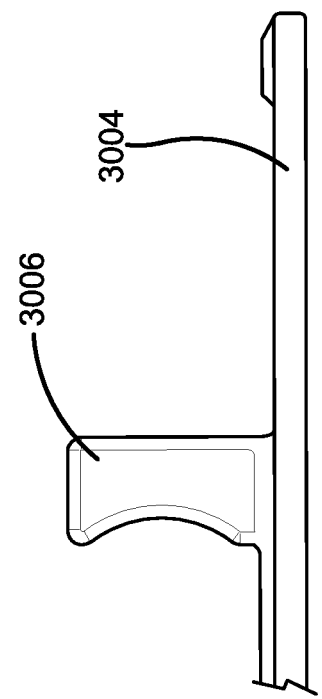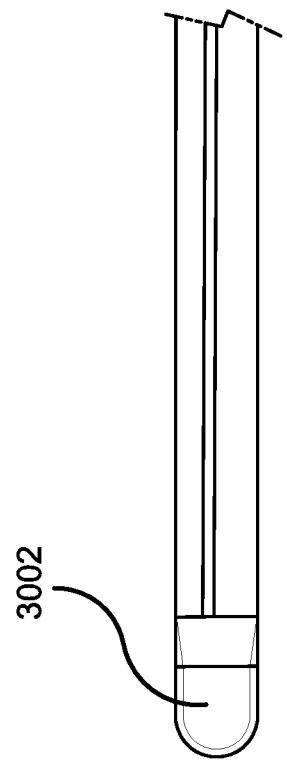
FIG. 52
FIG. 54
FIG. 53

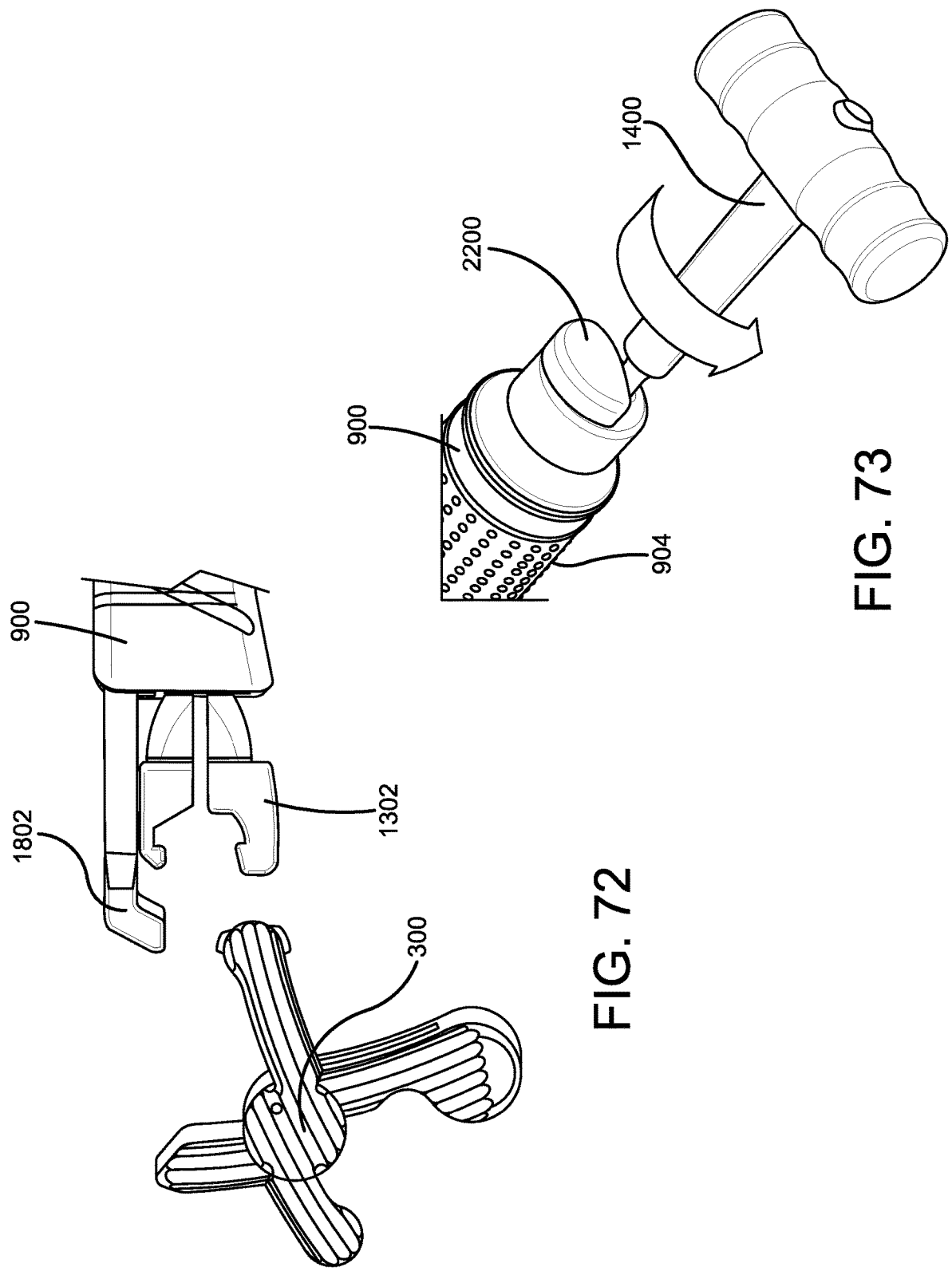

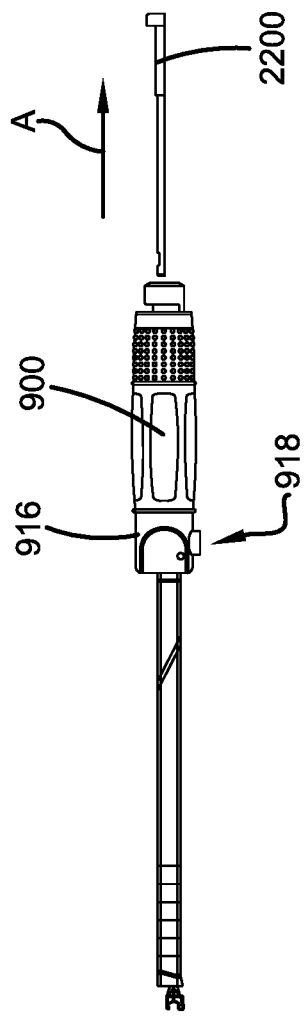
FIG. 74
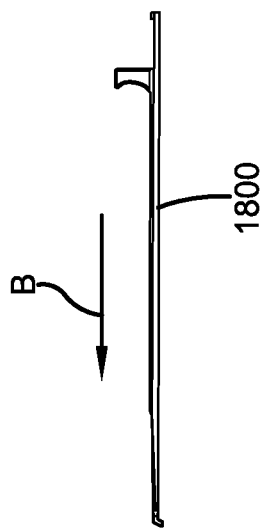
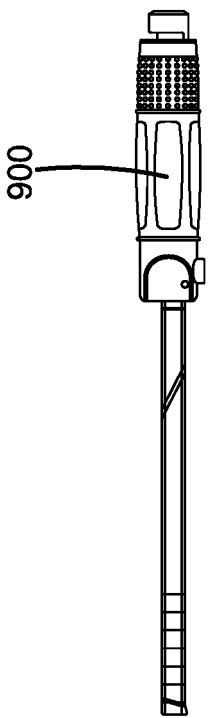
FIG. 75

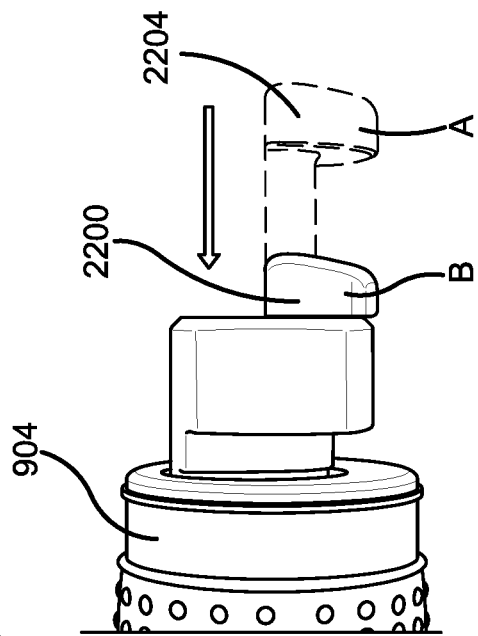
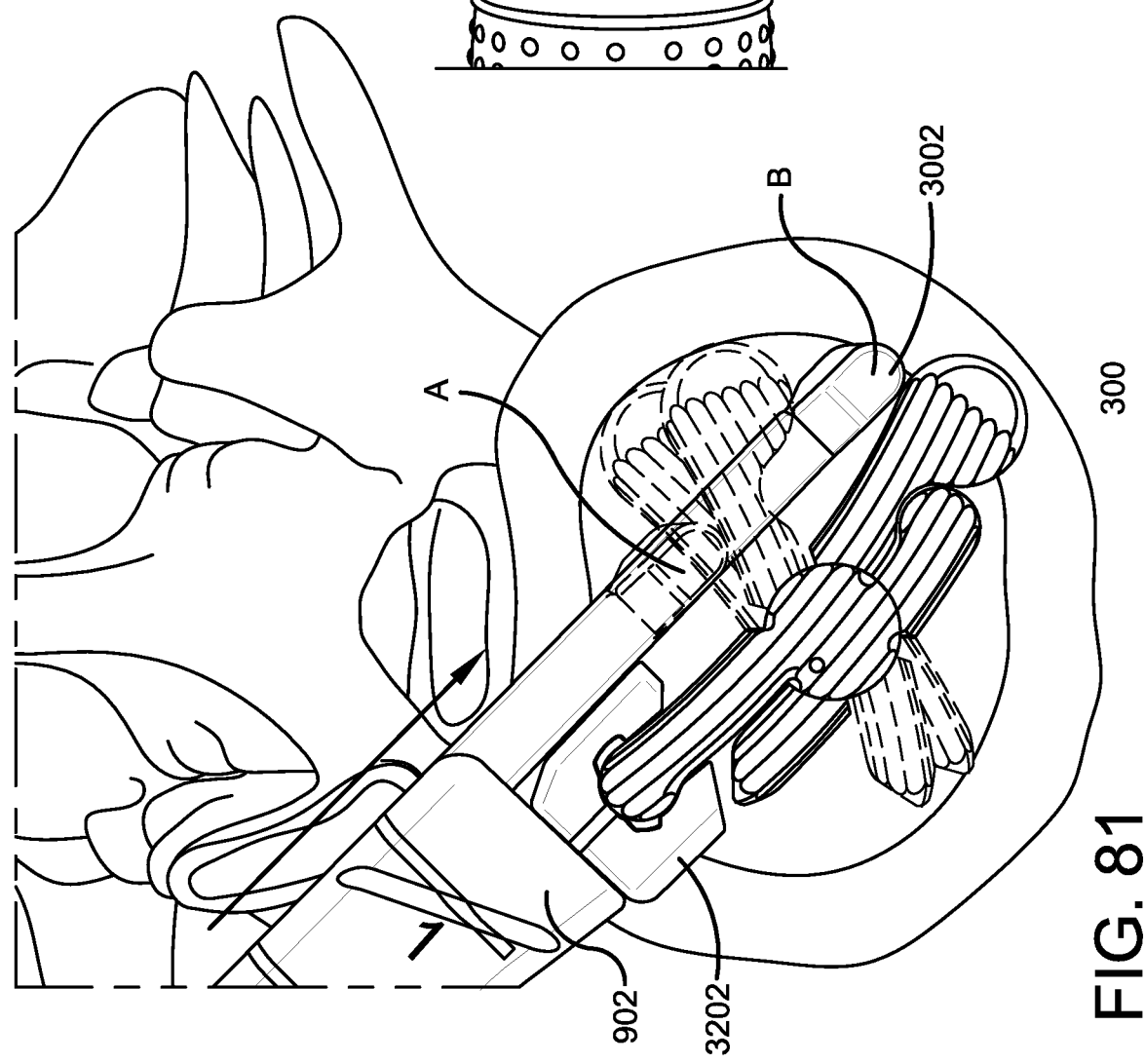
FIG. 81
FIG. 82

SPINE SURGERY METHOD AND INSTRUMENTATION

This application claims the benefit of U.S. Provisional Application No. 62/954,972, titled SPINE SURGER METHOD AND INSTRUMENTATION, filed Dec. 30, 2019, the entirety of which is fully incorporated by reference herein.

I. BACKGROUND OF THE INVENTION

A. Field of Invention

This invention pertains to the art of methods and apparatuses regarding spine surgery and more specifically relates to surgical procedures, a spinal implant and surgical instrumentation used to position the spinal implant and to deploy the implant within a vertebral space.

B. Description of the Related Art

The volume of spinal surgeries to treat degenerative disc and facet disease has steadily increased over the past decades, fueled by population demographics and advancements in diagnostic and instrumentation adjuncts. Improvements in intraoperative radiological imaging and surgical technique have generated a great deal of interest in applying minimally invasive surgical (MIS) techniques to spinal applications. As in other surgical subspecialties, it is hoped such minimally invasive techniques applied to spinal surgery will result in less soft tissue trauma, less operative blood loss, reduced operative time, faster recovery periods and lower costs.

Known spinal surgical techniques, though generally working well for their intended purposes, have been adopted from traditional open surgical (non-MIS) techniques. As a result, known spinal surgical methods, instrumentation and interbody implants have limitations. One limitation is that the physical components are relatively large and bulky. This reduces surgeon visualization of the surgical site. Another limitation of known spinal surgical methods is that known surgical tools and implants are cumbersome and difficult to maneuver within the limited surgical space available. The limitations of current instrumentation in MIS spine surgery are noted particularly with regards to interbody fusion surgery.

The present invention provides methods and apparatuses for overcoming these limitations by providing surgical procedures, a spinal implant and surgical instrumentation used to position the spinal implant within a vertebral space while in a contracted or non-deployed condition and then adjust the spinal implant into an expanded or deployed condition while in the vertebral space.

II. SUMMARY OF THE INVENTION

According to some embodiments of this invention, surgical instrumentation may be used with an associated intradiscal space comprising a first vertebral body having a first endplate and a second vertebral body adjacent the first vertebral body having a second endplate. The surgical instrumentation may comprise: an implant comprising: 1) a first portion; 2) a second portion that is pivotal with respect to the first portion; 3) wherein the first and second portions define first and second contact surfaces adapted to contact the first and second endplates, respectively; and 4) wherein the implant is deployable by pivoting the second portion with respect to the first portion; an inserter adapted to insert the implant into the associated intradiscal space when not deployed and to deploy the implant within the associated intradiscal space, the inserter comprising: 1) a handle; 2) a sheath including: (a) a proximal end supported to the handle; (b) a distal end, opposite the proximal end; (c) a longitudinally extending channel that extends from the proximal end to the distal end and gives the sheath a tube shape; and (d) a groove formed at the distal end that communicates with the longitudinally extending channel; 3) a gripping device including: (a) a proximal end supported to the handle; (b) a distal end, opposite the proximal end, adapted to grip and release the first portion of the implant; (c) a longitudinally extending channel that extends from the proximal end to the distal end and gives the gripping device a tube shape; (d) a groove formed at the distal end that communicates with the longitudinally extending channel; and (e) wherein the gripping device is positioned within the longitudinally extending channel of the sheath; 4) a pusher including: (a) a proximal end supported to the handle; (b) a distal end, opposite the proximal end; (c) an implant engagement finger supported to the distal end; (d) wherein the pusher is positioned within the longitudinally extending channel of the gripping device; and (e) wherein the implant engagement finger includes: (i) a first portion that extends through the groove in the gripping device and into the groove in the sheath; and (ii) a second portion that extends along the groove in the sheath and is adapted to contact the implant. The sheath may be: (a) operable to be moved distally to cause the gripping device to grip the first portion of the implant; and (b) operable to be moved proximally to cause the gripping device to release the first portion of the implant. The pusher may be: (a) operable to be moved proximally away from the implant; and (b) operable to be moved distally to cause the implant engagement finger to engage the second portion of the implant to deploy the implant when the gripping device grips the first portion of the implant.

According to some embodiments of this invention, a surgical instrumentation method may be used with an associated intradiscal space comprising a first vertebral body having a first endplate and a second vertebral body adjacent the first vertebral body having a second endplate. The surgical instrumentation method may comprise the steps of: A) providing an implant comprising: 1) a first portion; 2) a second portion that is pivotal with respect to the first portion; and 3) wherein the first and second portions define first and second contact surfaces adapted to contact the first and second endplates, respectively; B) providing an inserter comprising: 1) a handle; 2) a sheath including: (a) a proximal end supported to the handle; (b) a distal end, opposite the proximal end; (c) a longitudinally extending channel that extends from the proximal end to the distal end and gives the sheath a tube shape; and (d) a groove formed at the distal end that communicates with the longitudinally extending channel; 3) a gripping device including: (a) a proximal end supported to the handle; (b) a distal end, opposite the proximal end, adapted to grip and release the first portion of the implant; (c) a longitudinally extending channel that extends from the proximal end to the distal end and gives the gripping device a tube shape; and (d) a groove formed at the distal end that communicates with the longitudinally extending channel; and 3) a pusher including: (a) a proximal end supported to the handle; (b) a distal end, opposite the proximal end; and (c) an implant engagement finger supported to the distal end; C) providing the implant to be deployable by pivoting the second portion of the implant with respect to the first portion of the implant; D) providing the gripping device to be positionable within the longitudinally extending channel of the sheath; E) providing the pusher to be positionable within the longitudinally extending channel of the gripping device; F) providing the implant engagement finger with: 1) a first portion that is extendable through the groove in the gripping device and into the groove in the sheath; and 2) a second portion that is extendable along the groove in the sheath and that is adapted to contact the implant; G) providing the inserter to be operable to insert the implant into the associated intradiscal space when not deployed and to deploy the implant within the associated intradiscal space; H) providing the sheath to be operable to be moved distally to cause the gripping device to grip the first portion of the implant and to be moved proximally to cause the gripping device to release the first portion of the implant; and I) providing the pusher to be operable to be moved proximally away from the implant and to be moved distally to cause the implant engagement finger to engage the second portion of the implant to deploy the implant when the gripping device grips the first portion of the implant.

According to some embodiments of this invention, an inserter may be used with: an associated intradiscal space comprising a first vertebral body having a first endplate and a second vertebral body adjacent the first vertebral body having a second endplate; and, an associated implant comprising: 1) a first portion; 2) a second portion that is pivotal with respect to the first portion; 3) wherein the first and second portions define first and second contact surfaces adapted to contact the first and second endplates, respectively; and 4) wherein the associated implant is deployable by pivoting the second portion with respect to the first portion. The inserter may be adapted to insert the associated implant into the associated intradiscal space when not deployed and to deploy the associated implant within the associated intradiscal space. The inserter may comprise: 1) a handle; 2) a sheath including: (a) a proximal end supported to the handle; (b) a distal end, opposite the proximal end; (c) a longitudinally extending channel that extends from the proximal end to the distal end and gives the sheath a tube shape; and (d) a groove formed at the distal end that communicates with the longitudinally extending channel; 3) a gripping device including: (a) a proximal end supported to the handle; (b) a distal end, opposite the proximal end, adapted to grip and release the first portion of the associated implant; (c) a longitudinally extending channel that extends from the proximal end to the distal end and gives the gripping device a tube shape; (d) a groove formed at the distal end that communicates with the longitudinally extending channel; and (e) wherein the gripping device is positioned within the longitudinally extending channel of the sheath; 4) a pusher including: (a) a proximal end supported to the handle; (b) a distal end, opposite the proximal end; (c) an implant engagement finger supported to the distal end; (d) wherein the pusher is positioned within the longitudinally extending channel of the gripping device; and (e) wherein the implant engagement finger includes: (i) a first portion that extends through the groove in the gripping device and into the groove in the sheath; and (ii) a second portion that extends along the groove in the sheath and is adapted to contact the associated implant. The sheath may be: (a) operable to be moved distally to cause the gripping device to grip the first portion of the associated implant; and (b) operable to be moved proximally to cause the gripping device to release the first portion of the associated implant. The pusher may be: (a) operable to be moved proximally away from the associated implant; and (b) operable to be moved distally to cause the implant engagement finger to engage the second portion of the associated implant to deploy the associated implant when the gripping device grips the first portion of the associated implant.

Numerous benefits and advantages of the invention will become apparent to those skilled in the art to which it pertains upon a reading and understanding of the following detailed specification

III. BRIEF DESCRIPTION OF THE DRAWINGS

The invention may take physical form in certain parts and arrangement of parts, embodiments of which will be described in detail in this specification and illustrated in the accompanying drawings which form a part hereof and wherein:

FIG. 1 is a side perspective view of a spinal segment showing a vertebral space defined by the intradiscal space usually occupied by a disc between two adjacent vertebral bodies.

FIG. 2 is a side perspective view of a spinal segment showing a vertebral space defined by the space usually occupied by a vertebral body and its two adjacent discs.

FIG. 52 is a side view of a remover tamp.

FIG. 53 is a close-up view of the distal end of the remover tamp shown in FIG. 52.

FIG. 54 is a close-up view of the proximal end of the remover tamp shown in FIG. 52.

FIG. 72 is a top view of a gripper that has released a spinal implant.

FIG. 73 is a perspective view of the proximal end of an inserter illustrating a tool being rotated to release a spinal implant.

FIG. 74 is a side view illustrating how an inserter tamp and impactor can be removed from an inserter.

FIG. 75 is a side view illustrating how a gripping device can be removed from an inserter.

FIG. 81 illustrates a remover tamp being extended to adjust a spinal implant from a deployed condition into a collapsed condition within a vertebral space.

FIG. 82 is a side view of the proximal end of an inserter showing the impactor being moved to adjust the spinal implant into a collapsed condition.

IV. DETAILED DESCRIPTION

Figure 4:
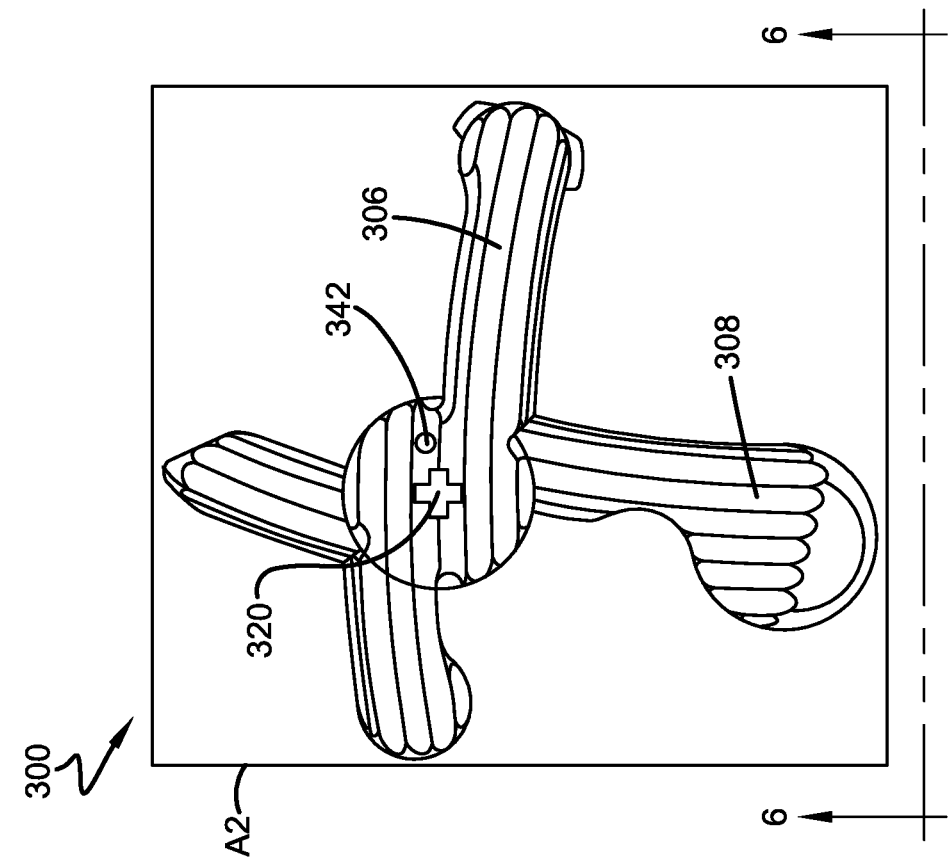
FIG. 4 is a top view of the spinal implant shown in FIG. 3 but in an expanded condition.

A spinal implant according to some aspects of the present teaching of this invention may be adjusted between a contracted or non-deployed condition and an expanded or deployed condition. This adjustment may be made when the implant is positioned within a vertebral space or when positioned outside of a vertebral space, such as prior to surgery. When an implant is adjusted from the expanded condition to the contracted condition while within a vertebral space, the resultant non-deployed condition is herein termed a collapsed condition. In some embodiments, a locking mechanism may be used to lock the implant in the deployed condition. The locking mechanism may be unlocked, permitting the implant to be adjusted from the deployed condition to the non-deployed condition.

Surgical instrumentation according to some aspects of the present teaching of this invention may be used to insert the implant within a vertebral space, while in the non-deployed condition, and adjust the implant into the deployed condition. In some embodiments, surgical instrumentation may be used to remove the implant from the vertebral space. In some embodiments the surgical instrumentation may be used to adjust the implant from the deployed condition into a collapsed condition before removing the implant. In what follows, numerous embodiments of spinal implants and surgical instrumentation will be described. Their use, according to some embodiments, will then be described.

Referring now to the drawings wherein the showings are for purposes of illustrating embodiments of the invention only and not for purposes of limiting the same, FIG. 1 illustrates a spinal segment 100 made up of two vertebral bodies 102, 104 attached together by ligaments with a disc 106 separating them. Facet joints 108 fit between the two vertebral bodies 102, 104 and allow for movement. The neural foramen 110 between the vertebral bodies 102, 104 allow space for the nerve roots to travel freely from the spinal cord 112 to the body. If it is required to remove the disc 106 and replaced it with an implant, the space occupied by the disc, the intradiscal space between the two adjacent vertebral bodies 102, 104, defines the vertebral space 114.

With reference now to FIG. 2, according to some aspects of the present teaching of this invention, a spinal segment 200 may be made up of three vertebrae 202, 204, 206 attached together by ligaments. If it is required to remove the middle vertebra 204 (it is shown diseased) along with the adjacent discs 208, 210, such as may be required because of a corpectomy defect, and replaced them with an implant, the space between the two outer vertebral bodies 202, 206, defines the vertebral space 212. It should be understood that these are simply two non-limiting examples of the vertebral space 114, 212 into which an implant can be inserted according to this invention because any vertebral space chosen with the sound judgment of a person of skill in the art can be used. As the components and operation of a spinal column is well known to those of skill in the art, further detail will not be provided here.

Figure 3:
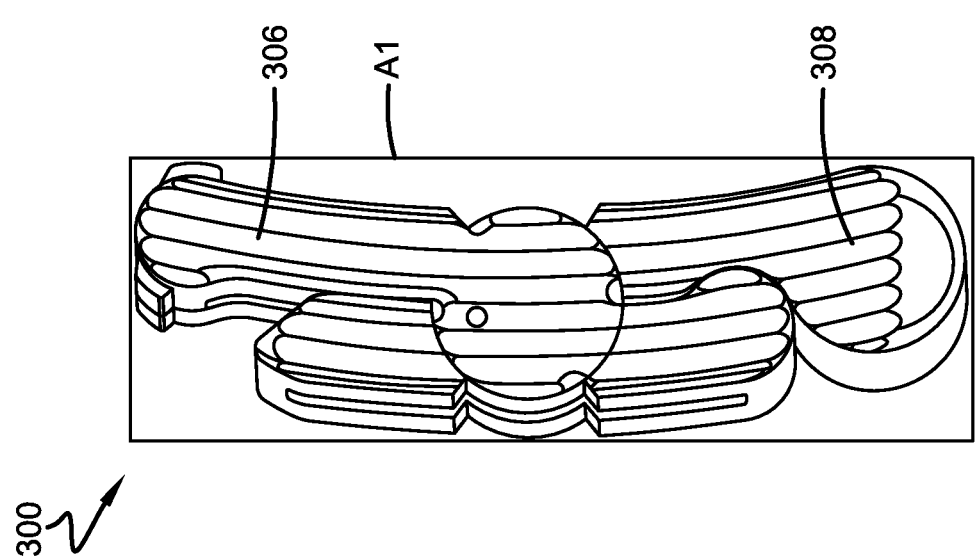
FIG. 3 is a top view of a spinal implant in a contracted condition.
Figure 6:
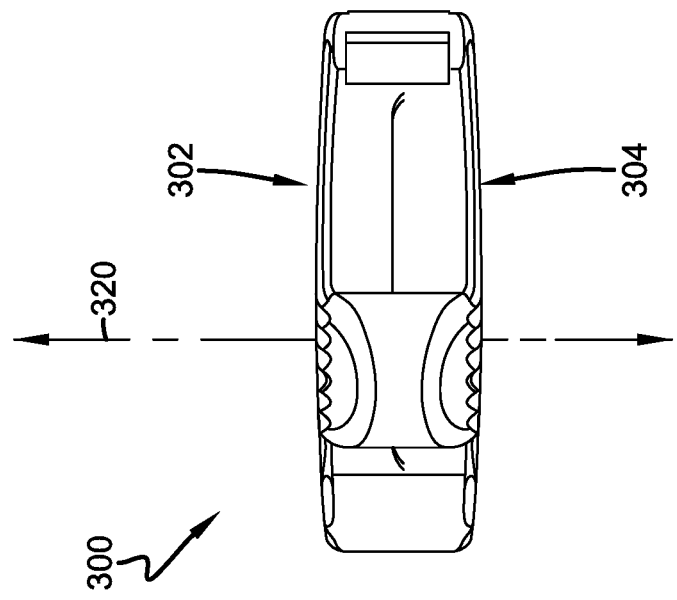
FIG. 6 is a view taken along the line 6-6 of FIG. 4.
Figure 5:
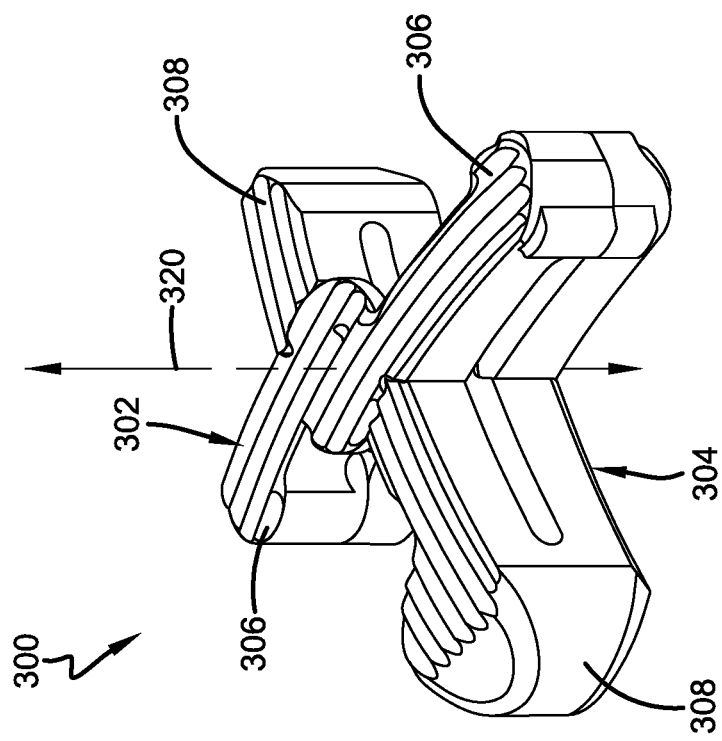
FIG. 5 is a top perspective view of the spinal implant shown in FIG. 4.
Figure 8:
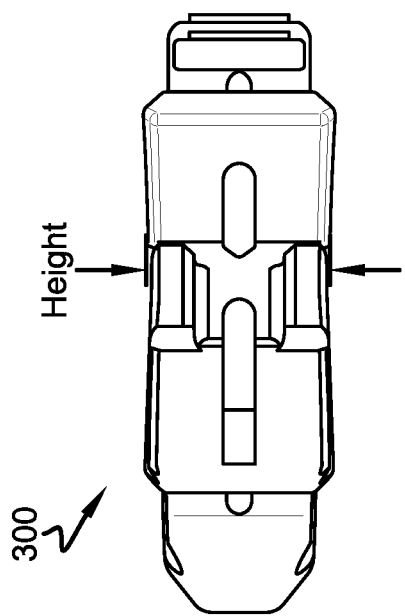
FIG. 8 is a side view of the spinal implant shown in FIG. 7.
Figure 7:
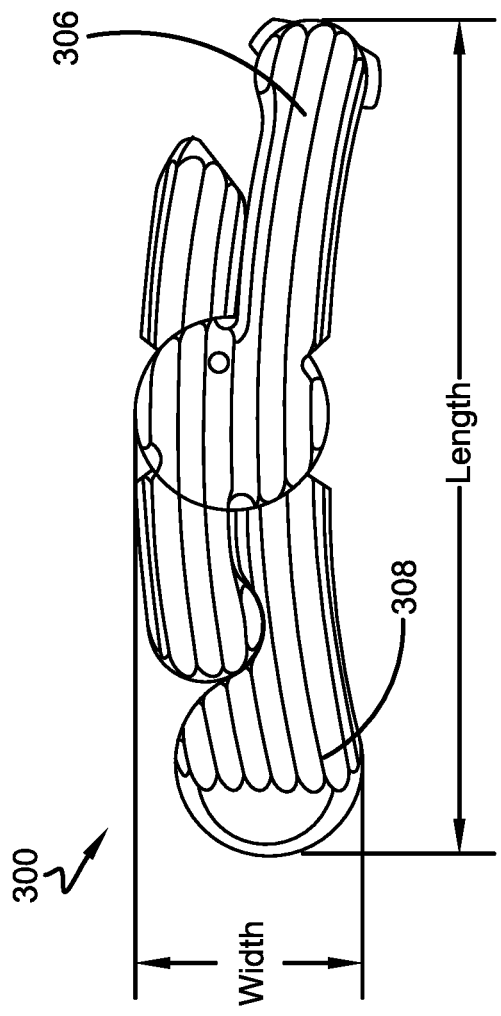
FIG. 7 is a top view of a spinal implant in a contracted condition.
Figure 9:
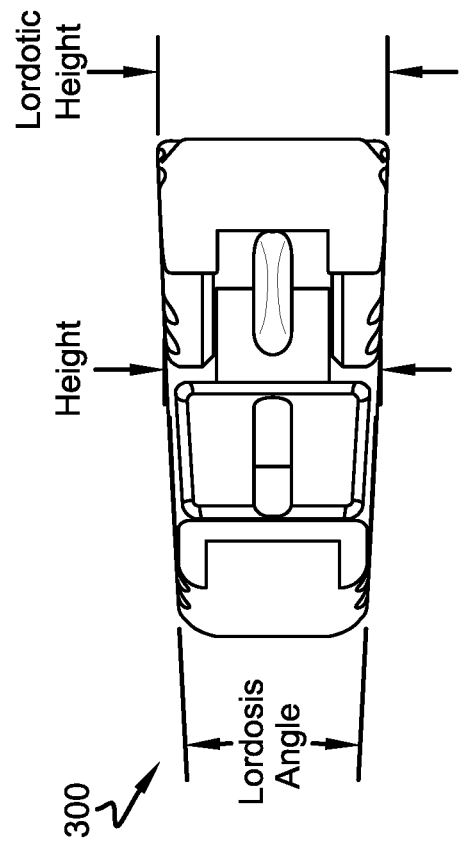
FIG. 9 is a side view of a deployed spinal implant.

With reference now to FIGS. 3-9, according to some aspects of the present teaching of this invention, an implant 300 may positioned within the vertebral space in a non-deployed or contracted condition, as shown in FIGS. 3 and 7, and then may be adjusted within the vertebral space into a deployed or expanded condition, as shown in FIGS. 4 and 5. This expandable design is very beneficial for the surgeon. When in the non-deployed, contracted, reduced footprint condition, the implant 300 is small enough to be passed through a standard microdiscectomy type annulotomy, making it truly compatible with minimally invasive surgical (MIS) techniques. Once placed within the vertebral space, the implant 300 may be adjusted into the deployed or expanded condition where it provides a larger effective footprint area. This larger footprint is compatible with more invasive anterior lumbar interbody fusion or bilateral posterior techniques. The implant 300 may have two vertebral body endplate contact surfaces 302, 304 (top and bottom as shown in FIGS. 5 and 6) that face and contact the respective vertebral bodies within the vertebral space (shown in FIGS. 1 and 2). These vertebral body endplate contact surfaces 302, 304 may be serrated/knurled to facilitate cutting into bony endplates to prevent rotation or expulsion of the implant by external rotational or flexion-extension forces. Each vertebral body endplate contact surface 302, 304 may provide a first effective footprint area A1, as illustrated in FIG. 3, when in the non-deployed condition. The implant 300 vertebral body endplate contact surfaces 302, 304 may have a second larger effective footprint area A2, as illustrated in FIG. 4, when in the deployed condition. For purposes of this patent, "effective footprint area" is defined in U.S. Pat. No. 8,062,373 which is incorporated herein by reference in its entirety. As shown in FIGS. 7-9, the implant 300 may have a width, a length, a height a lordotic height and a lordosis angle when in the non-deployed condition.

Figure 10:
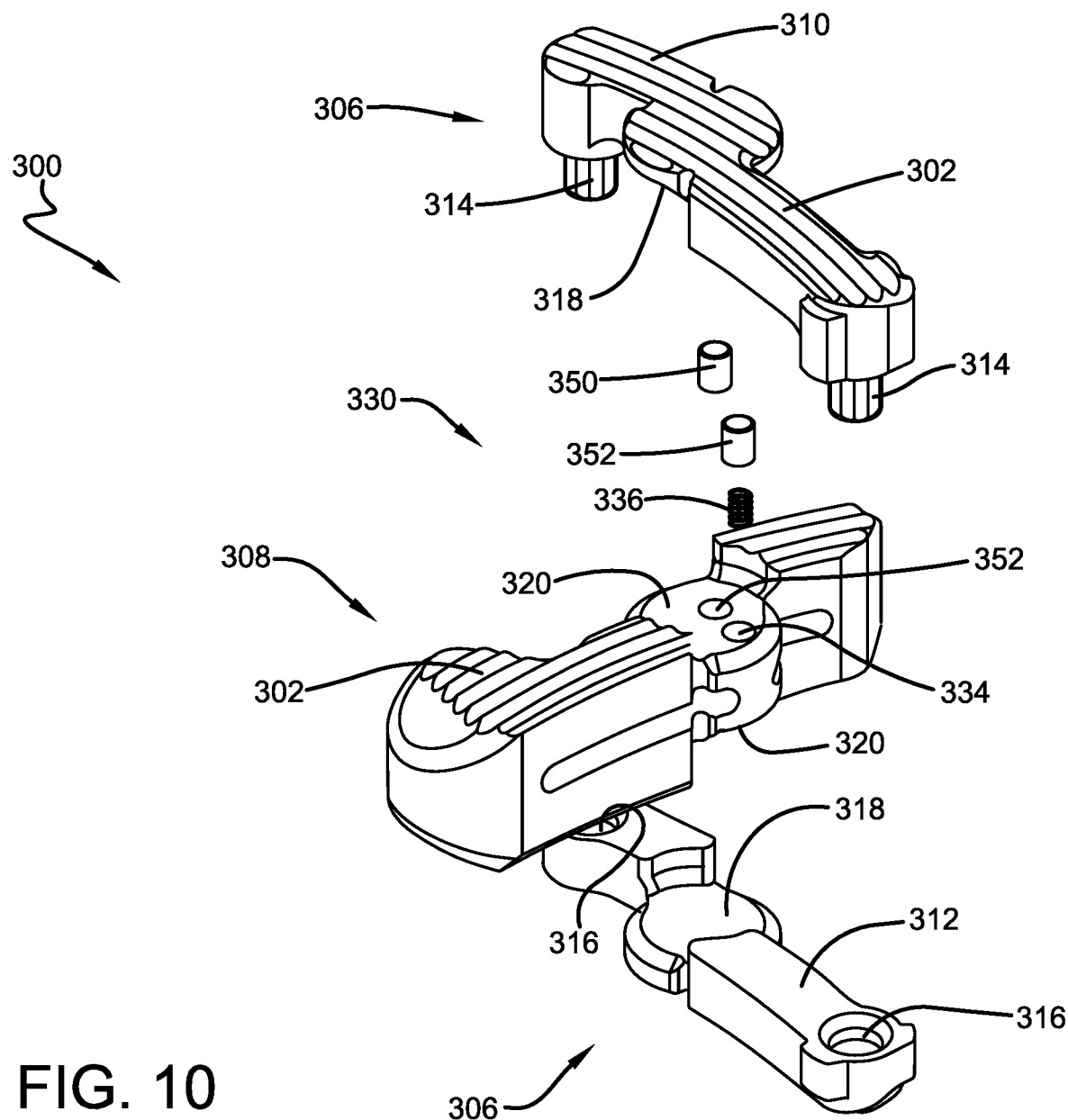
FIG. 10 is an assembly view of a spinal implant.
Figure 12:
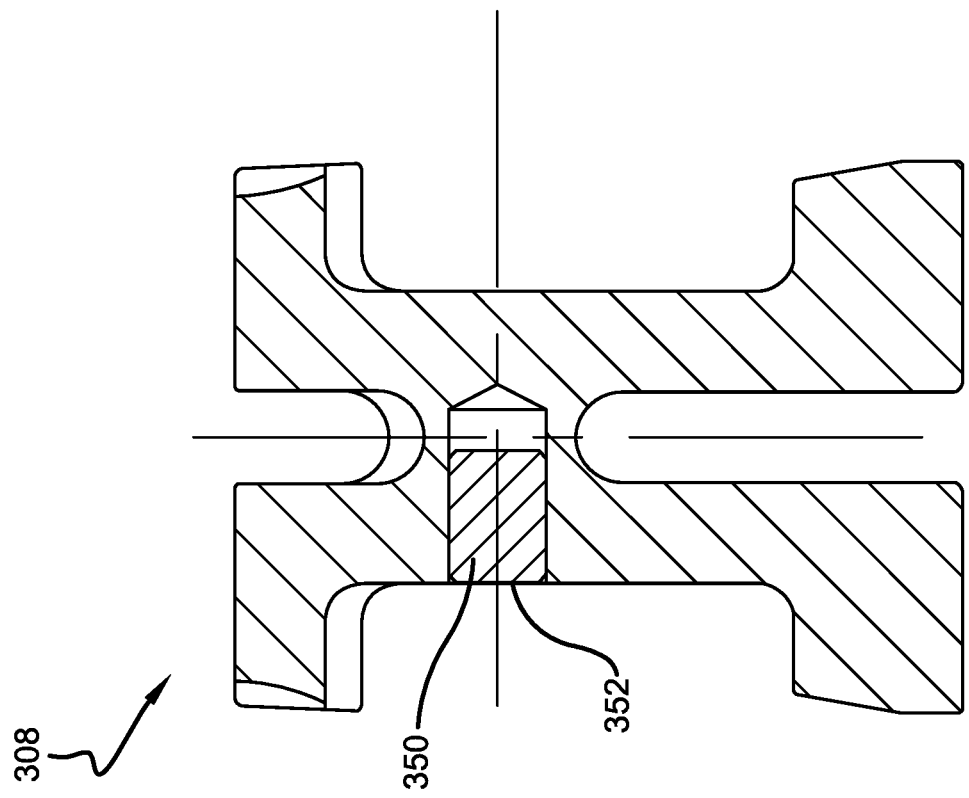
FIG. 12 is a view taken along the line 12-12 of FIG. 11.
Figure 11:
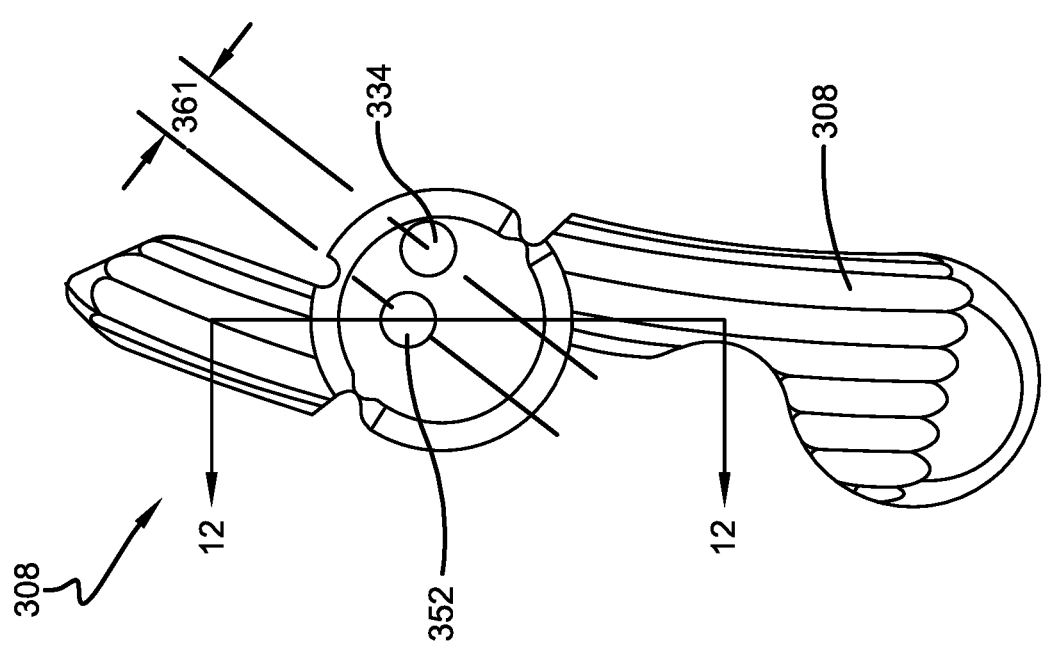
FIG. 11 is a top view of a spinal implant member.

With reference now to FIGS. 3-4 and 10, the implant 300 may include a first member 306 and a second member 308 that pivots with respect to the first member 306 between the non-deployed condition (FIG. 3) and the deployed condition (FIG. 4). While the specific design of the first and second members may be any chosen with the sound judgement of a person of skill in the art, for the embodiment shown the first member 306 has first and second beams 310, 312 that interconnect via posts 314, 314 that extend from opposite ends of beam 310 and that are received in corresponding slots 316, 316 formed on opposite ends of beam 312. While the posts shown extend from the first beam and the slots are formed in the second beam, it should be understood that in other embodiments this could be reversed and in yet other embodiments one post could extend from each beam with a corresponding post receiving slot in the opposite beam. Each beam 310, 312 may have mid-portions with contact surfaces 318, 318. The contact surfaces 318, 318 may be planar with generally circular shapes, as shown. The contact surfaces 318, 318 may be positioned in cut-out areas of the beams, as shown. The second member 308 may have a mid-portion with contact surfaces 322, 322 on opposite sides. The contact surfaces 322, 322 may be planar with generally circular shapes and may be positioned in cut-out areas of the beam, as shown. When the implant is assembled together, contact surfaces 318, 318 may engage corresponding contact surfaces 322, 322 providing the pivotal connection between the first and second members 306, 308. The pivotal connection may be about pivot axis 320, shown in FIGS. 4-6, which may define the axial directions indicated.

With reference now to FIGS. 3, 5 and 10, a locking mechanism 330 may be used to lock the first member 306 to the second member 308 preventing the first member 306 from pivoting with respect to the second member 308 about the pivot axis 320. The locking mechanism 330 may also, in some embodiments, be adjusted to unlock the first member 306 from the second member 308 permitting the first member 306 to pivot with respect to the second member 308 about the pivot axis 320. In some embodiments, the locking mechanism 330 locks the first member 306 to the second member 308 only when the implant is in the deployed condition (shown, for example, in FIG. 5). In some embodiments, the locking mechanism 330 locks the first member 306 to the second member 308 automatically when the desired relative position between the first and second members 306, 308 has been achieved. In some embodiments, the locking mechanism 330 can be unlocked in more than one way, according to the needs of the surgeon.

Figure 13:
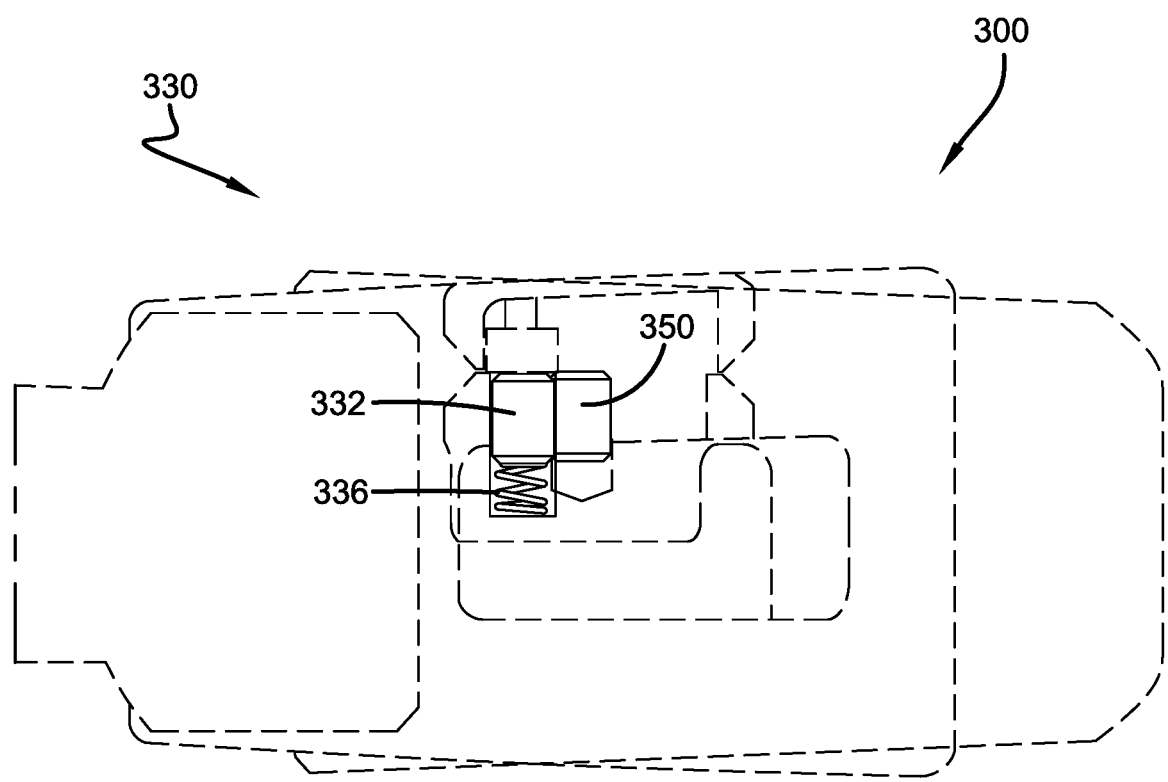
FIG. 13 is a side view of a spinal implant in a non-deployed condition as may be seen fluoroscopically with the relative positions of pins visible.
Figure 14:
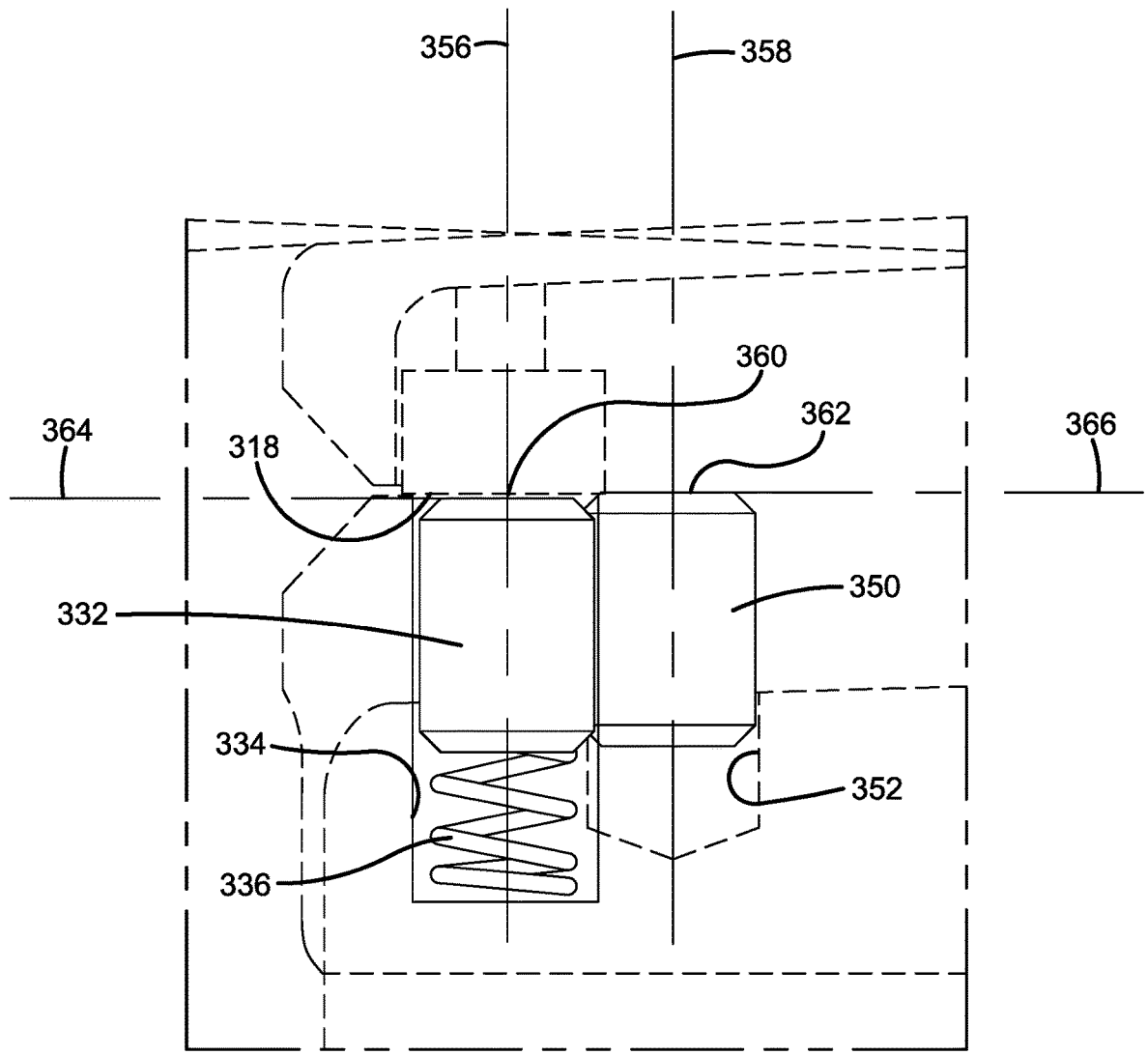
FIG. 14 is a close-up view of the pins shown in FIG. 13.
Figure 15:
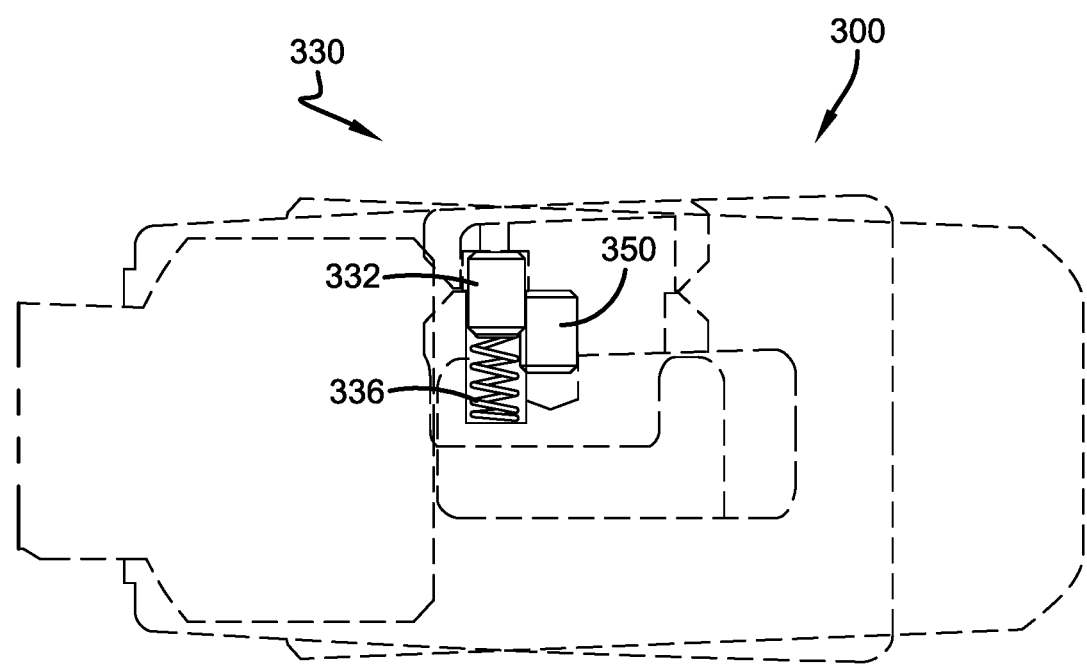
FIG. 15 is a view similar to that shown in FIG. 13 but with the spinal implant in a deployed condition.
Figure 16:
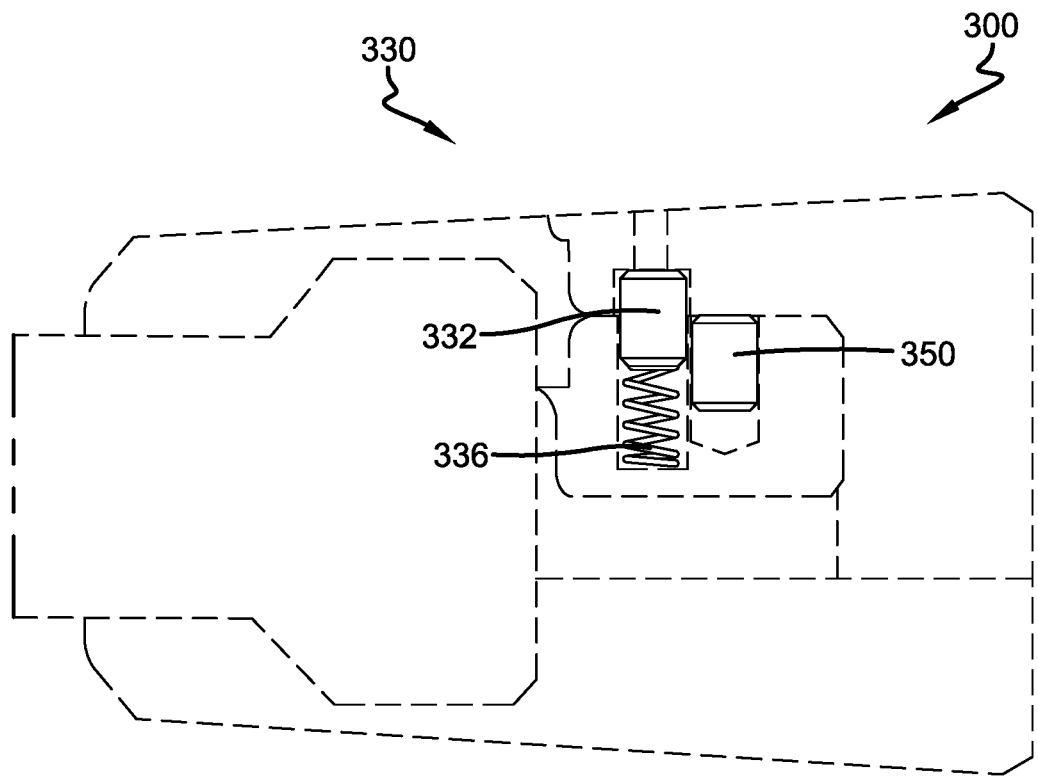
FIG. 16 is a view similar to that shown in FIG. 15 but from a lateral angle.
Figure 17:
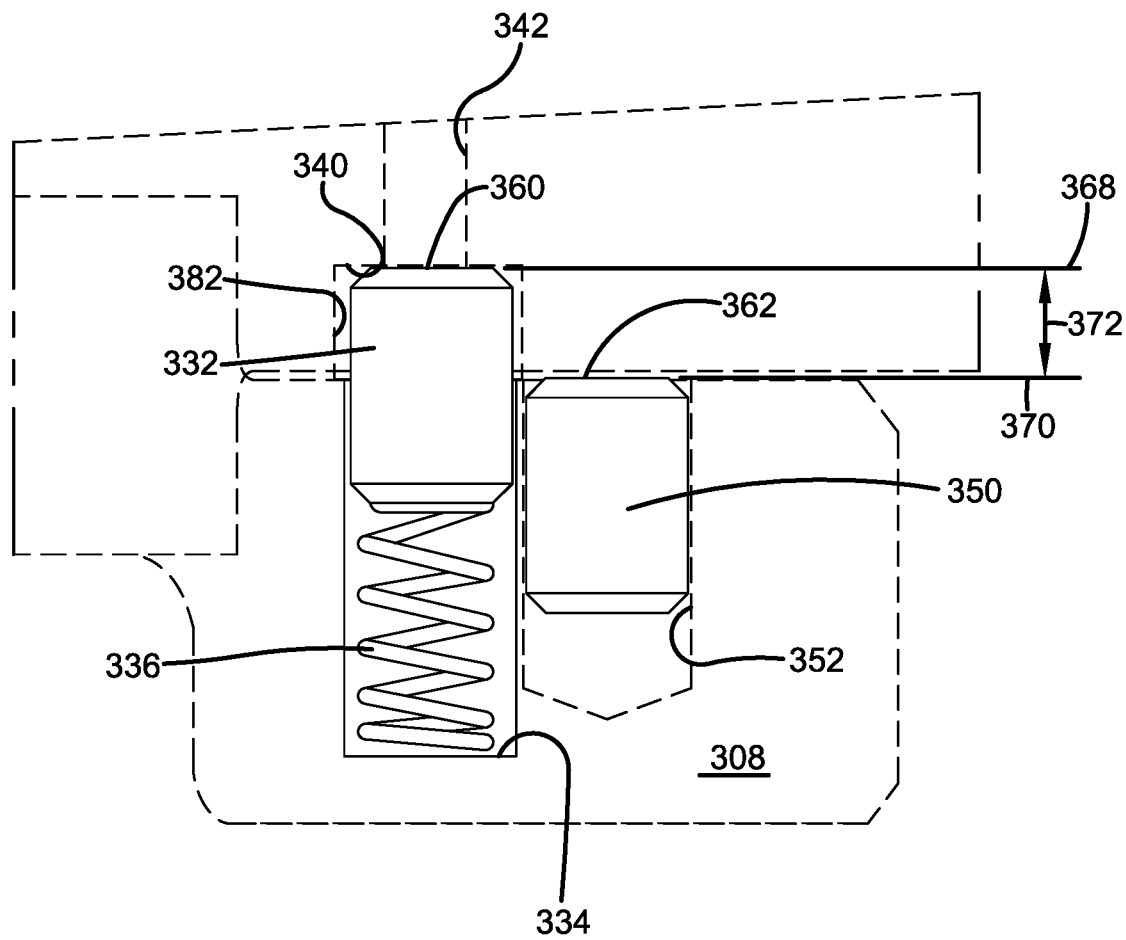
FIG. 17 is a close-up view of the pins shown in FIG. 16.

With reference now to FIGS. 10-11 and 13-17, for the embodiments shown, the locking mechanism 330 may include a pin 332 that is supported to the second member 308 and that is biased via a biasing force in an axial direction (upward in FIGS. 13-17). In some embodiments, pin 332 may be fluoroscopically detectable as distinct from the first and second members 306, 308 for purposes that will be discussed below. In one embodiment, the pin 332 is supported to second member 308 via placement within second member opening 334. In some embodiments, the biasing force is generated by a biasing force generator 336 in the form of a compression spring. The biasing force generator 336 may be supported within opening 334 and positioned between the second member 308 and the pin 332, as shown. With this arrangement, the biasing force generator 336 applies a biasing force to the pin 332 that biases the pin 332 in an axial direction (upward in FIGS. 13-17). The effect of the biasing force on the pin 332 may depend on the relative position of the first and second members 306, 308. When the first and second members 306, 308 are relatively positioned with an opening 338 formed in the first member 306 collinear with the pin 332, as shown in FIG. 15-17, the biasing force will move the pin 332 axially into the opening 338. Opening 338 may be defined by a surface 340 (FIG. 17) that a pin surface (upper surface in the FIGURES) of the pin 332 contacts, limiting how far the pin 332 can be moved by the biasing force into opening 338. When the pin 332 is positioned within opening 338 as just described, the locking mechanism 330 is in the locked condition as the pin 332 locks the first member 306 to the second member 308. In this condition, the first member 306 cannot rotate about the pivot axis 320 with respect to the second member 308. Note that the biasing force may be continual which causes the pin 332 to enter the opening 338 automatically when the opening 338 is collinear with the pin 332. The pin 332 and opening 338 may be positioned such that the locked condition only occurs when the implant is in the deployed condition. When the pin 332 is not collinear with the opening 338, as shown in FIGS. 13-14, the biasing force holds the pin 332 against the contact surface 318 of the first member 306, preventing the pin 332 from entering the opening 338. In this condition, the first member 306 can pivot about the pivot axis 320 with respect to the second member 308. This relative pivotal motion may be possible when the implant in in the non-deployed condition. It should be understood that though the use of only one pin has been described, one or more pins may be used as part of the locking mechanism 330 according to some aspects of the present teaching of this invention.

Figure 18:
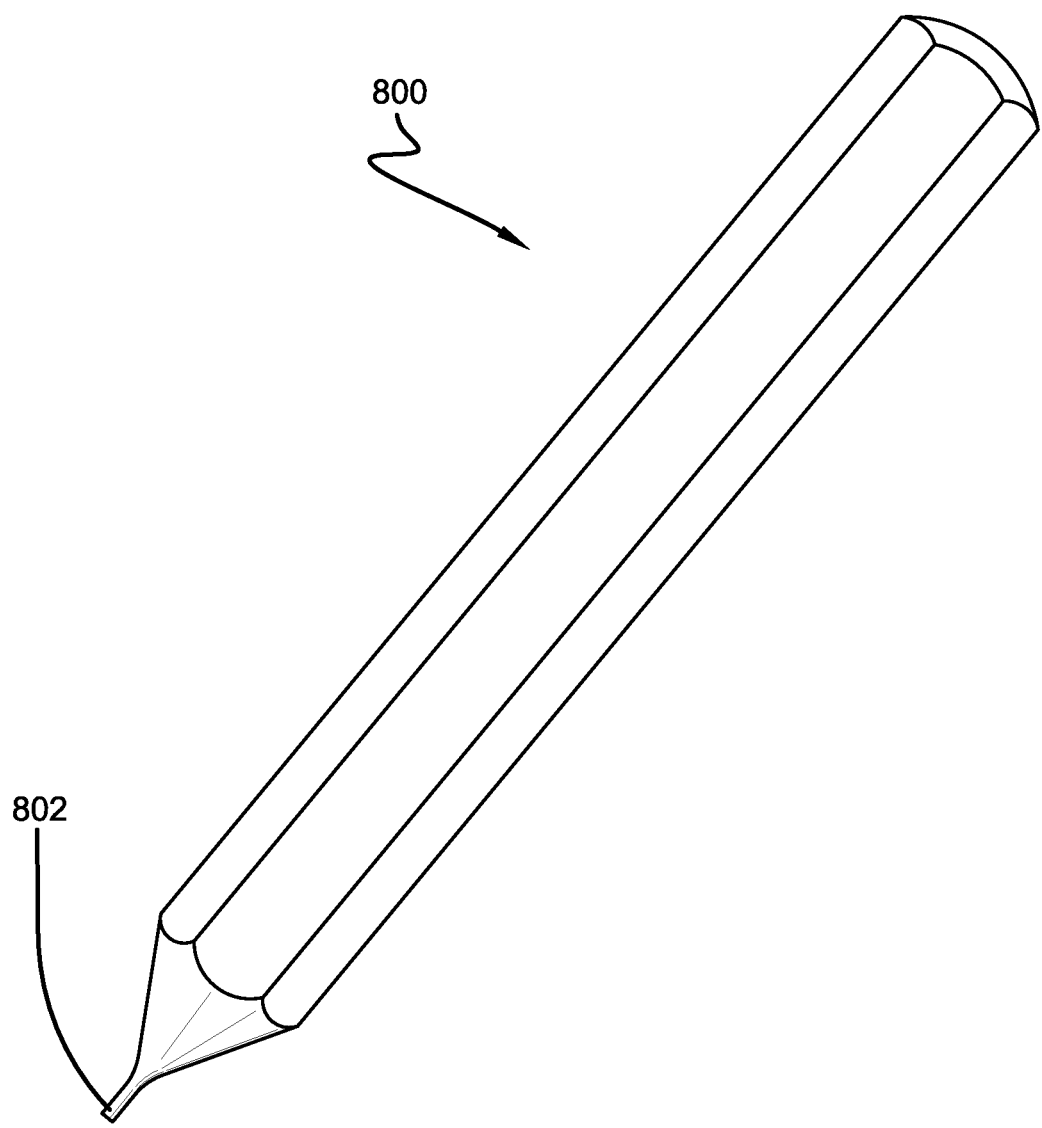
FIG. 18 is a side view of a lock release tool.

With reference now to FIGS. 4-5, 10, 13-14 and 17-18, according to some embodiments of this invention, the locking mechanism 330 may be unlocked, that is, the locking mechanism 330 may be adjusted to unlock the first member 306 from the second member 308 permitting the first member 306 to pivot with respect to the second member 308 about the pivot axis 320. The opening 338 may have opposite axial ends (top and bottom in the FIGURES). The pin 332 enters one axial end (the bottom as shown) as it creates the locked condition. The opposite axial end (the top as shown) may communicate with a cavity 342 (FIGS. 4 and 17) that also communicates outside the first member 306, as shown. The cavity 342 thus provides access to the pin 332. FIG. 18 shows a lock release tool 800. To adjust the locking mechanism 330 out of the locked condition, the surgeon may insert the tip 802 of the lock release tool 800 into the cavity 342 sufficient to contact the upper surface of the pin 332 and force the pin 332 out of the opening 338 in the first member 306 against the biasing force. This positions all of the pin 332 back into opening 334 in the second member 308 (shown in FIGS. 13-14) and thereby unlocks the locking mechanism 330. While maintaining the tip 802 against the pin 332 in this manner, the surgeon can easily pivot the first member 306 with respect to the second member 308. Once the unlocked condition has been achieved, the surgeon can simply remove the lock release tool 800. This use of release tool 800 may be used, for example, when the implant 300 has been inadvertently adjusted from its non-deployed condition into the deployed condition prior to placement within a patient.

Figure 19:
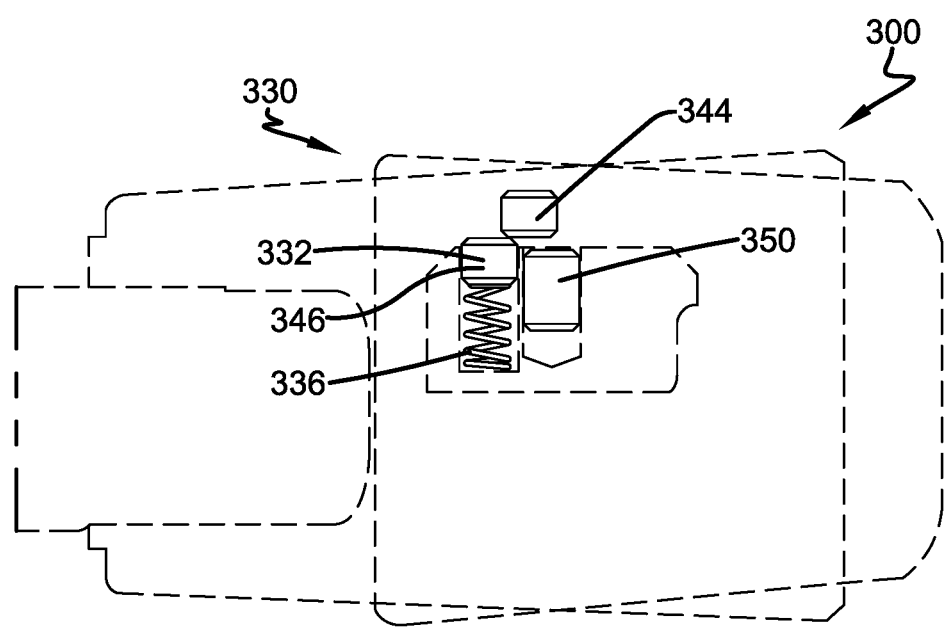
FIG. 19 is a view similar to that shown in FIG. 13 but with the spinal implant in a collapsed condition.
Figure 20:
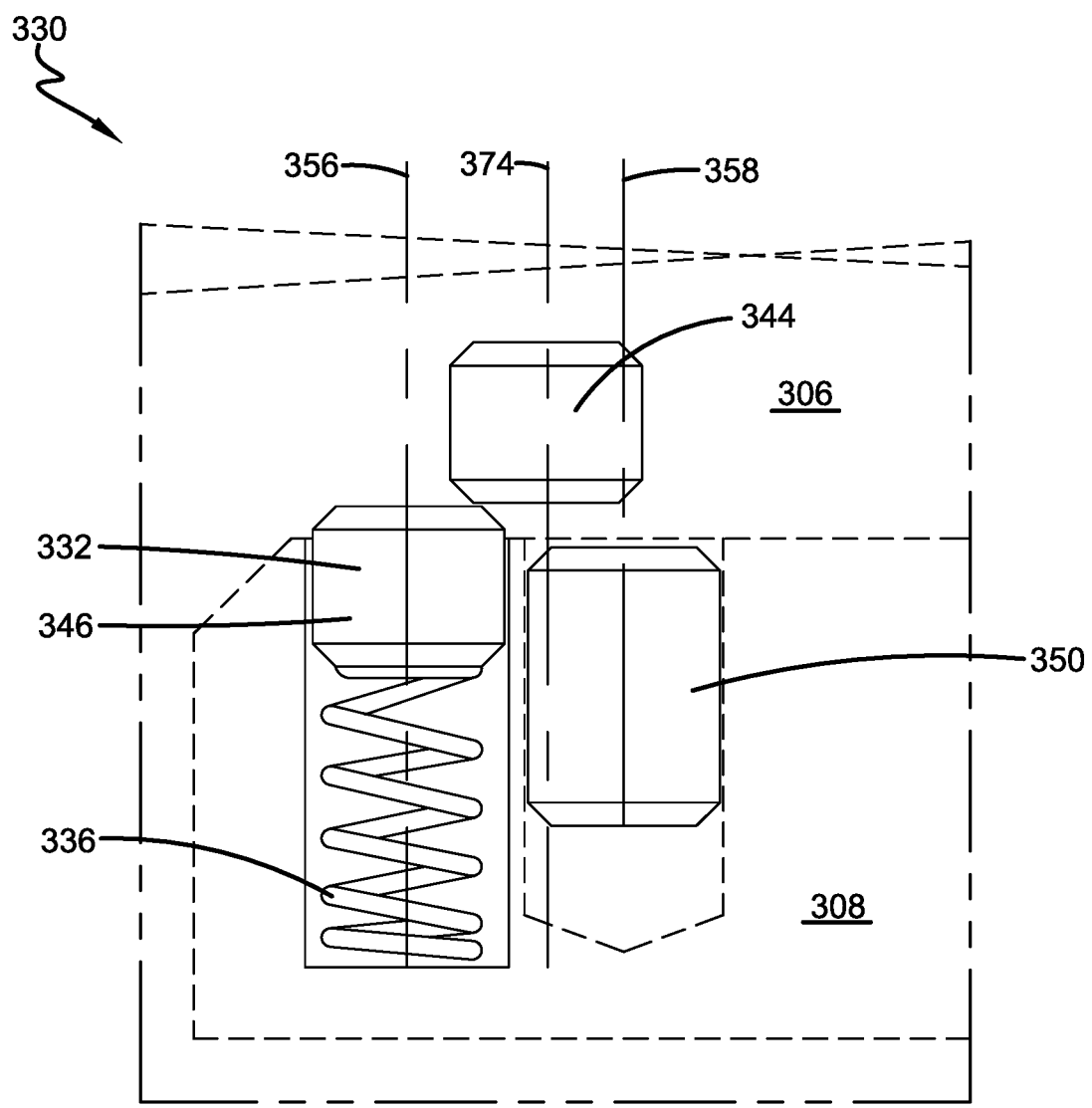
FIG. 20 is a close-up view of the pins shown in FIG. 19.

With reference now to FIGS. 5, 10 and 19-20, according to some embodiments of this invention, the locking mechanism 330 may be unlocked by separating the pin 332 into two (or more) portions. In one specific embodiment, the pin 332 may be sheared into two portions. This separation of the pin 332 may be used, for example, when the implant 300 is positioned within the vertebral space and has been deployed but needs to be collapsed and then removed. FIGS. 19-20 show the pin 332 separated into portions 344, 346. The surgeon may separate the pin 332 in a manner that will be discussed further below. Once separated, portion 344 may remain within in the opening 338 in first member 306 while portion 346 remains within opening 334 in the second member 308. In this way, the surgeon can rotate the first member 306 with respect to the second member 308 and then remove the implant 300. Note that when the implant is unlocked in this manner (separating pin 332), the implant can no longer be used with a patient.

With reference now to FIGS. 5 and 10-17, to assist the surgeon with more certain knowledge about the condition of the implant 300 (non-deployed or deployed)—especially when the implant is positioned within the patient's vertebral space—a pin 350 may be used as a reference with pin 332. Pin 350 may be fluoroscopically detectable as distinct from the first and second members 306, 308 and may be supported to either first member 306 or second member 308. For the embodiments shown, pin 350 is supported to the second member 308 via placement within second member opening 352. Pin 350 may be fixed to the second member such as, in one embodiment, by a press fit within opening 352. The surgeon may use the differing relative positions between pin 332 and pin 350 to determine the condition of the implant—non-deployed or deployed. In one embodiment, the surgeon may use the different relative axial positions between pins 332, 350 for this purpose.

With continuing reference to FIGS. 5 and 10-17, each pin may have a longitudinal axis that is parallel to the pivot axis 320. Specifically, as shown in FIG. 14, pin 332 may have a longitudinal axis 356 and pin 350 may have a longitudinal axis 358. These axes 356, 358 may, in some embodiments, also be the longitudinal axes of the corresponding openings 334, 352, respectively. Axes 356, 358 may be separated a distance 361, indicated in FIG. 11. Distance 361 may vary depending on the size of the implant but should be small enough to provide easy visualization for the surgeon during fluoroscopy. In some embodiments, distance 361 is not greater than 1.0 inches. In other embodiments, distance 361 is not greater than 0.8 inches. In other embodiments, distance 361 is not greater than 0.6 inches. In other embodiments, distance 361 is not greater than 0.4 inches. In other embodiments, distance 361 is not greater than 0.2 inches.

Still referring to FIGS. 5 and 10-17 but especially FIG. 14, pin 332 may have an axially upper most point 360 and pin 350 may have an axially upper most point 362. It should be noted that "upper most" assumes that the implant is positioned as shown in FIGS. 13-17. As well understood by persons of skill in the art, the actual position of the implant at any particular time will depend on the position of the patient and/or the desired position of the implant for the surgeon. Thus, in properly interpreting "axially upper most" it must be understood that the implant must be oriented as shown in FIGS. 13-17. A plane that simultaneously intersects the point 360 and is perpendicular to the pivot axis 320 when the implant is in the non-deployed condition is given reference 364 in FIG. 14. A plane that simultaneously intersects the point 362 and is perpendicular to the pivot axis 320 when the implant is in the non-deployed condition is given reference 366. A plane that simultaneously intersects the point 360 and is perpendicular to the pivot axis 320 when the implant is in the deployed condition is given reference 368 in FIG. 17. A plane that simultaneously intersects the point 362 and is perpendicular to the pivot axis 320 when the implant is in the deployed condition is given reference 370. Because both pins are fluoroscopically detectable as distinct from the first and second members 306, 308, the surgeon can easily see the relative positions of the pins 332, 350 using fluoroscopic imagery and thus easily determine the condition of the implant. To further assist the surgeon, in one embodiment the planes 364, 366 are coplanar, or near coplanar. In one specific embodiment, the axial distance between plane 364 and plane 366 is 0.2 inches or less. In another embodiment, the axial distance between plane 364 and plane 366 is 0.1 inches or less. In one specific embodiment, the axial distance between plane 368 and plane 370, distance 372, is 0.2 inches or more. In another embodiment, distance 372 is 0.3 inches or more. Thus, using fluoroscopy, the surgeon can quickly and easily determine the condition of the implant (non-deployed or deployed).

With reference now to FIGS. 5 and 10-20, the previously noted pin longitudinal axes can also be used to make it easy for the surgeon to determine when the implant 300 is unlocked by pin separation. Specifically, as shown in FIG. 20, pin portion 346 will maintain longitudinal axis 356 (since it remains in opening 334) and pin 350 will maintain longitudinal axis 358 (since it remains in opening 352). Pin portion 344, however, will have a longitudinal axis 374 (also parallel to the pivot axis 320) that is non-collinear with either of axis 356 or axis 358. Thus, using fluoroscopy, the surgeon can quickly and easily determine that pin 332 has separated and thus that the implant is unlocked. With this knowledge, the surgeon can pivot the first member 306 relative to the second member 308 sufficient to reduce the footprint so the implant 300 can be removed.

With reference now to FIGS. 10-20, pins 332, 350 can be sized and shaped and can be formed of any material chosen with the sound judgement of a person of skill in the art. As noted above, the pins 332, 350 may be formed of a material that makes them fluoroscopically detectable as distinct from the first and second implant members 306, 308. In one non-limiting embodiment, the pins 332, 350 are made of tantalum. The pins 332, 350, in the embodiments shown, are generally cylindrical in shape. Their diameters and axial heights can be chosen to match the size and use of the particular implant. In one embodiment, pins 332, 350 are similar in size and shape. In a more specific embodiment, shown, pins 332, 350 have the same size and shape. This simplifies implant construction.

Figure 21:
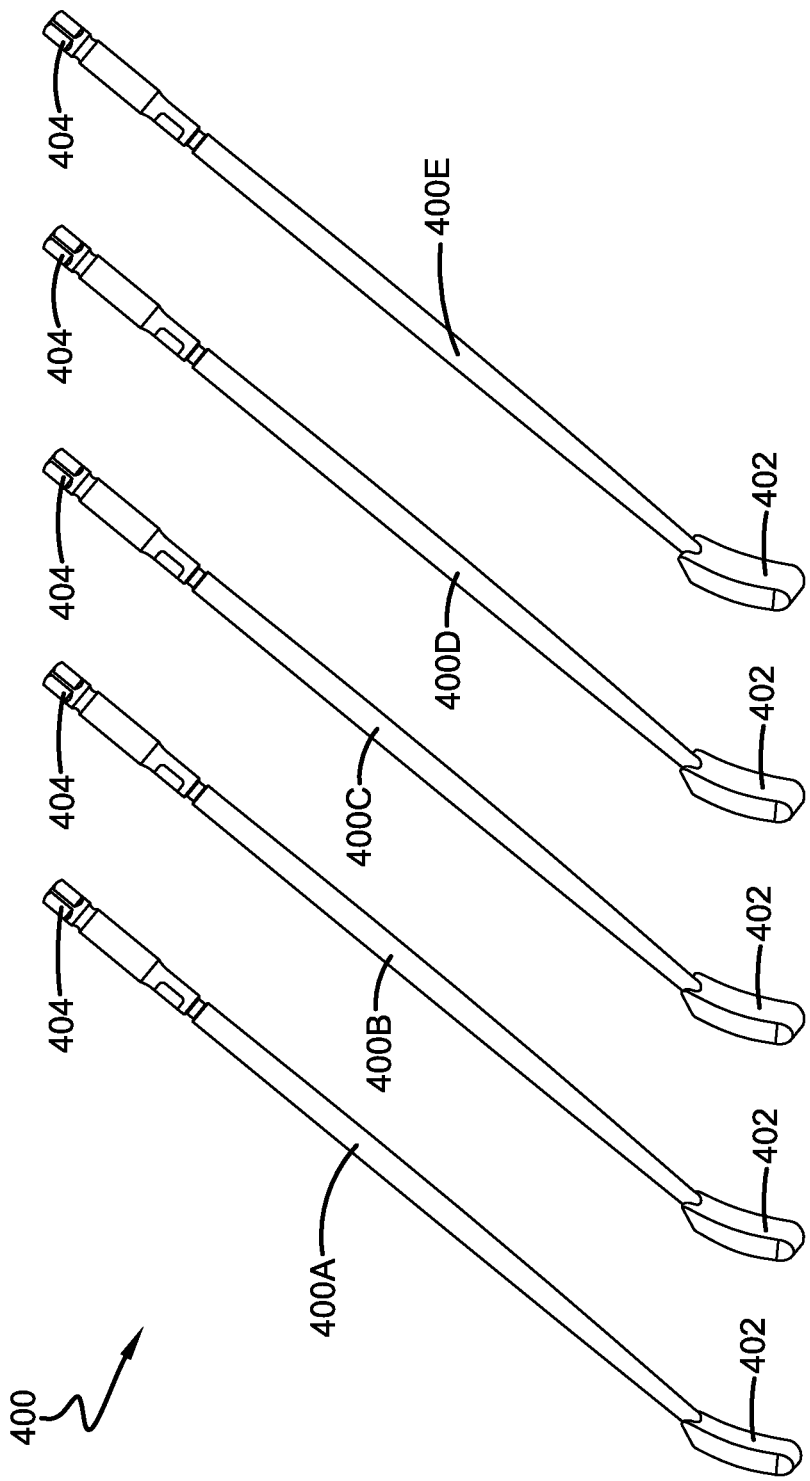
FIG. 21 shows several different sized trials.
Figure 23:
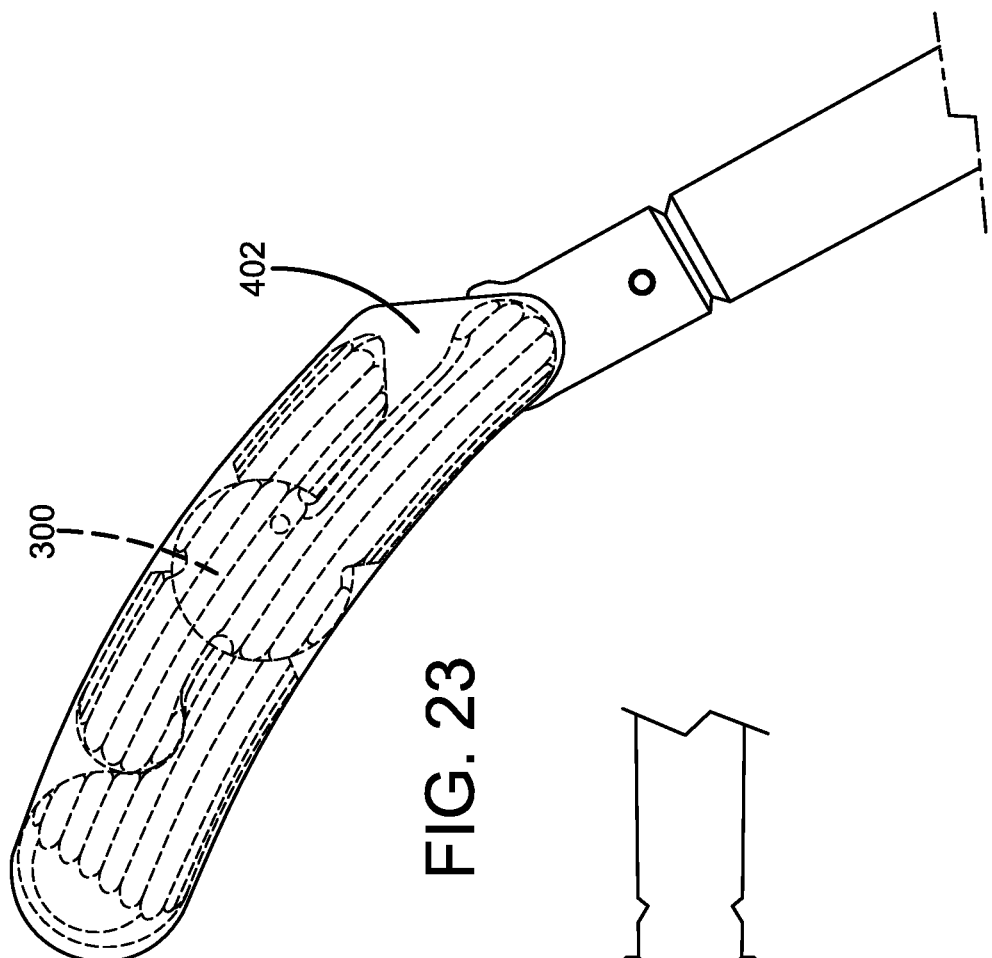
FIG. 23 is a top view illustrating how a trial's implant facsimile is the same size as a particular implant.
Figure 22:
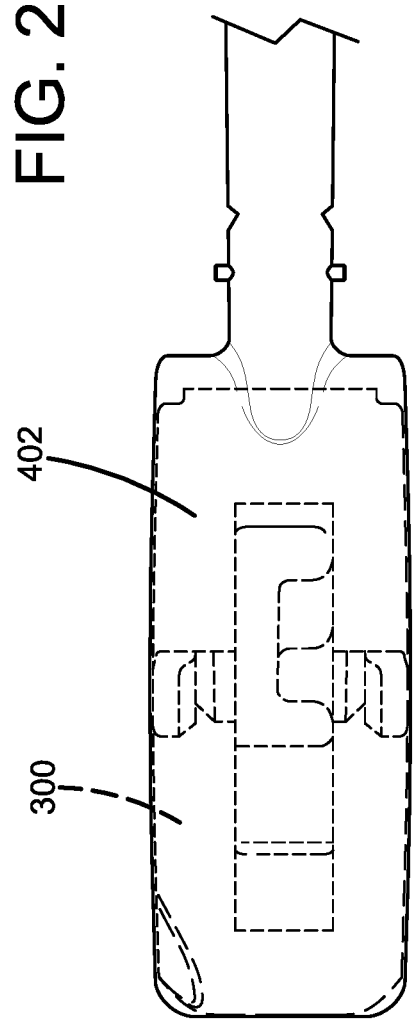
FIG. 22 is a side view illustrating how a trial's implant facsimile is the same size as a particular implant.

With reference now to FIGS. 21-25, the surgical instrumentation according to some aspects of the present teaching may include one or more trials used to determine what size of implant will be required for a particular patient. FIG. 21 shows five different trials 400, each given a lettered suffix A through E. Each trial 400 may have a longitudinally extending shaft with an implant facsimile 402 at its distal end and an attachment surface 404 at its proximal end. FIGS. 22-23 illustrate how each implant facsimile 402 may have dimensions corresponding to the dimensions of a particular non-deployed implant 300. The five trials 400 shown in FIG. 4 (400A-400E) may be the same except that the implant facsimiles 402 have different dimensions corresponding to different implant dimensions, as shown in FIGS. 7-9. It should be understood that while only five sized trials 400 are shown, any number of trials as chosen by a person of skill in the art may be provided for the surgeon.

Figure 25:
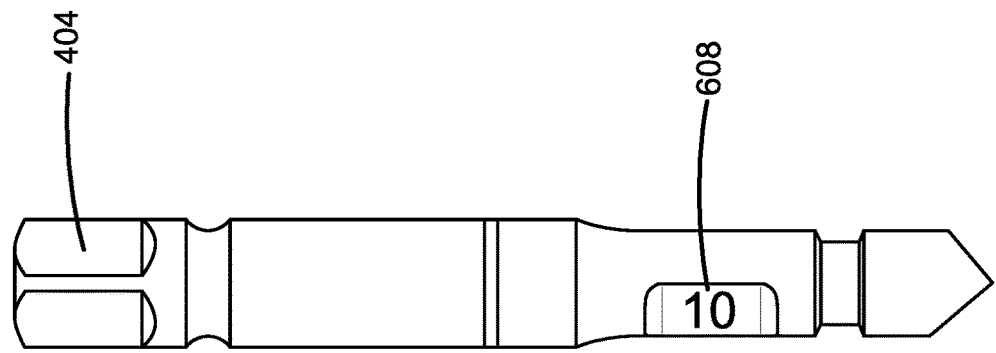
FIG. 25 is a side close-up view of a proximal end of a trial.
Figure 24:
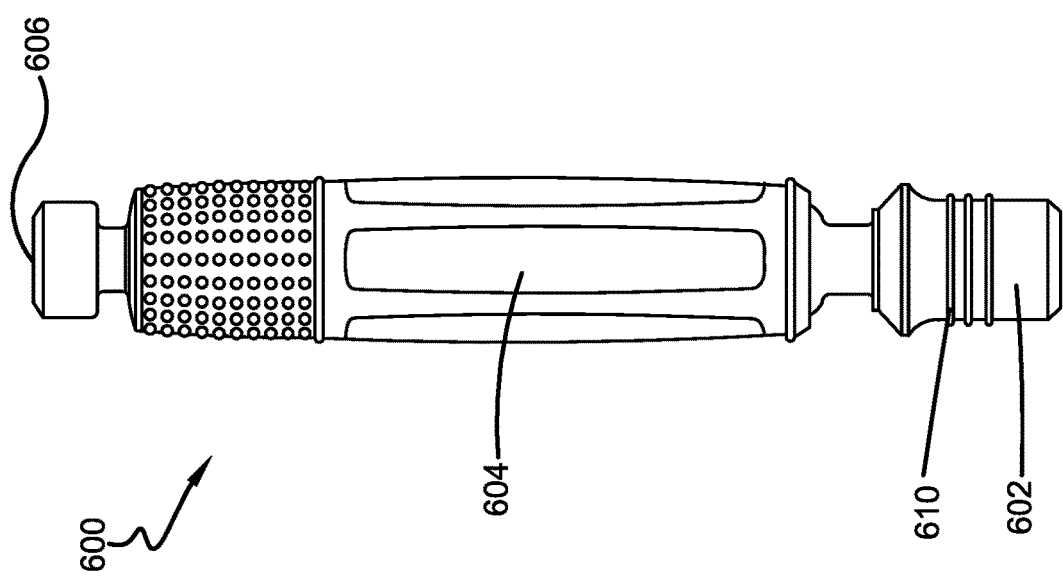
FIG. 24 is a side view of a handle designed to attach to different sized trials.
Figure 26:
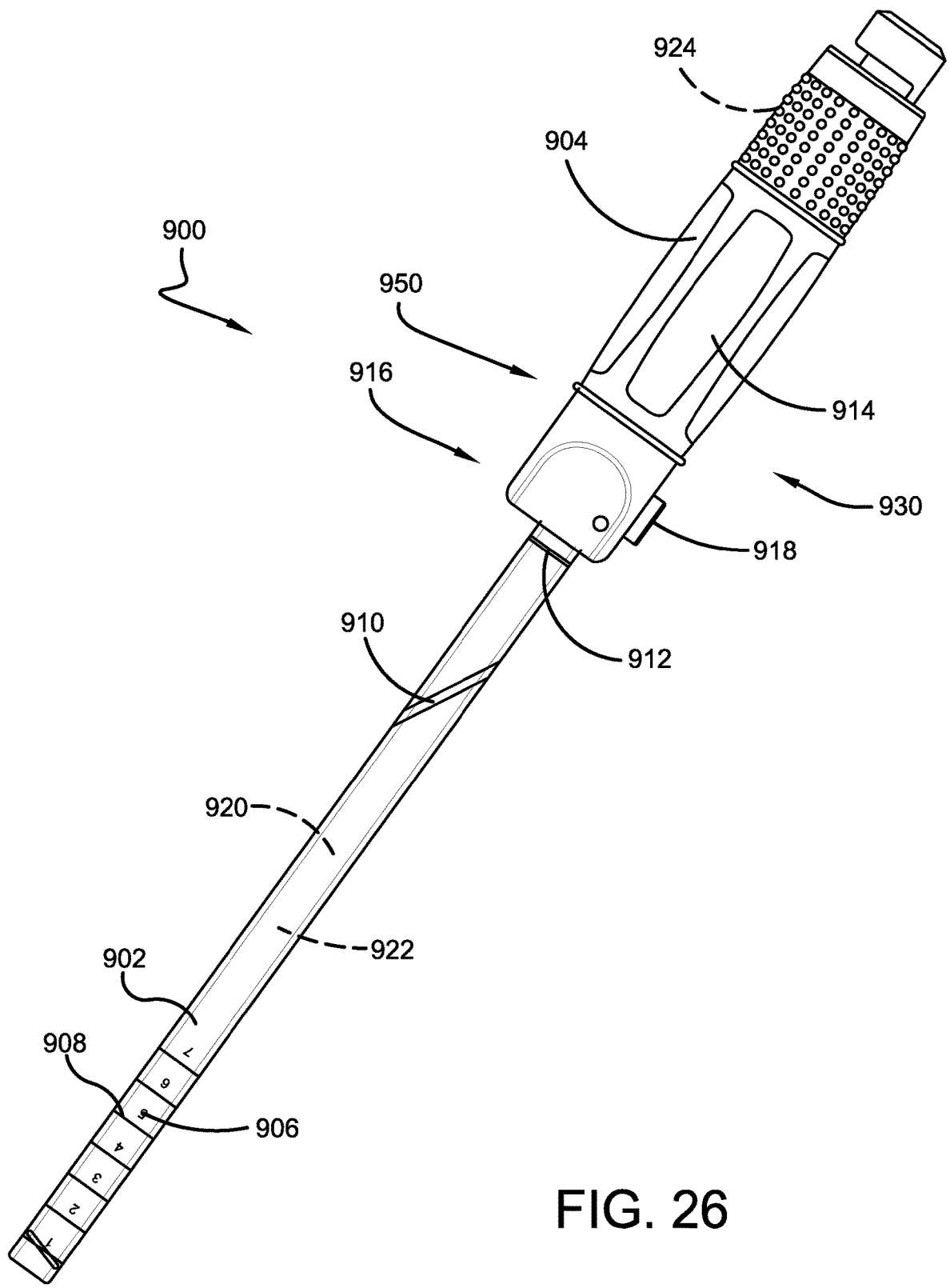
FIG. 26 is a side view of an inserter.
Figure 27:
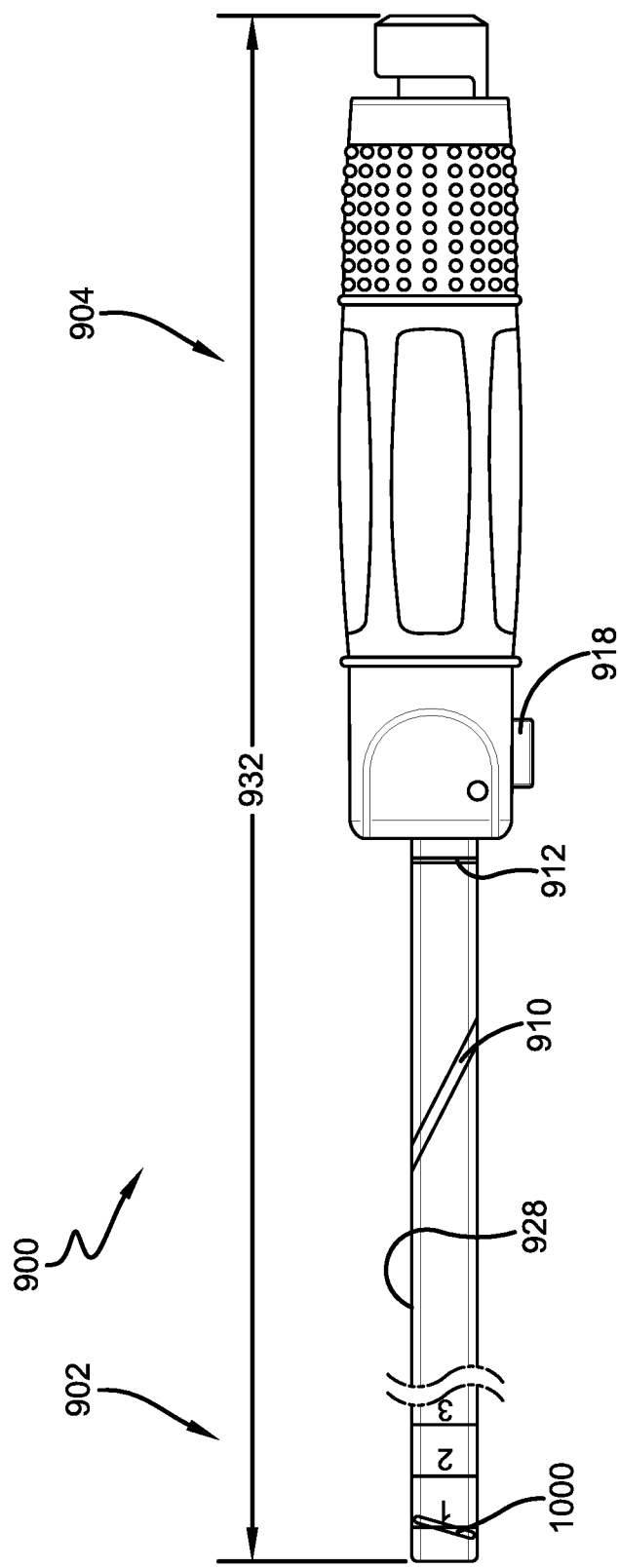
FIG. 27 is a side view of an inserter but with some portion removed for clarity.
Figure 28:
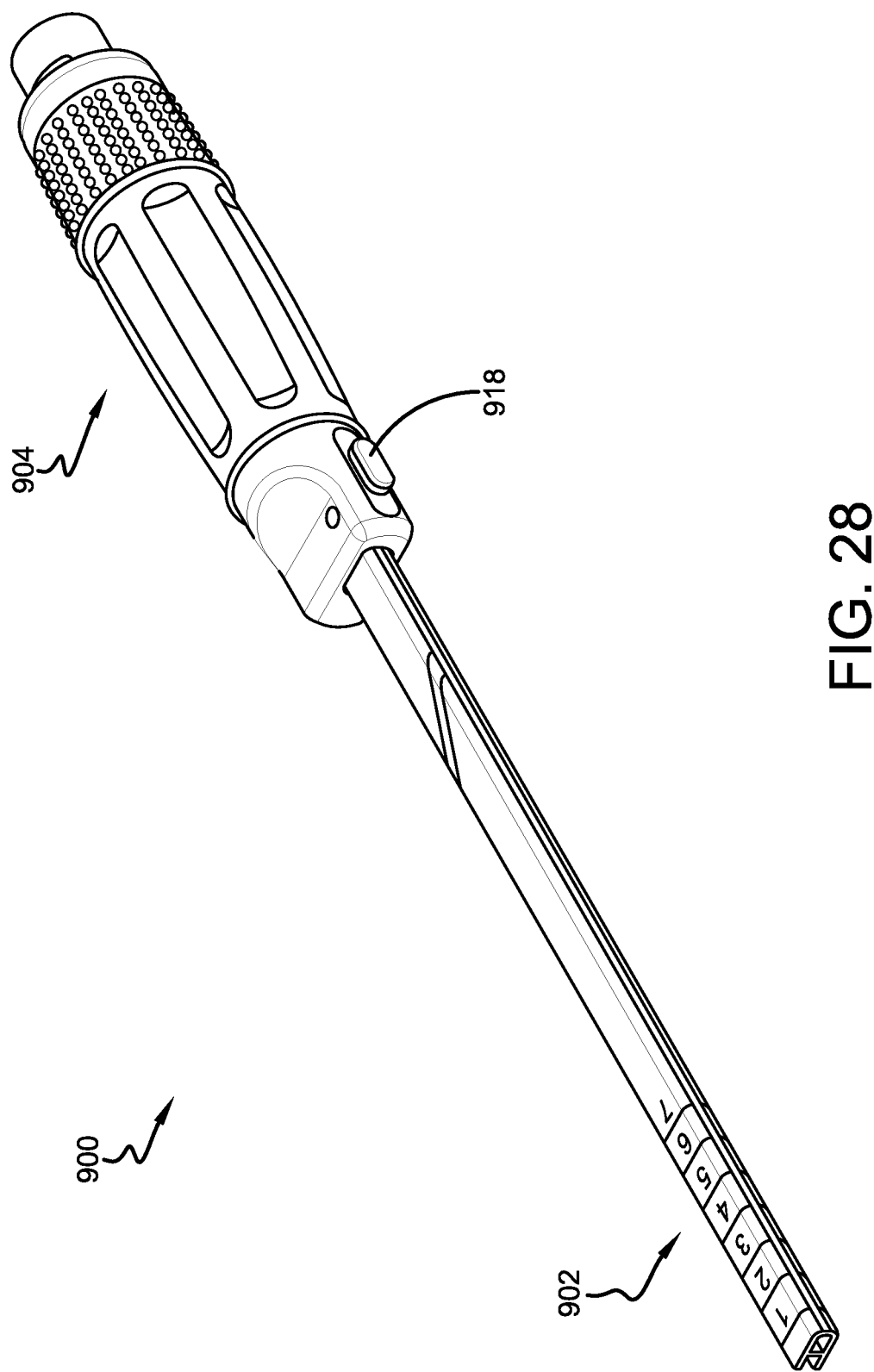
FIG. 28 is a side perspective view of an inserter.

FIG. 24 shows a handle 600 which may be used with any of the trials 400 shown in FIG. 21. The handle 600 may include a distal end with a trial receiving surface 602, a midsection with a grip surface 604, and a proximal end with a force receiving surface 606. The trial receiving surface 602 may be designed to engage with the attachment surface 404 of each trial 400. FIG. 25 shows the proximal end of a trial where the attachment surface 404 may be seen in more detail. The engagement between the trial receiving surface 602 and the attachment surface 404 can be any chosen with the sound judgment of a person of skill in the art. For the example shown, the trial receiving surface 602 comprises an opening shaped to receive the shape of the attachment surface 404. The attachment surface 404 may have an outer surface sized to match the inner surface of the opening defining the receiving surface 602. In this way, the surgeon has a socket style, "quick connect" attachment so that various trials 400 can be easily attached and detached from the handle 600 as the appropriate implant size is determined. The distal end may include a textured surface 610 to provide a tactile response to the surgeon and to prevent slippage.

With reference now to FIGS. 21-25, each trial 400 may include an information surface 608 where information concerning the trial 400 can be provided for the surgeon. The information surface 608 may, for example, include information regarding the size of the implant facsimile at the distal end of that particular trial 400. The grip surface 604 of the handle 600 may be used by the surgeon when gripping the handle 600 and when using the handle along with the trial 400 that is attached to the handle 600. The force receiving surface 606 may be used when the surgeon determines a compression force should be supplied to the handle 600; such as when positioning the implant facsimile within the vertebral space to determine implant size.

With reference now to FIGS. 26-30, the surgical instrumentation according to some aspects of the present teaching may include an inserter 900 having a distal end portion 902, a proximal end portion 904 and, a longitudinal length 932. The outer surface of the proximal end portion 904 may serve as a handle for the surgeon and may include a grip surface 914 to improve this function. The outer surface of the distal end portion 902 may include markings to assist the surgeon in properly positioning the inserter 900 during surgery. The markings may include numerals 906 and/or lines 908 that indicate measurements (such as inches or centimeters) so that the surgeon can easily see how the inserter 900 is being positioned with respect to the patient. The markings may include lines 910 and 1000 (see FIGS. 26, 27 and 29) to indicate proper insertion angle 1002, shown in FIG. 29. In one example, the proper insertion angle 1002 is 25 degrees with respect to a plain 1004 that intersects the middle of the patient's spinal segment and is perpendicular to the operating table. Lines 910, 1000 may be predetermined to be parallel and perpendicular, respectively, with respect to the plain 1004 when the correct insertion angle 1002 is achieved to assure the surgeon that alignment is correct. The markings may include a line 912 that is used for implant deployment as will be discussed further below.

With reference now to FIGS. 26-33, the inserter 900 may be a tube having internal channels used to receive later to be described surgical instruments. In some embodiments, seen best in FIGS. 31 and 33, the inserter 900 has two distinct longitudinally extending channels 920, 922 that extend for at least most of the longitudinal length 932 to openings at the proximal and distal ends of the inserter 900. The channels 920, 922 may be separated by a wall 924 that may serve as a barrier between the channels 920, 922 preventing surgical instruments received in one channel from contacting surgical instruments simultaneously received in the other channel. A groove 928 may extend longitudinally in a wall of the distal end portion 902, providing an opening to the channel 920. The inserter 900 may be formed in any manner chosen with the sound judgment of a person of skill in the art. For the embodiments shown in FIG. 32, a grip 934 receives shaft 936 and an impact cap 938 is inserted within the grip 934. A rotational force converter 930 (FIG. 33), used as discussed below, may be positioned within the proximal end of channel 922, within the proximal end of the impact cap 938 in the embodiment shown.

Figure 33:
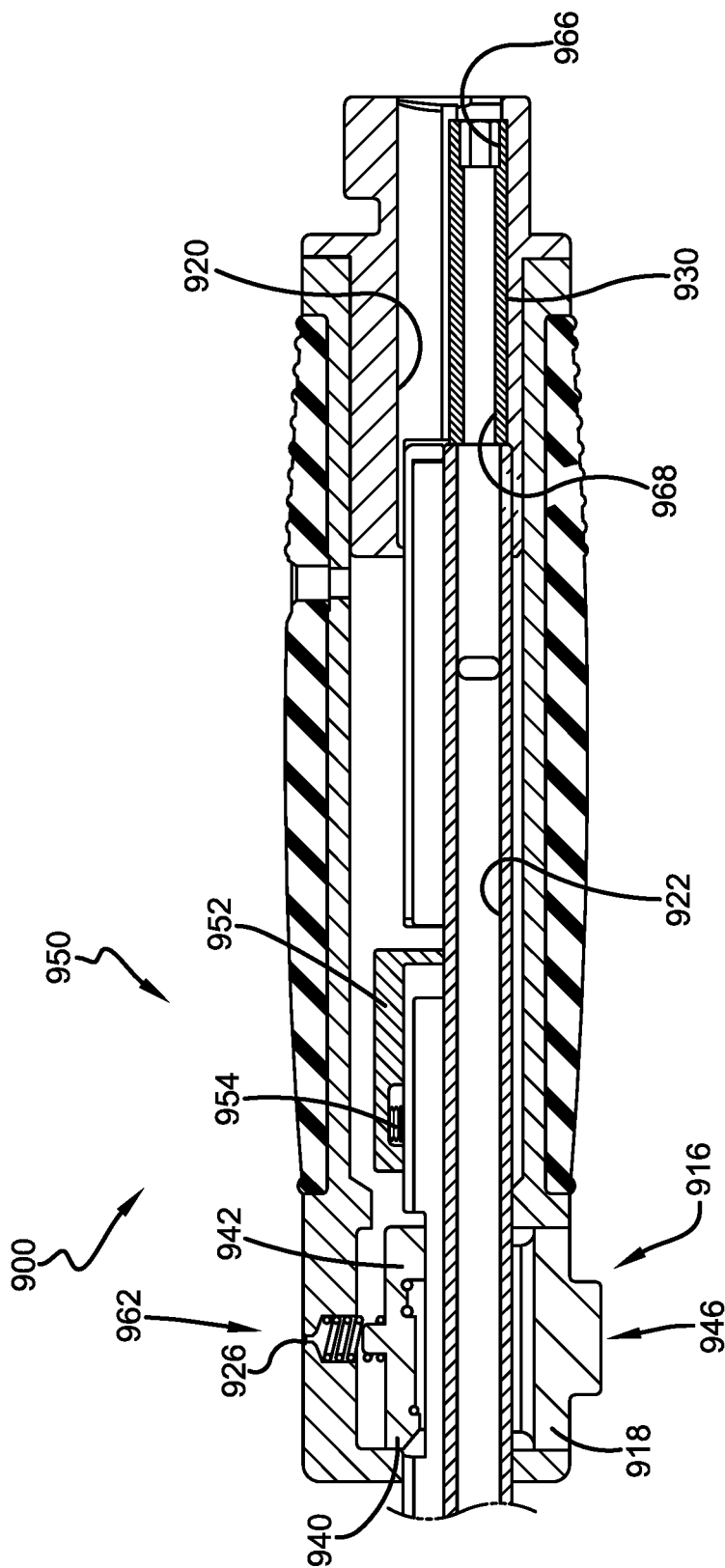
FIG. 33 is a side sectional view of a portion of an inserter.
Figure 34:
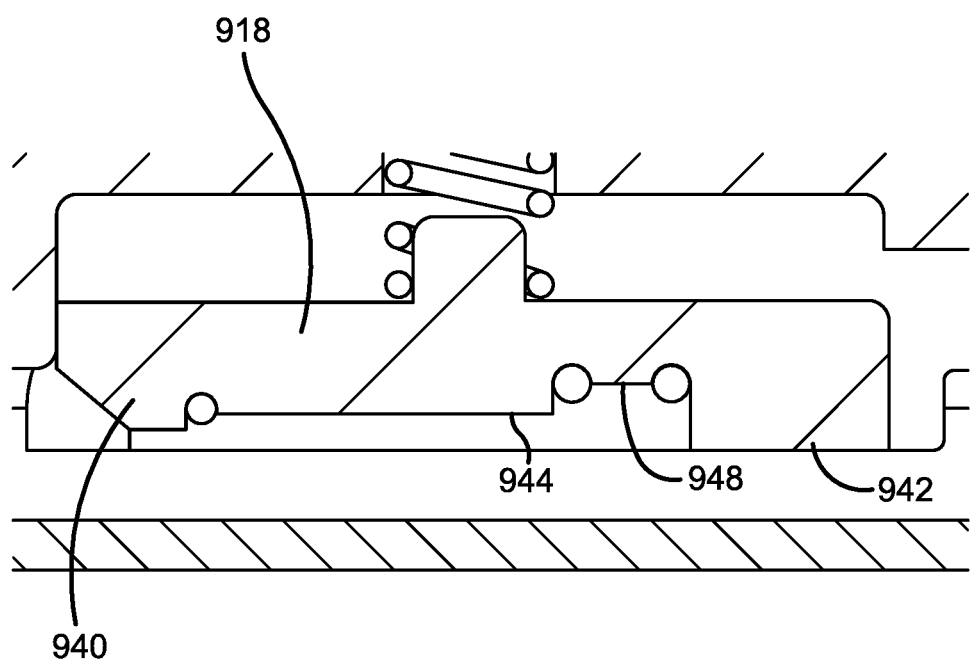
FIG. 34 is a close-up view of the movable button shown in FIG. 33.
Figure 35:
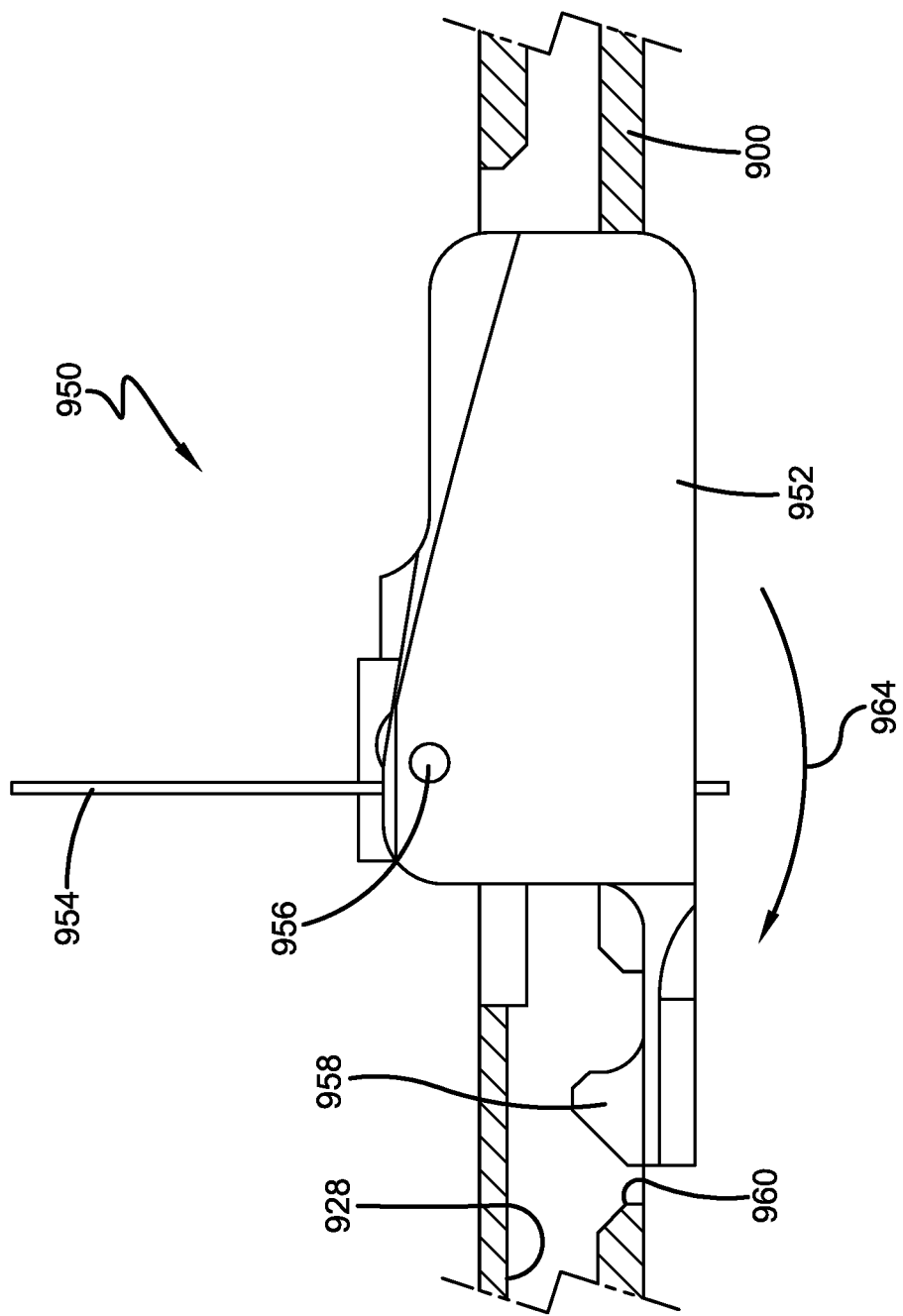
FIG. 35 is a top view of a latch mechanism.
Figure 36:
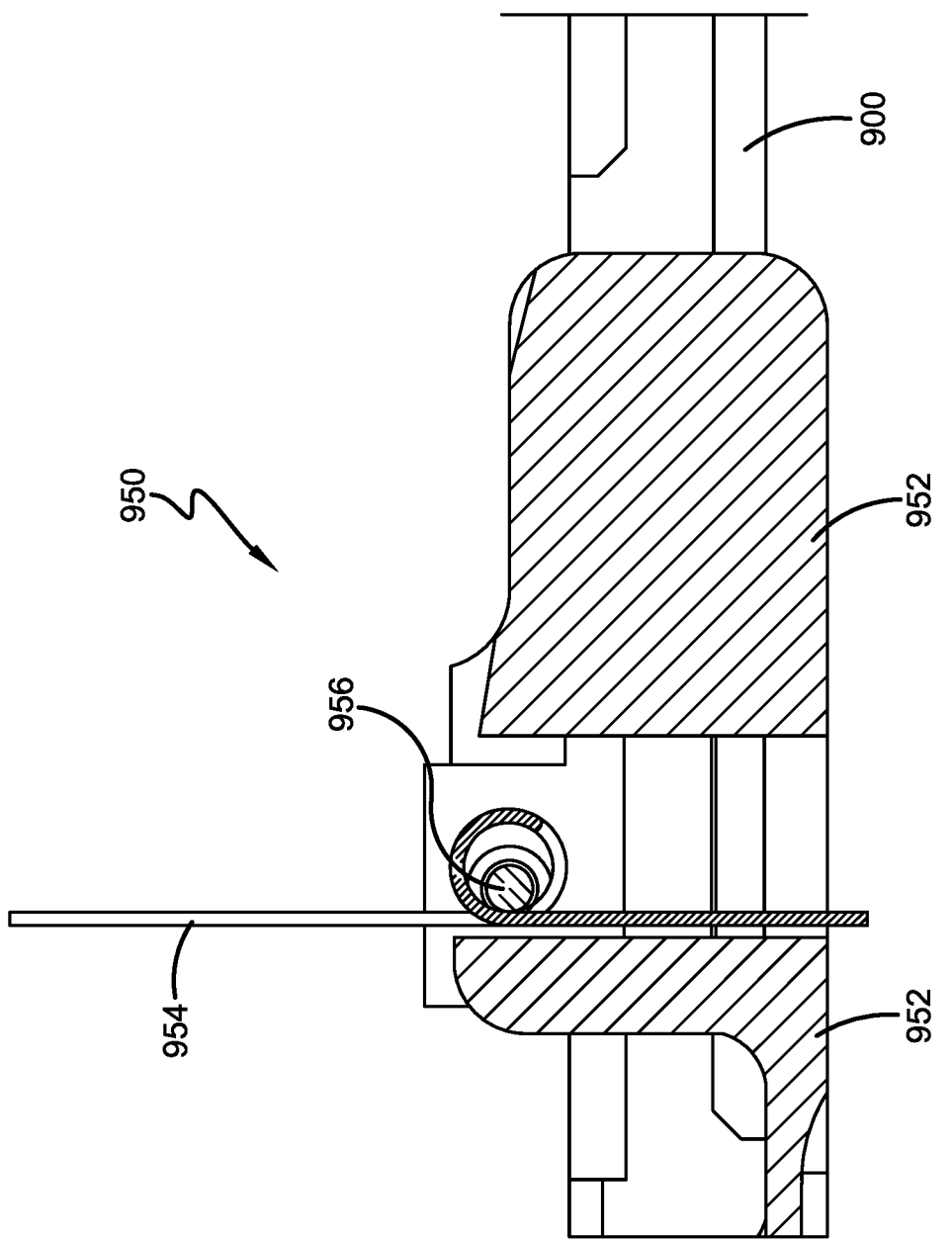
FIG. 36 is a view similar to that shown in FIG. 35 but with portions removed for clarity.
Figure 37:
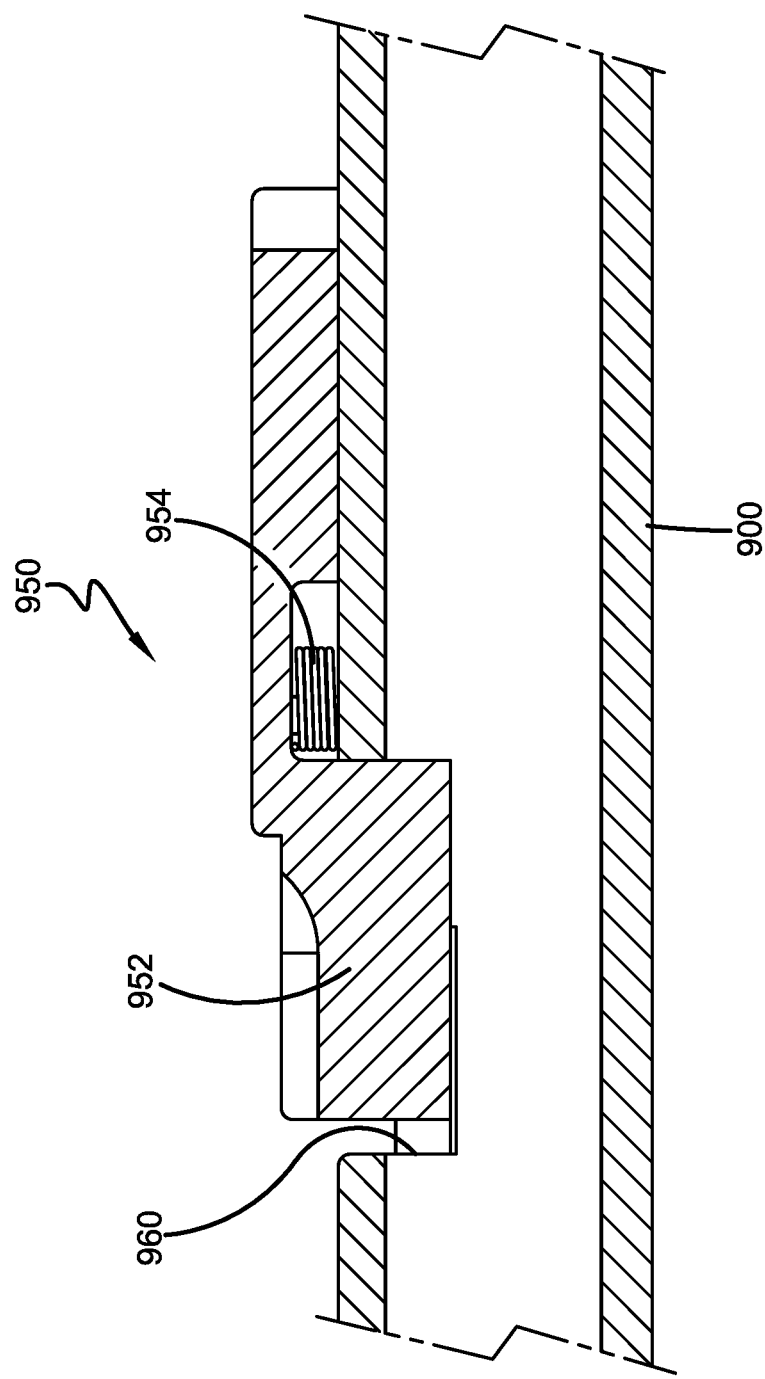
FIG. 37 is a side view of the latch mechanism shown in FIG. 35.
Figure 38:
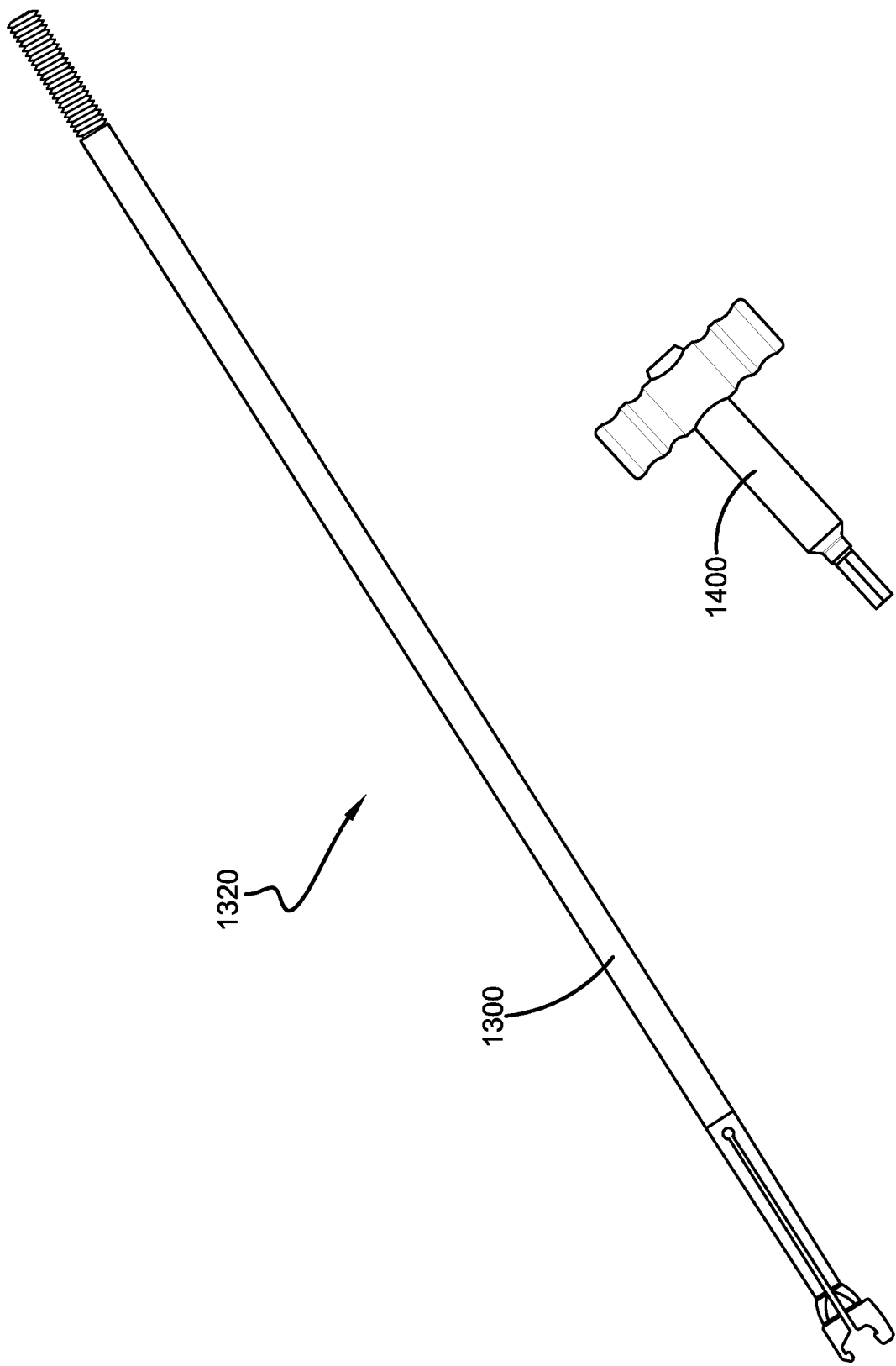
FIG. 38 shows an implant gripping mechanism.
Figure 39:
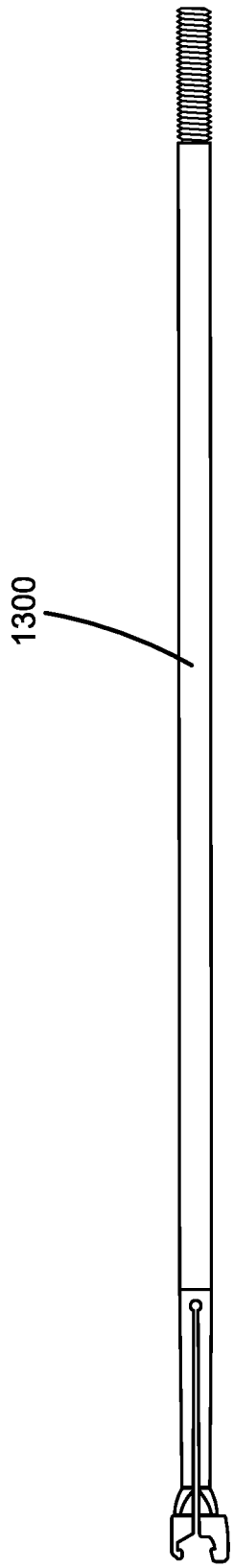
FIG. 39 is a side view of a gripping device.
Figure 41:
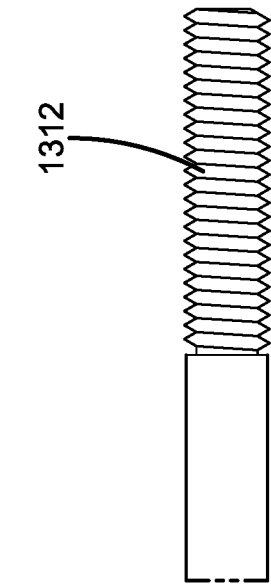
FIG. 41 is a close-up view of the proximal end of the gripping device shown in FIG. 39.
Figure 40:
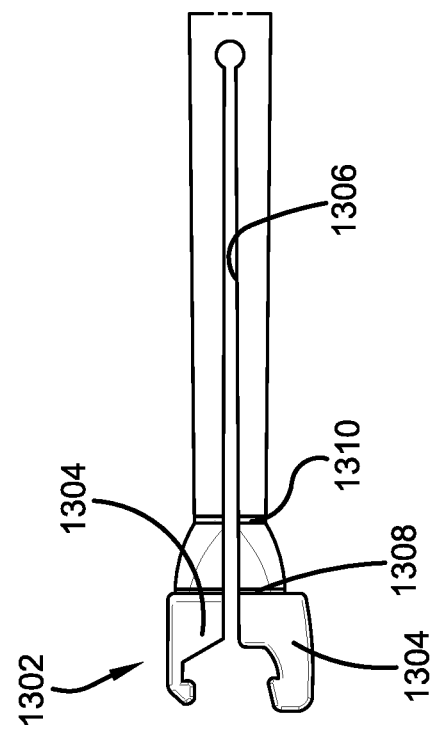
FIG. 40 is a close-up view of the distal end of the gripping device shown in FIG. 39.
Figure 42:
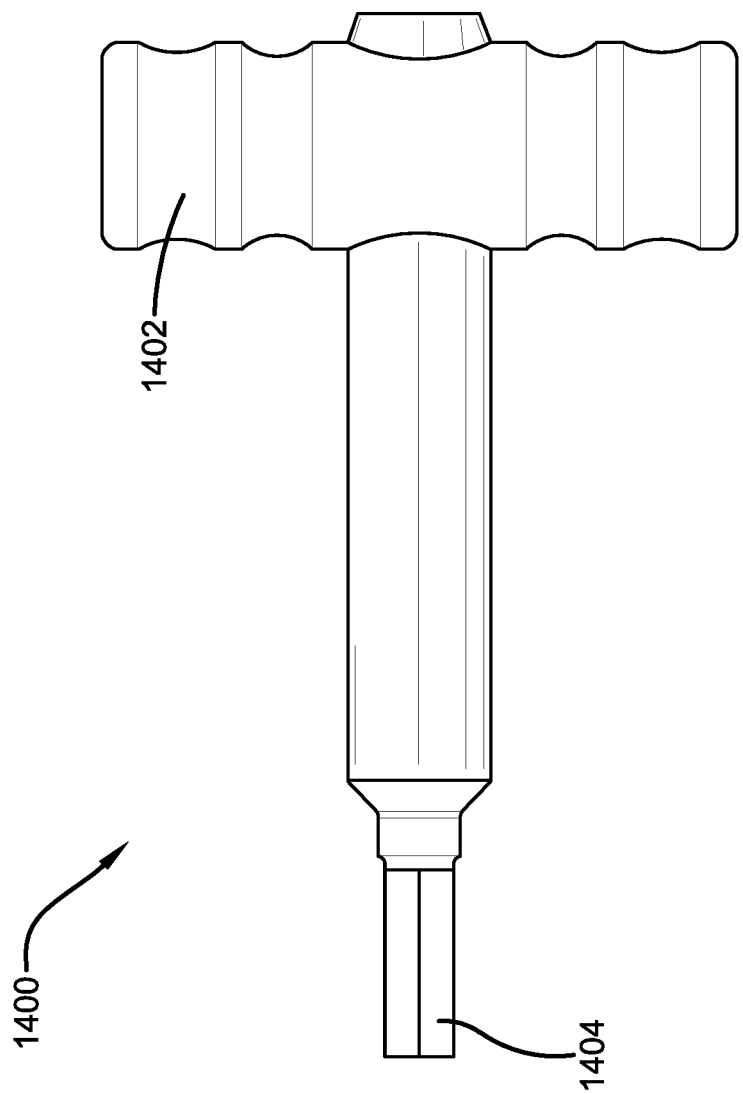
FIG. 42 is a side view of tool.

With reference now to FIGS. 26-28, 30 and 32-34, the inserter 900 may be equipped with one, and in some embodiments two, latch mechanisms that is/are used to engage surgical instruments to each other and/or to the inserter 900. Latch mechanism 916 may include a movable object 918 and a biasing device 926 that applies a biasing force to the movable object 918. In one embodiment, shown, the biasing device 926 is a compression spring. The movable object 918 may be a manually movable button 918, as shown. Button 918 may have, as shown in FIGS. 33-34, one side with a pair of tabs 940, 942 separated by a groove 944 and a second side with a contact surface 946. The groove 944 may have a cut-out portion 948. Latch mechanism 916 may be positioned within opening 948 (FIG. 32) in the inserter 900 with the biasing device 926 biasing the movable object 918 in direction 962 (FIG. 33) to bias contact surface 918 to extend out of the inserter 900, as shown.

With reference now to FIGS. 26 and 32-37, a latch mechanism 950 may include a movable object 952 and a biasing device 954 that applies a biasing force to the movable object 952. In one embodiment, shown, the biasing device 954 is a torsion spring. The movable object 952 may pivot about pin 956 and may have a tab 958. Latch mechanism 950 may be positioned on the inserter 900 with the biasing device 954 biasing the movable object 952 in direction 964 about pin 956 to bias tab 958 to extend into inserter opening 960, as shown. Latch mechanism 950 may be positioned within grip 934 proximal to latch mechanism 916, as shown. In embodiments where both latch mechanisms 916, 950 are used, it should be noted that the corresponding biasing forces bias tabs 940, 942 in a first direction (downward in FIGS. 27, 33 and into the page in FIG. 35) and bias tab 958 in a second direction (into the page in FIGS. 27, 33, 37 and upward in FIG. 35) that is at a right angle with respect to the first direction. As a result, the forces applied to the surgical instruments by the latch mechanisms are complementary.

With reference now to FIGS. 38-42, the surgical instrumentation according to some aspects of the present teaching of this invention may include an implant gripping mechanism 1320 used to grip or hold the implant and to release the implant. The gripping mechanism 1320 may include, in some embodiments, a gripping device 1300, a tool 1400 and the previously mentioned rotational force converter 930 (shown in FIG. 33). The gripping device 1300 may be an axle that extends longitudinally, as shown, and may have a distal end with a gripper 1302. The gripper 1302 may include a pair of opposing jaws 1304, 1304. The jaws 1304, 1304 may be designed to grip a portion of the implant and may be separated by a slot 1306 that extends proximally along the axle, as shown. A pair of markings 1308, 1310 may be positioned along the longitudinal axis of the gripping device 1300, as shown. The proximal end of the gripping device 1300 may include a connection surface 1312. According to some aspects of the present teaching of this invention, the connection surface 1312 may include threads on the outer surface of the gripping device 1300, as shown.

Figure 43:
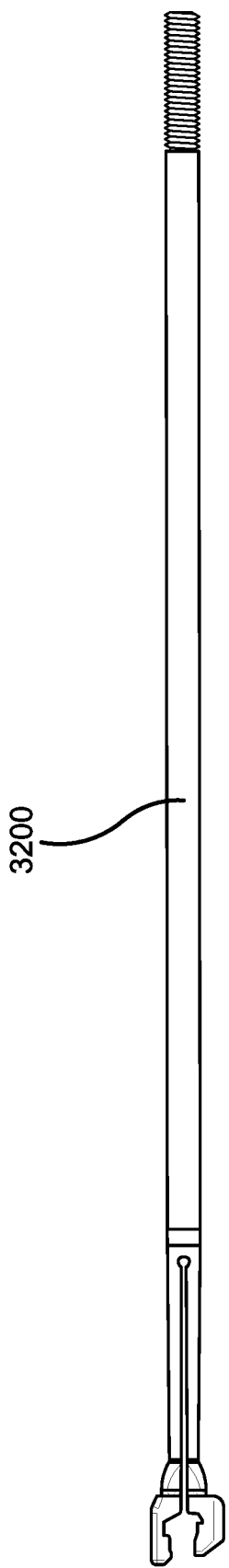
FIG. 43 is a side view of a gripping device 3200.
Figure 45:
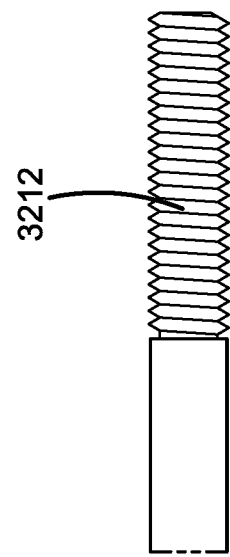
FIG. 45 is a close-up view of the proximal end of the gripping device shown in FIG. 43.
Figure 44:
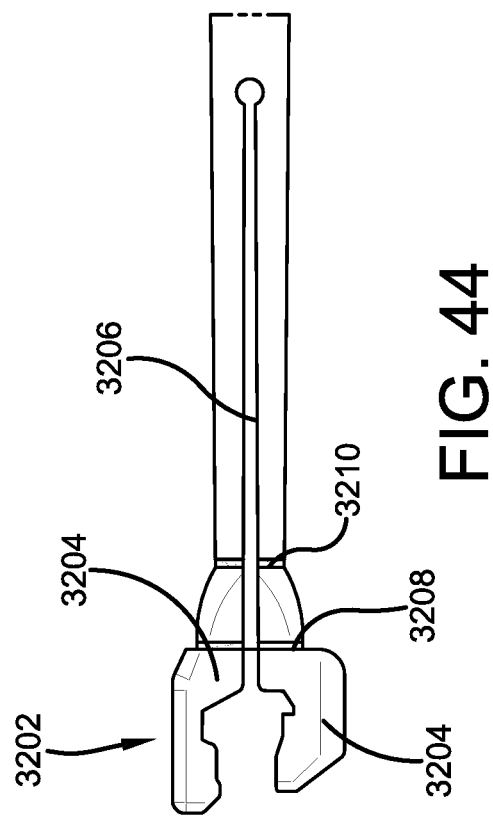
FIG. 44 is a close-up view of the distal end of the gripping device shown in FIG. 43.

With reference now to FIGS. 43-45, the surgical instrumentation according to some aspects of the present teaching of this invention may include an alternate gripping device 3200. Gripping device 3200 may, in some circumstances, be better suited for use in removing an implant from the vertebral space than gripping device 1300 described above. The gripping device 3200 may be an axle that extends longitudinally, as shown, and may have a distal end with a gripper 3202. The gripper 3202 may include a pair of opposing jaws 3204, 3204. The jaws 3204, 3204 may be designed to grip a portion of the implant and may be separated by a slot 3206 that extends proximally along the axle, as shown. The jaws 3204, 3204 may have a different shape than the jaws 1304, 1304 of the gripping device 1300 (FIG. 40) and may provide a wider mouth to make re-engagement to the implant in a constricted space (such as a vertebral space) easier for the surgeon. A pair of markings 3208, 3210 may be positioned along the longitudinal axis of the gripper 3200, as shown. The proximal end of the gripper 3200 may include a connection surface 3212. According to some aspects of the present teaching of this invention, the connection surface 3212 may include threads on the outer surface of the remover collet 3200, as shown.

With reference now to FIGS. 33 and 38-45, the tool 1400 may be used to adjust the gripping device 1300 via the rotational force converter 930. The tool 1400 may have a proximal end with a handle 1402 used by the surgeon when using the tool and a distal end with a connection surface 1404. The rotational force converter 930 may have a proximal end with a connection surface 966 designed to engage the connection surface 1404 of the tool 1400 and a distal end with a connection surface 968 designed to engage the connection surface 1312 of the gripping mechanism 1300. In one non-limiting embodiment, shown, the connection surface 1404 of the tool 1400 is a male hex wrench head that is received in a female hex wrench opening formed in the connection surface 966 of the rotational force converter 930 and the threaded connection surfaces 1312, 3212 of the gripping devices 1300, 3200 are received in a matching threaded opening formed in the connection surface 968 of the rotational force converter 930.

Figure 46:
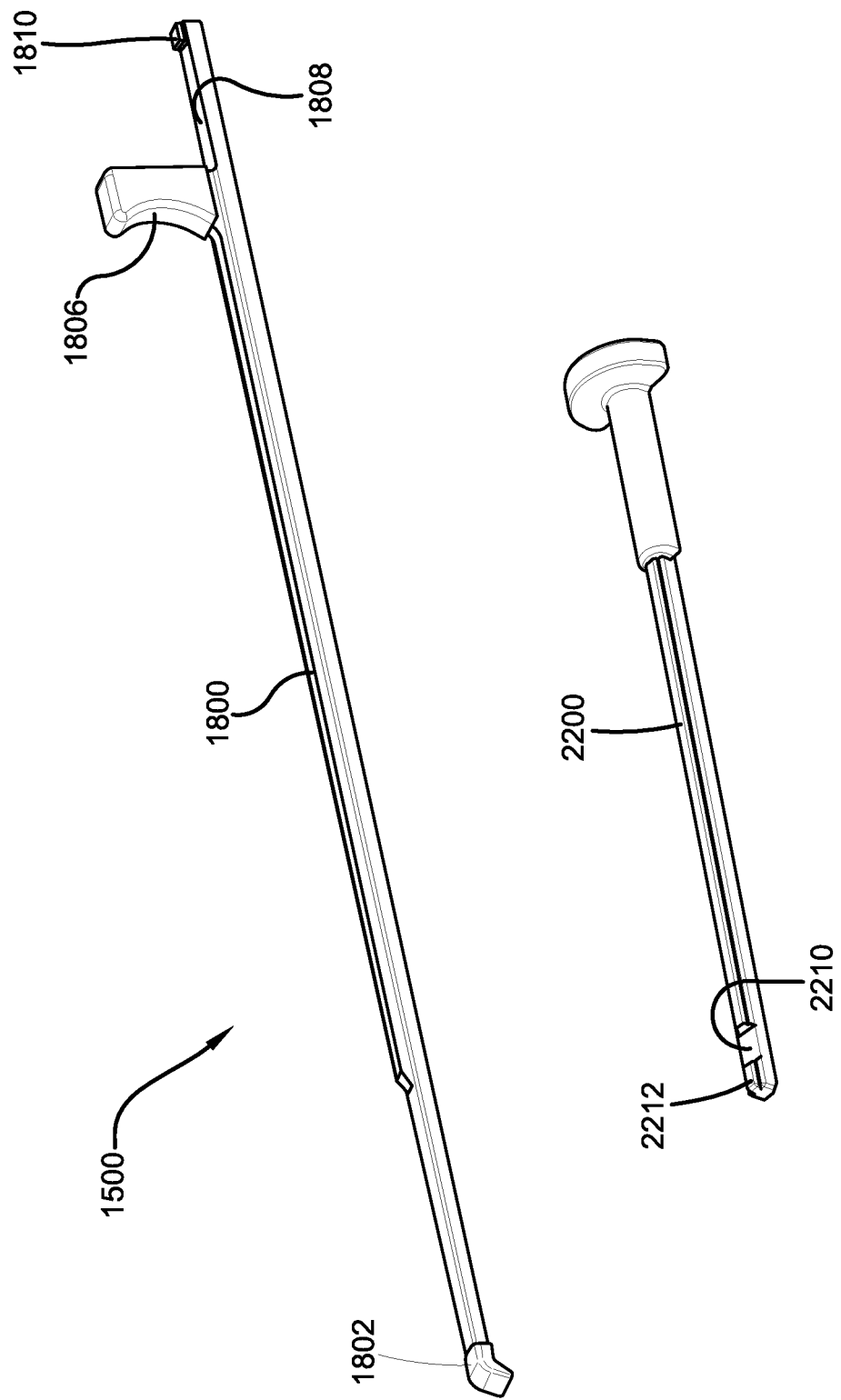
FIG. 46 shows an implant deployment mechanism.
Figure 47:
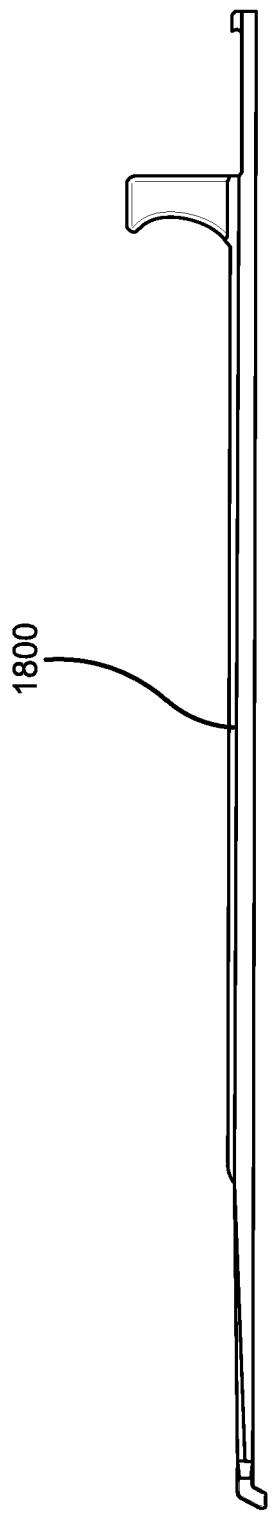
FIG. 47 is a side view of an inserter tamp.
Figure 49:
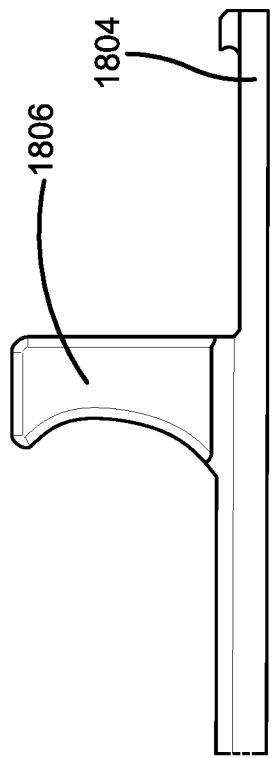
FIG. 49 is a close-up view of the proximal end of the inserter tamp shown in FIG. 47.
Figure 48:
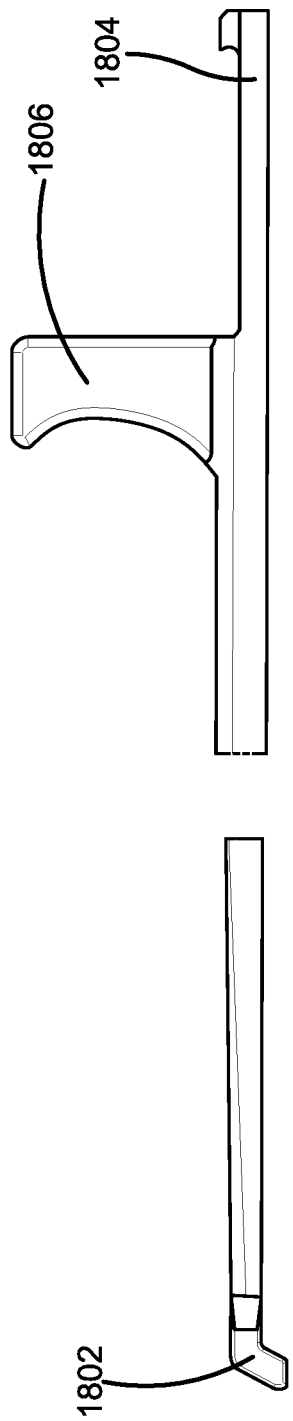
FIG. 48 is a close-up view of the distal end of the inserter tamp shown in FIG. 47.
Figure 50:
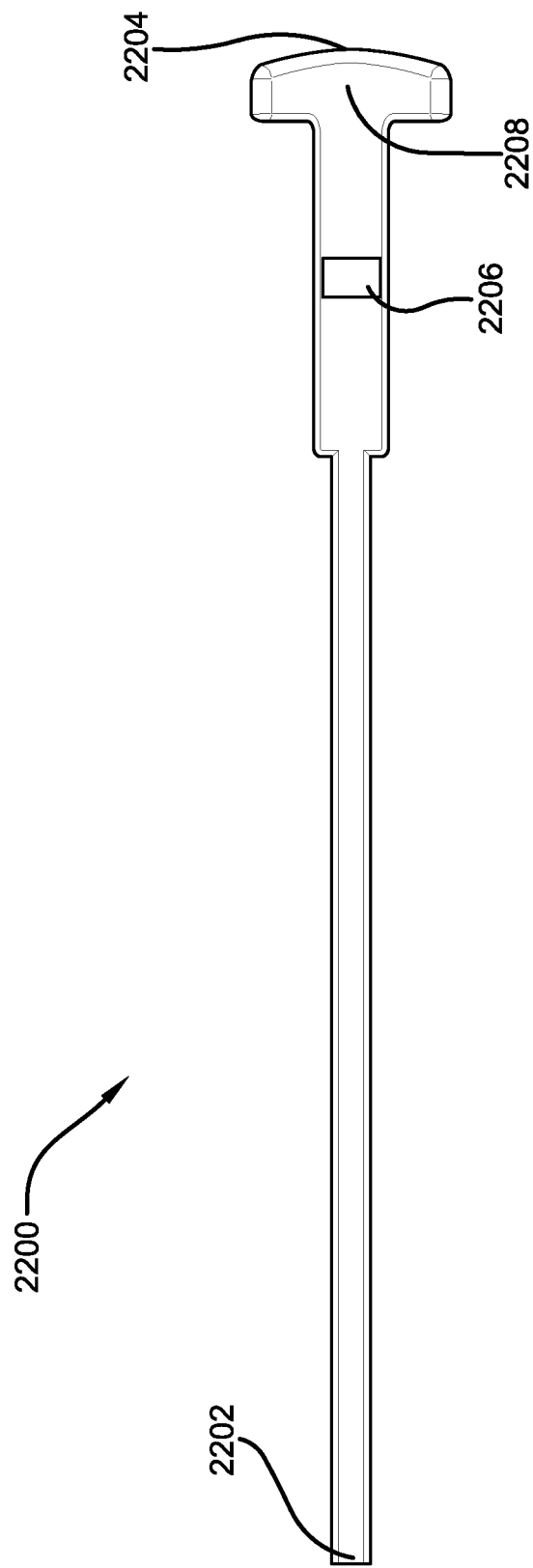
FIG. 50 is a side view of an impactor.

With reference now to FIGS. 46-50, the surgical instrumentation according to some aspects of the present teaching of this invention may include an implant deployment mechanism 1500 used to deploy the implant. The implant deployment mechanism 1500 may include, in some embodiments, an inserter tamp 1800 and an impactor 2200. The inserter tamp 1800 may extend longitudinally, as shown, and may include a distal end with a contact surface 1802. The contact surface 1802 may extend downwardly, as shown in FIGS. 46 and 48. The proximal end of the inserter tamp 1800 may include a connection surface 1804. The connection surface 1804 may include a groove 1808 extending to a tab 1810. The tab 1810 may extend upwardly, as shown in FIGS. 46 and 49. A trigger 1806 may extend upwardly, as shown. Multiple sizes of inserter tamps may be provided to correspond to multiple implant sizes. Markings may be provided on the trigger 1806, as shown, to indicate the size of the inserter tamp. The impactor 2200 may extend longitudinally, as shown, and may include a distal end with a connection surface 2202 and a proximal end with a contact surface 2204. The connection surface 2202 may include a groove 2210 extending to a tab 2212. The tab 2212 may extend upwardly, as shown in FIG. 46. The impactor 2200 may include markings 2206 and 2208. The marking 2208 may indicate the size of the impactor so that the surgeon can choose the impactor corresponding to the implant to be deployed.

Figure 51:
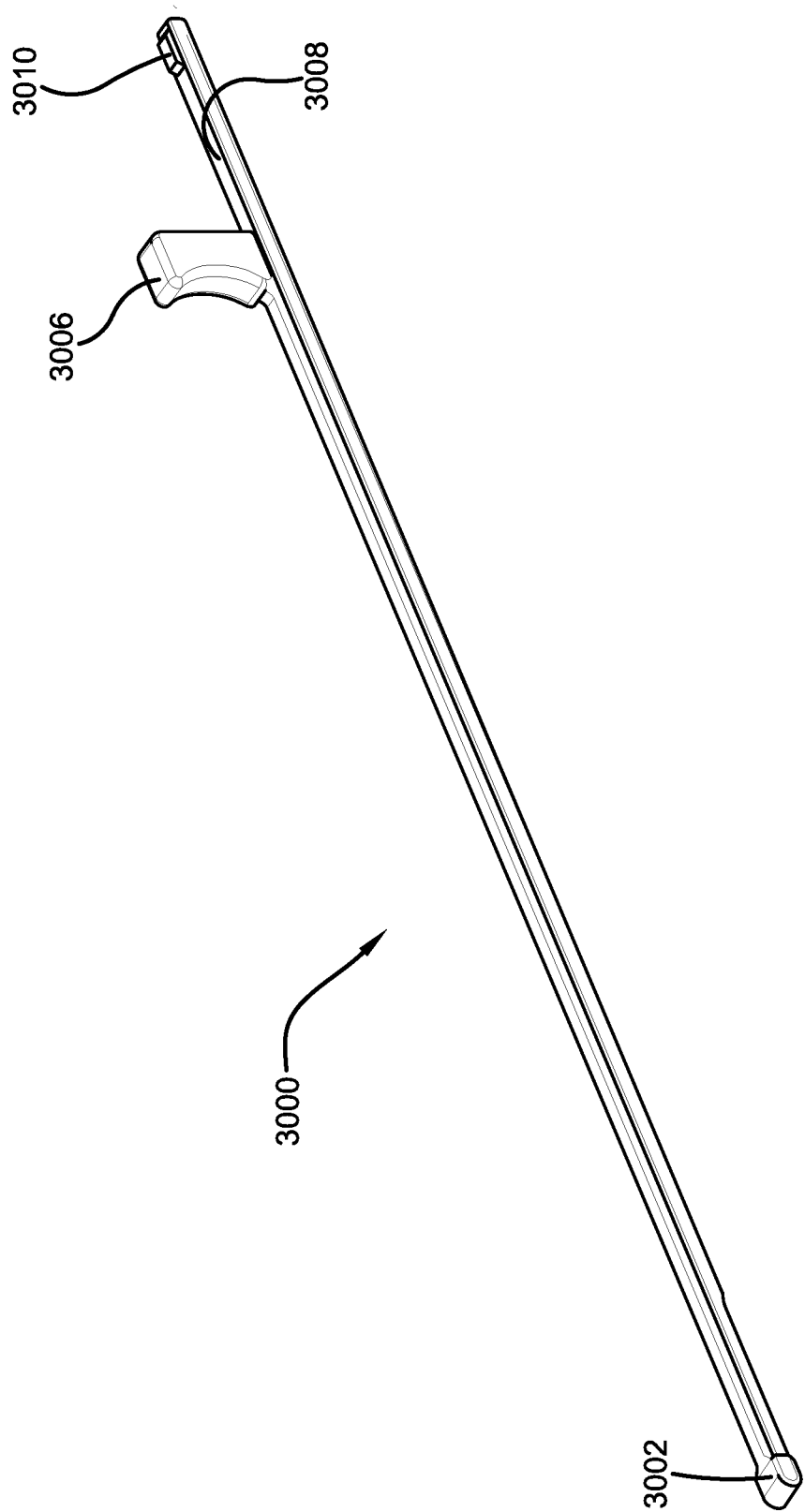
FIG. 51 is a perspective view of remover tamp.

With reference now to FIGS. 51-54, the surgical instrumentation according to some aspects of the present teaching of this invention may include a remover tamp 3000. The remover tamp 3000 may extend longitudinally and may include a distal end with a contact surface 3002. The contact surface 3002 may extend distally as shown. The proximal end of the remover tamp 3000 may include a connection surface 3004. The connection surface 3004 may include a groove 3008 extending to a tab 3010. The tab 3010 may extend upwardly, as shown in FIGS. 51 and 54. A trigger 3006 may extend laterally, as shown. Multiple sizes of remover tamps may be provided to correspond to multiple implant sizes. Markings may be provided on the trigger, as shown, to indicate the size of the remover tamp. The remover tamp 3000 may be a little longer than the inserter tamp 1800 (FIGS. 46-49). In one embodiment, the distance from the proximal end of trigger 3006 to the proximal end of the remover tamp 3000 is greater than the distance from the proximal end of trigger 1806 to the proximal end of inserter tamp 1800.

Figure 55:
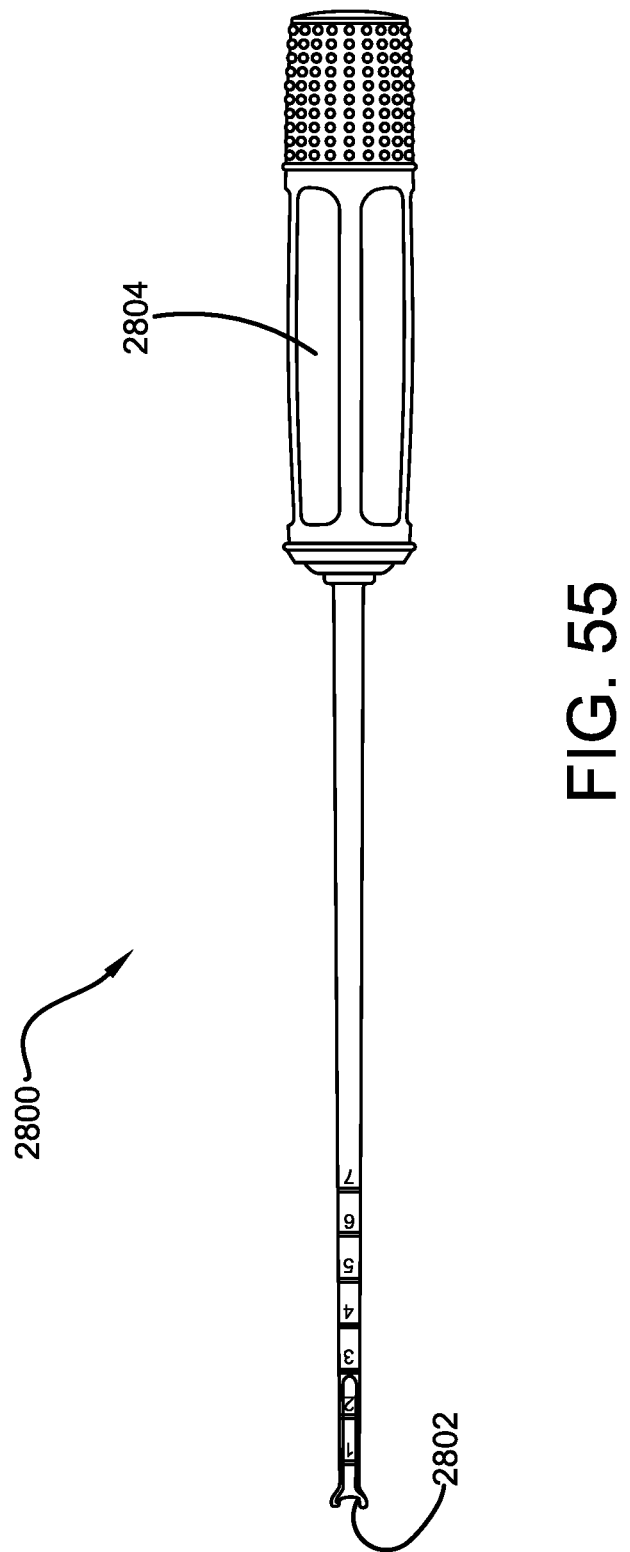
FIG. 55 is a side view of a freehand tamp.
Figure 56:
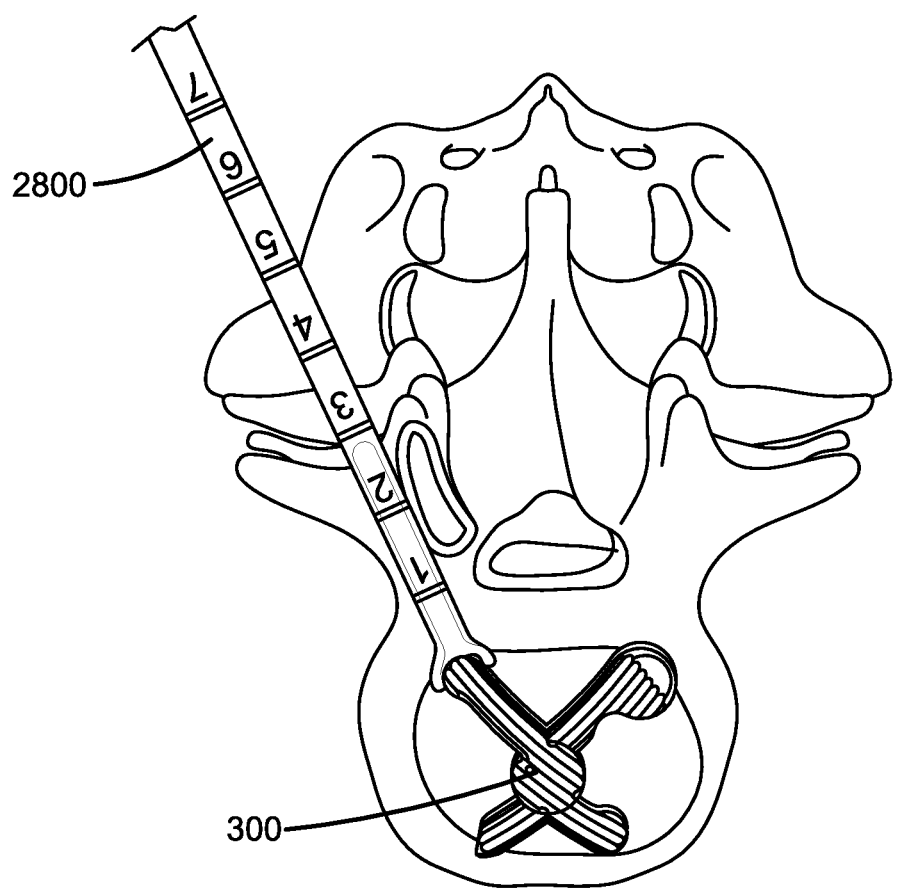
FIG. 56 illustrates a freehand tamp being used to adjust the position of an implant within a vertebral space.

With reference now to FIGS. 55-56, the surgical instrumentation according to some aspects of the present teaching of this invention may include a freehand tamp 2800. The freehand tamp 2800 may extend longitudinally, as shown, and may include a distal end with a contact surface 2802 and a proximal end with a handle 2804. The contact surface 2802 may be sized and shaped to match an outer surface of the implant 300 as shown in FIG. 56.

In what follows, the use of spinal implants and surgical instrumentation according to numerous embodiments will be described. Once the vertebral space 114, 212 (FIGS. 1 and 2) is prepared (including completion of distraction and endplate preparation), trials 400 (FIG. 21) may be used to determine the proper implant 300 size, as discussed above.

Figure 57:
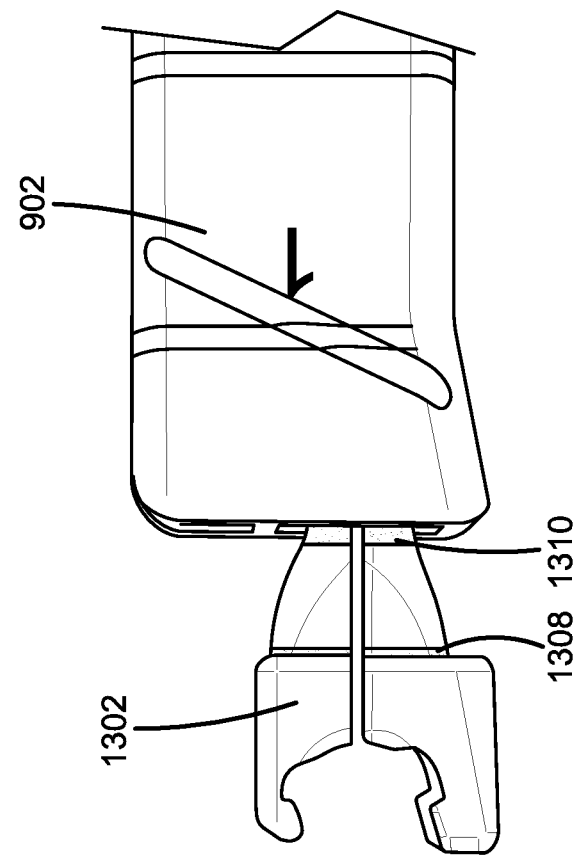
FIG. 57 is a close-up side view of the distal end of an inserter receiving a gripping device.
Figure 58:
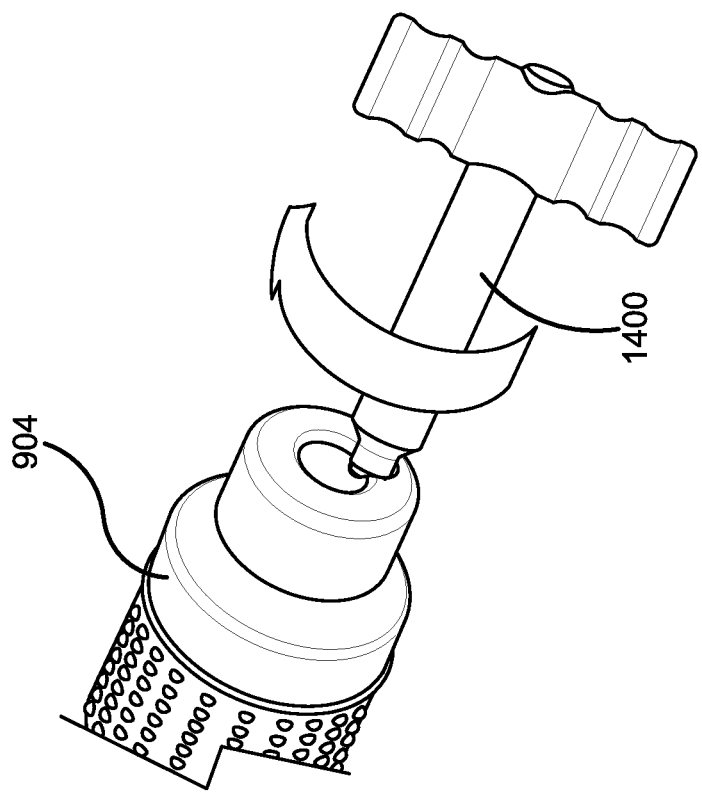
FIG. 58 is a close-up perspective view of the proximal end of an inserter receiving a tool.
Figure 59:
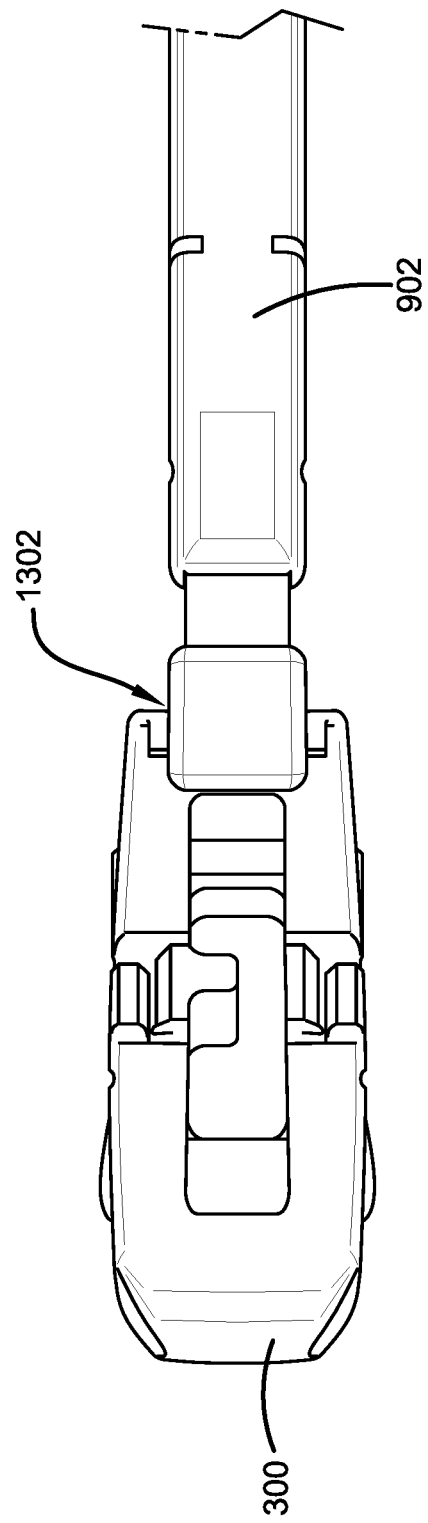
FIG. 59 is a side view showing an implant gripper gripping a spinal implant.
Figure 60:
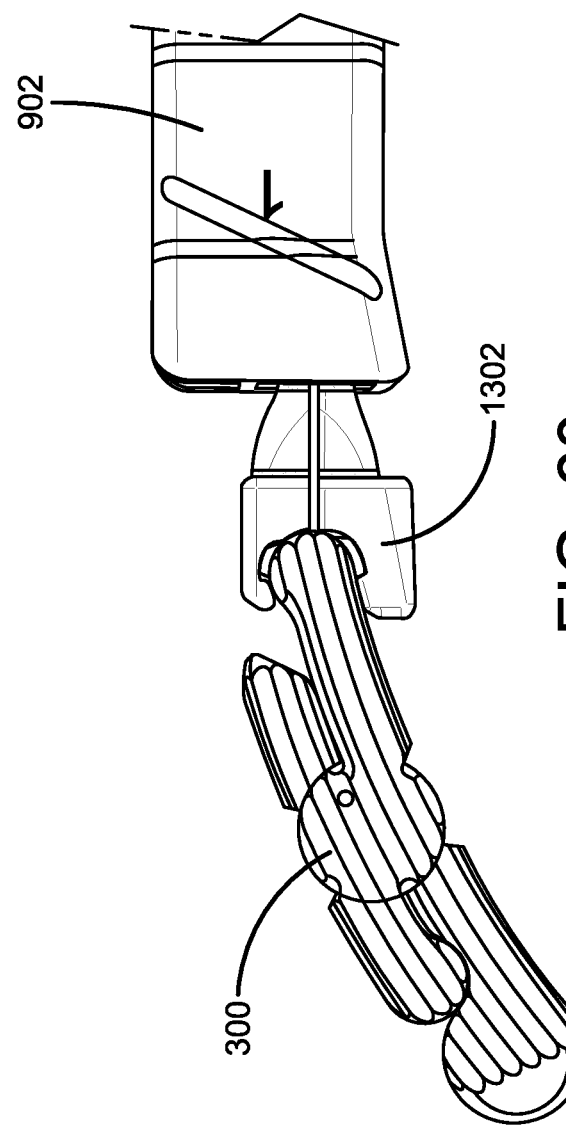
FIG. 60 is a top view of the implant gripper gripping a spinal implant shown in FIG. 59.
Figure 61:
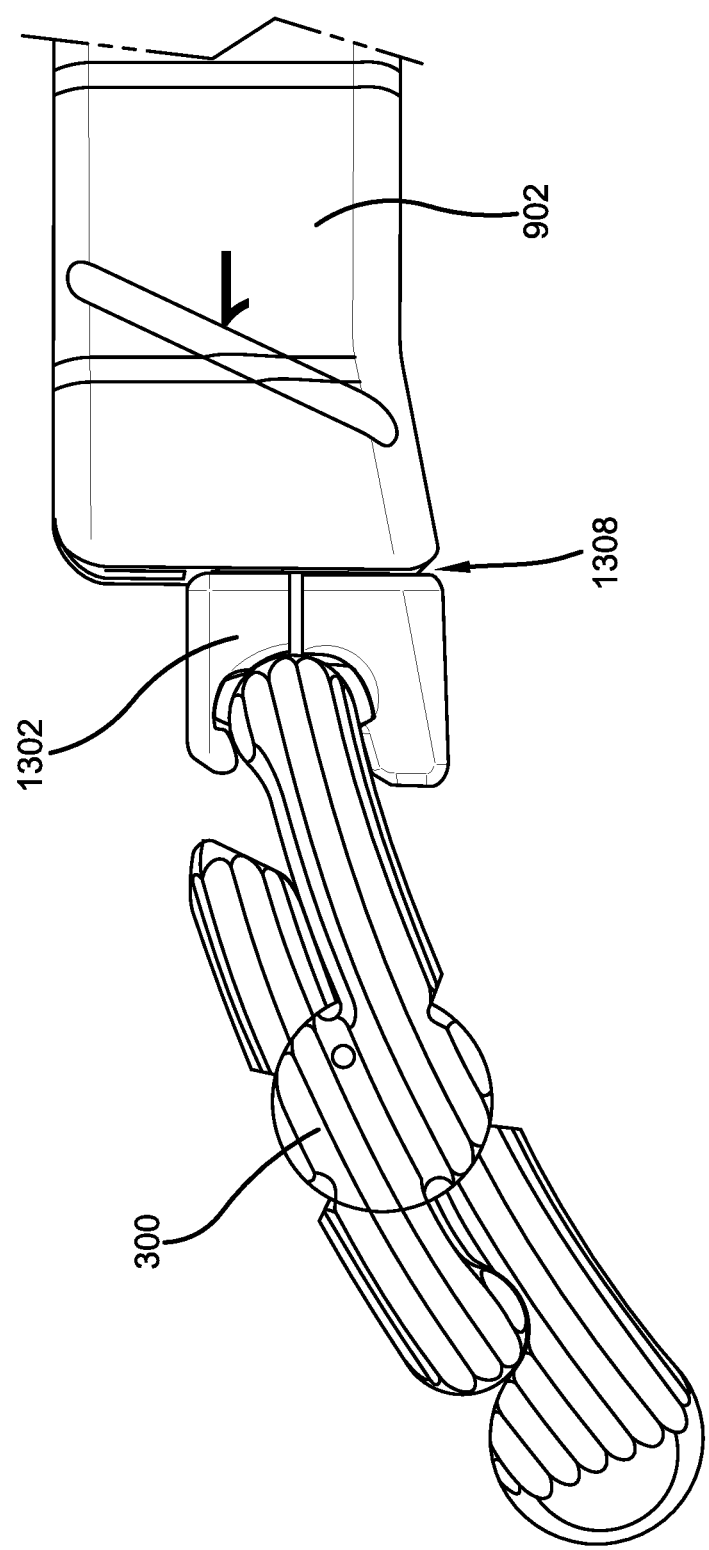
FIG. 61 is a top view of an implant gripper gripping a spinal implant.

With reference now to FIGS. 26, 33, 38-42 and 57-61, in order to grip the implant 300 with the implant gripping mechanism 1320, the gripping device 1300 may be attached to the inserter 900. Specifically, the proximal end of the gripping device 1300 may be inserted into the distal end of channel 922 with connection surface 1312 engaging connection surface 968 of the rotational force converter 930. The distal end of the tool 1400 may then be inserted into the proximal end of channel 922 with connection surface 1404 of the tool 1400 engaging connection surface 966 of the rotational force converter. The tool 1400 may then be rotated in a clockwise direction as indicated in FIG. 58. This rotation may cause the rotational force converter 930 to rotate in the same direction drawing the gripping device 1300 further into the inserter channel 922. The gripping device 1300 may be drawn into the inserter 900 until marking 1310 is aligned with the distal end of the distal end portion 902, as shown in FIG. 57. A portion of the implant 300, as shown in FIGS. 59-60, may then be centered and inserted within the gripper jaws 1304, 1304. The tool 1400 may then be rotated further in the clockwise direction, as shown in FIG. 58, until marking 1308 aligns with the distal end of the distal end portion 902 as shown in FIG. 61. This motion may cause the slot 1306 (FIG. 40) to narrow so that the gripper 1302 firmly grips the implant 300. In this way the tool 1400 can be used to adjust the gripper 1302 to grip the implant 300. Note that in the embodiment shown, the implant 300 is now juxtaposed to the distal end of the channel 922. With this arrangement, the implant 300 may be considered properly seated with respect to the inserter 900.

Figure 62:
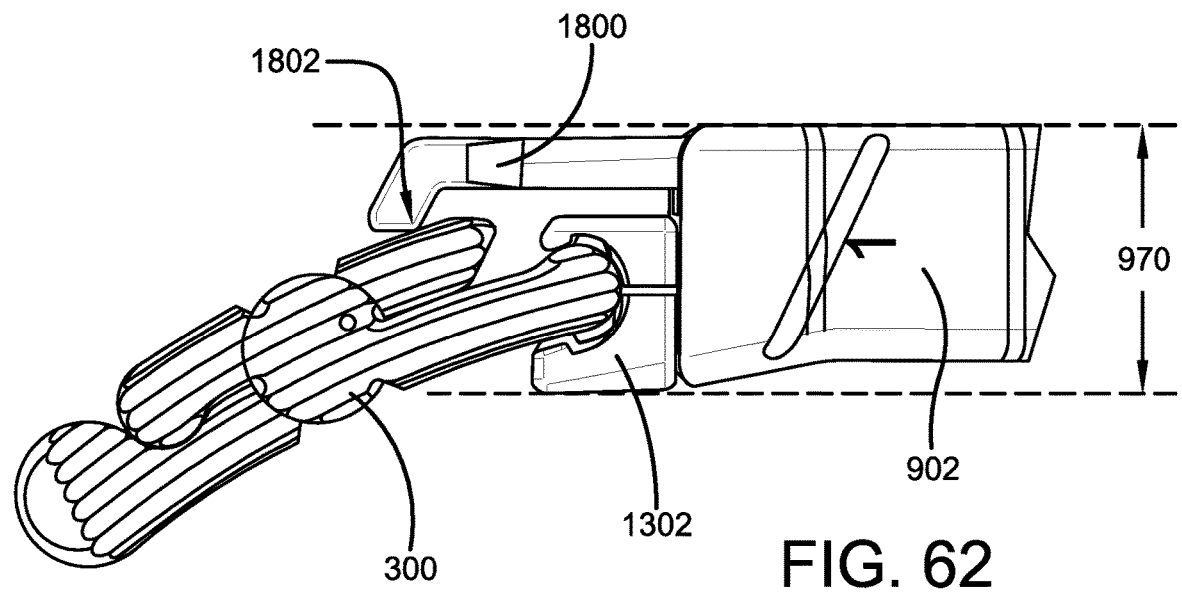
FIG. 62 is a top view of a gripper gripping a spinal implant and an inserter tamp inserter tamp holding the spinal implant in a collapsed condition.
Figure 63:
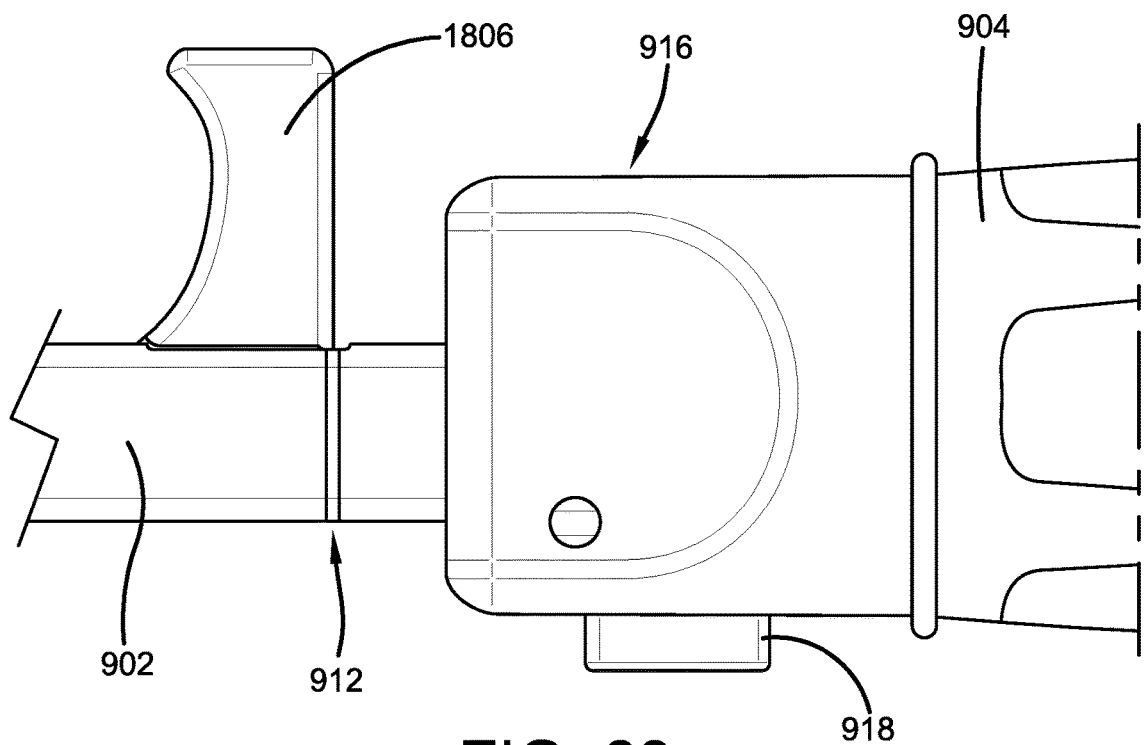
FIG. 63 is a close-up side view of a portion of an inserter receiving an inserter tamp.

With reference now to FIGS. 26, 33-37, 46-50 and 62-63, the implant deployment mechanism 1500 may be attached to the inserter 900. Specifically, the proximal end of the appropriate inserter tamp 1800 may be inserted into the distal end of channel 920 with trigger 1806 extending out of groove 928. As this insertion continues, connection surface 1804 may engage latch mechanism 916. Specifically, as the tamp 1800 is inserted, tab 1810 may contact tab 940 of the button 918, moving button 918 upward (in FIG. 33) overcoming the biasing force of biasing device 926 and the tab 1810 may then be received in groove 944 (while tab 940 is received in groove 1808) as the button 918 moves back downward (under the biasing force). The surgeon may hear an audible "click" as the tamp 1800 is latched to the inserter 900 in this way. Note that in some embodiments, one or both of the proximal end of tab 1810 and the distal end of tab 940 may be angled or curved to ease the contact between tabs 1810 and 940. For the embodiment shown in FIG. 34, the distal end of table 940 is angled for this purpose. The surgeon may then pull trigger 1806 (and thus tamp 1800) proximally to align the proximal edge of the trigger 1806 with the line 912 on the inserter as shown in FIG. 63. This motion may move tab 1810 into opening 948. Tab 1810 and opening 948 may be sized such that tab 1810 fits securely within opening 948. In this position the contact surface 1802 at the distal end of the inserter tamp 1800 contacts the implant 300, as shown in FIG. 62. This contact, along with the gripper 1302 holding a different part of the implant 300, as shown, maintains the implant 300 in the contracted or non-deployed condition. If the implant 300 is inadvertently locked into the expanded or deployed condition prior to insertion within the vertebral space, the implant 300 can be unlocked using lock release tool 800, as described above.

Figure 29:
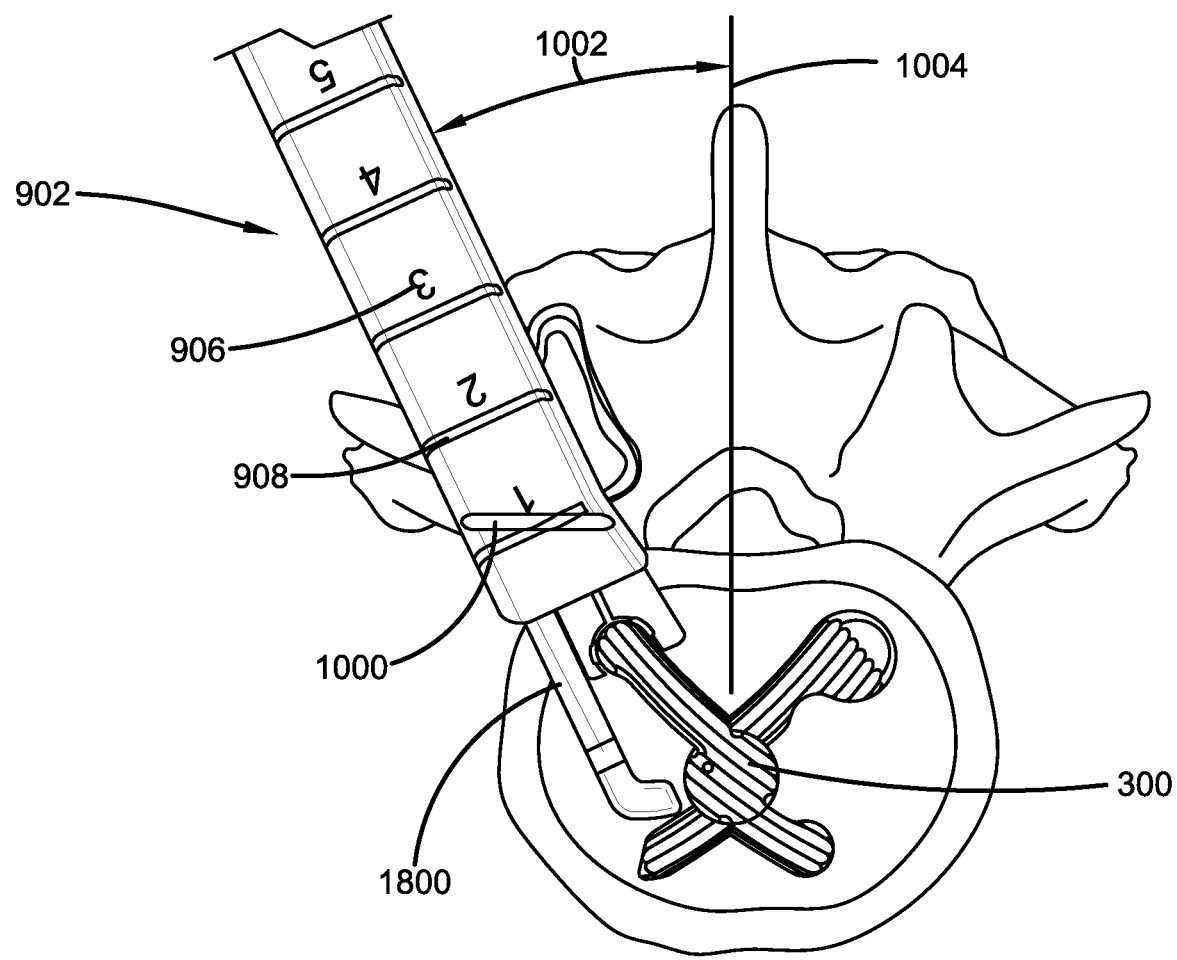
FIG. 29 illustrates an inserter being used to adjust an implant positioned within a vertebral space into a deployed condition.
Figure 30:
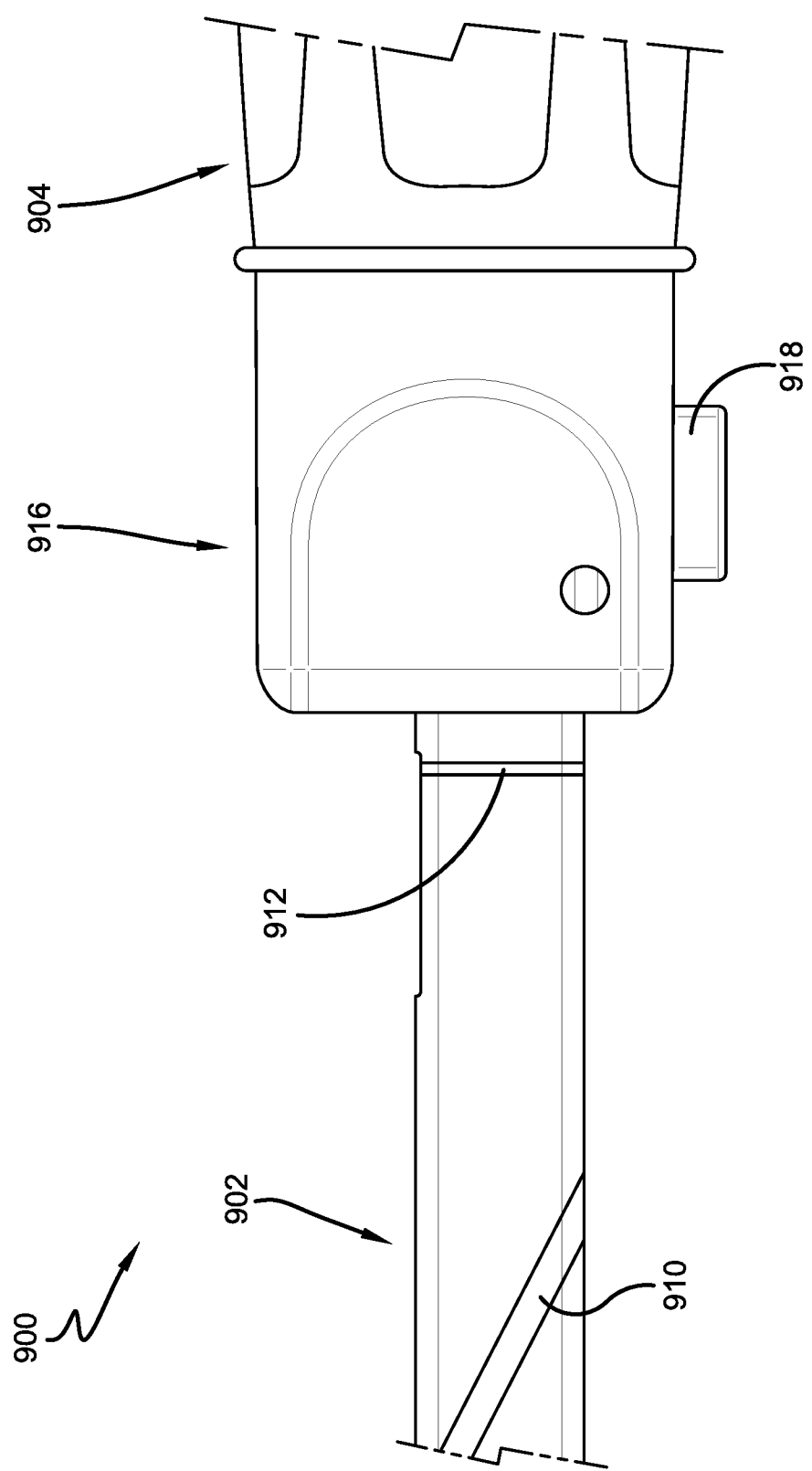
FIG. 30 is a close-up side view of a portion of the inserter shown in FIG. 26.
Figure 31:
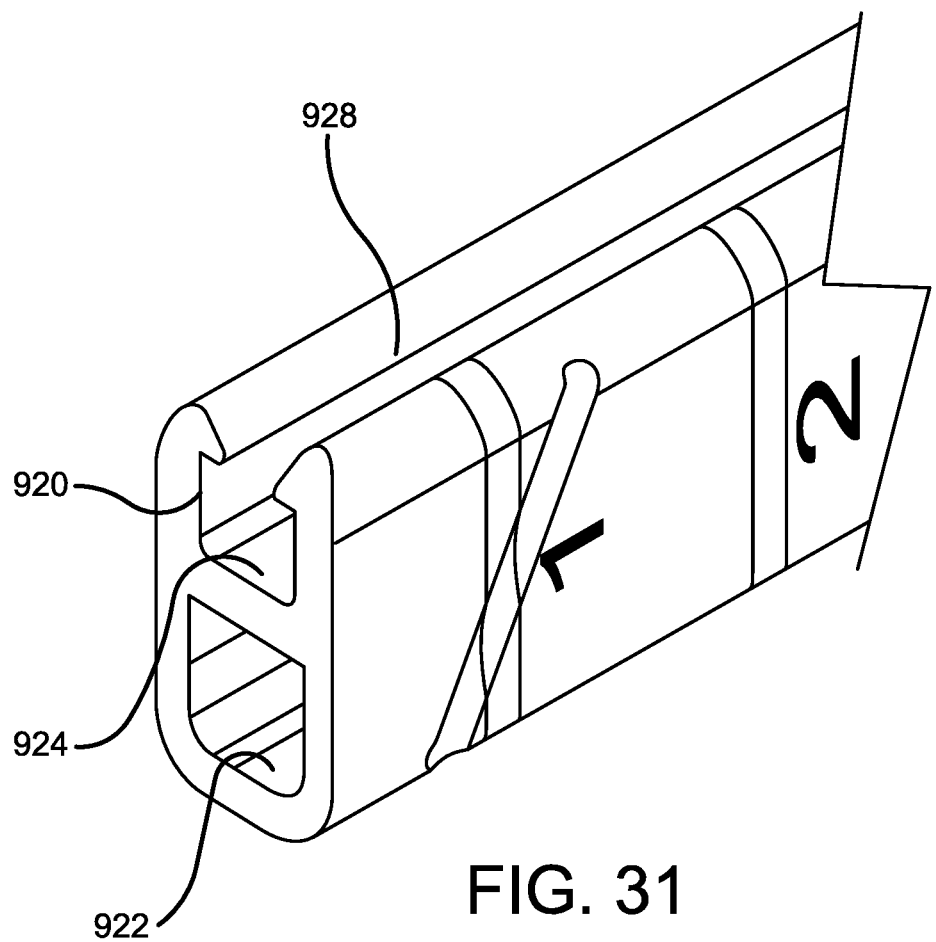
FIG. 31 is a close-up perspective view of the distal end view of an inserter.
Figure 32:
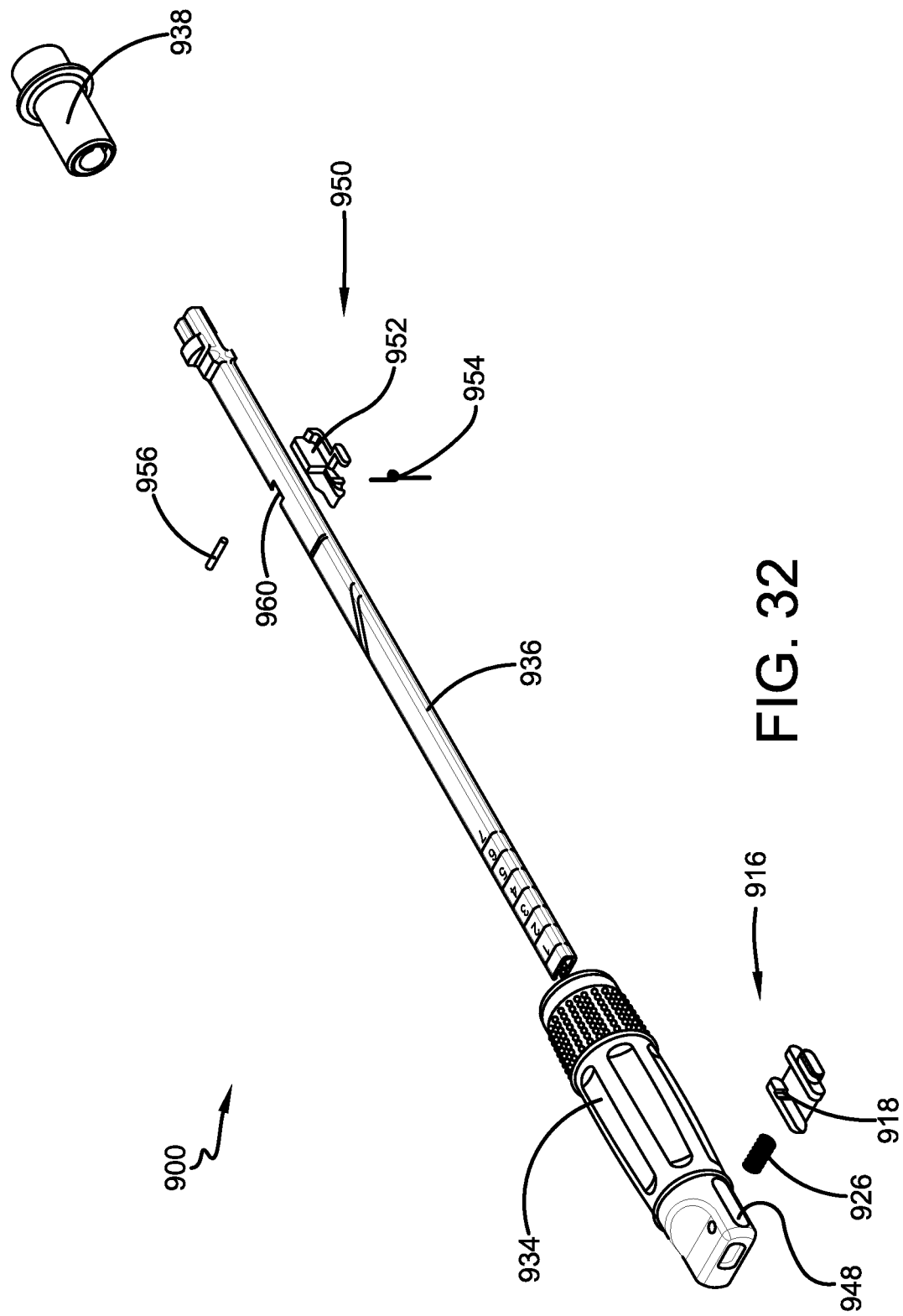
FIG. 32 is an assembly view of an inserter.
Figure 64:
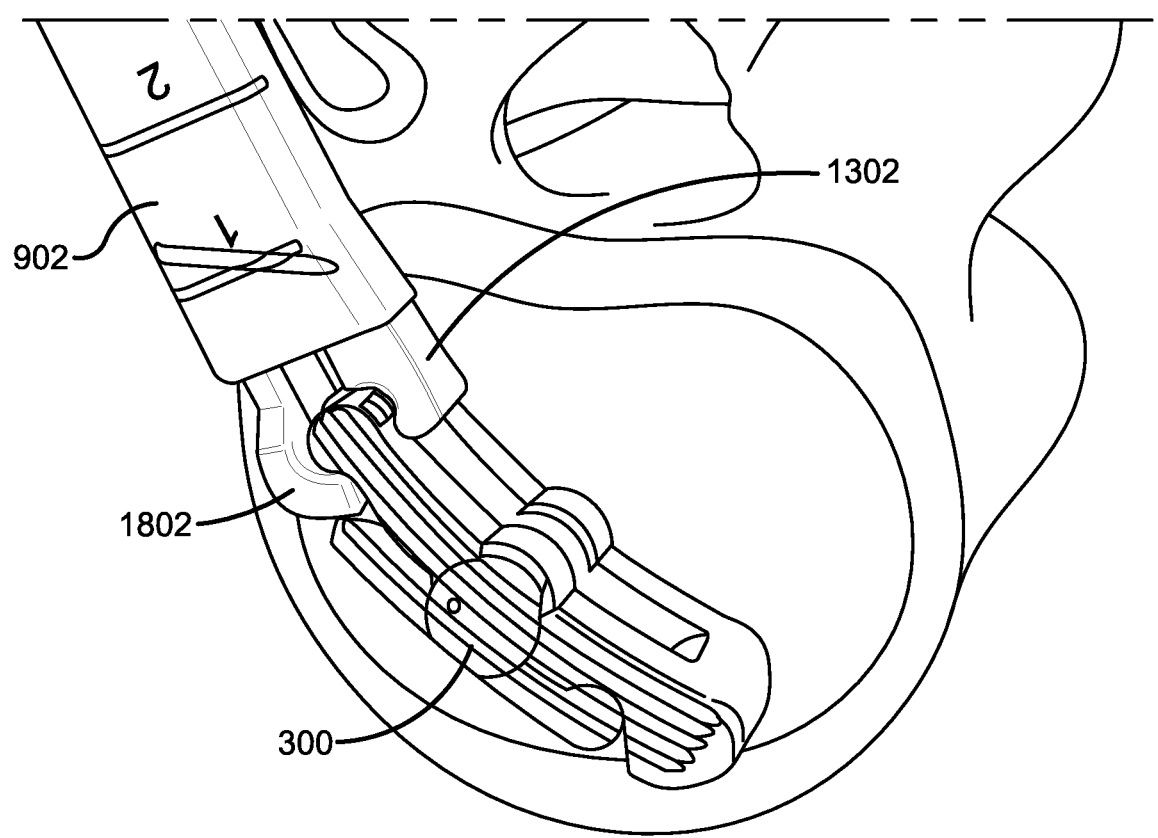
FIG. 64 illustrates an inserter being used to place a spinal implant within a vertebral space.
Figure 65:
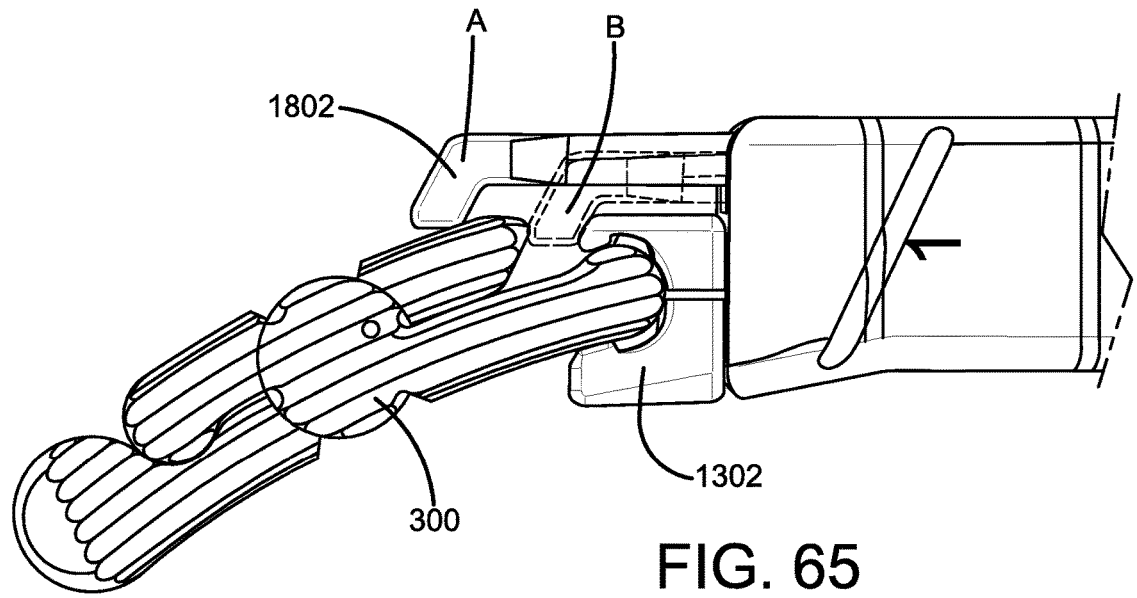
FIG. 65 is a top view of a gripper gripping a spinal implant and an inserter tamp being moved to enable implant deployment.
Figure 66:
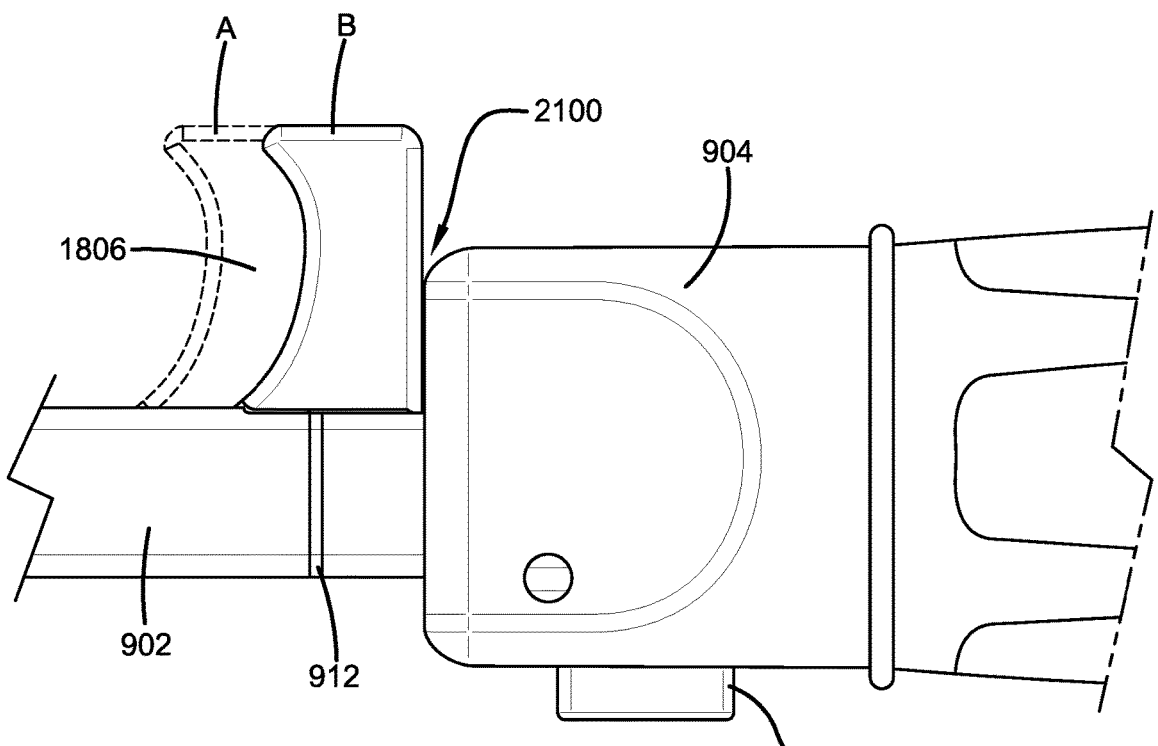
FIG. 66 is a close-up side view of a portion of an inserter and an inserter tamp being moved to enable implant deployment.

With the implant 300 properly attached to the inserter as shown in FIG. 62, the surgeon may insert the implant 300 to the proper location within the vertebral space, as illustrated in FIG. 64. Inserter markings lines 910 and 1000 (see FIGS. 26, 27 and 29) may be used to achieve proper insertion angle 1002 as shown in FIG. 29 and described above. To enable the implant 300 to be deployed within the vertebral space, the surgeon may adjust the inserter tamp 1800 out of the position where it holds the implant 300 in the contracted or non-deployed condition. This may be done by pressing contact surface 946 of button 918 inward against the biasing force (upward in FIG. 33) while simultaneously applying a proximal force to the trigger 1806 (and thus to the tamp 1800). This motion may move the trigger 1806 from position A to position B (FIG. 66) where the trigger 1806 contacts a distal surface of the proximal end portion 904 of the inserter 900 at location 2100. This motion may also move tamp tab 1810 under button tab 942. In some embodiments, this motion may also move tamp tab 1810 into contact with tab 958 of latch mechanism 950 (FIG. 35), pivoting object 952 while overcoming the biasing force of biasing device 954. This provides additional stability for holding the tamp 1800 in this position. This same motion of the tamp 1800 may simultaneously move the inserter tamp contact surface 1802 from position A to position B (FIG. 65). In this way, the contact surface 1802 no longer prevents the implant 300 from being deployed. Note that the latch mechanism 916 may prevent the tamp 1800 from being moved in this way unless the surgeon first manually adjust the latch mechanism 916 by pressing button 918.

Figure 68:
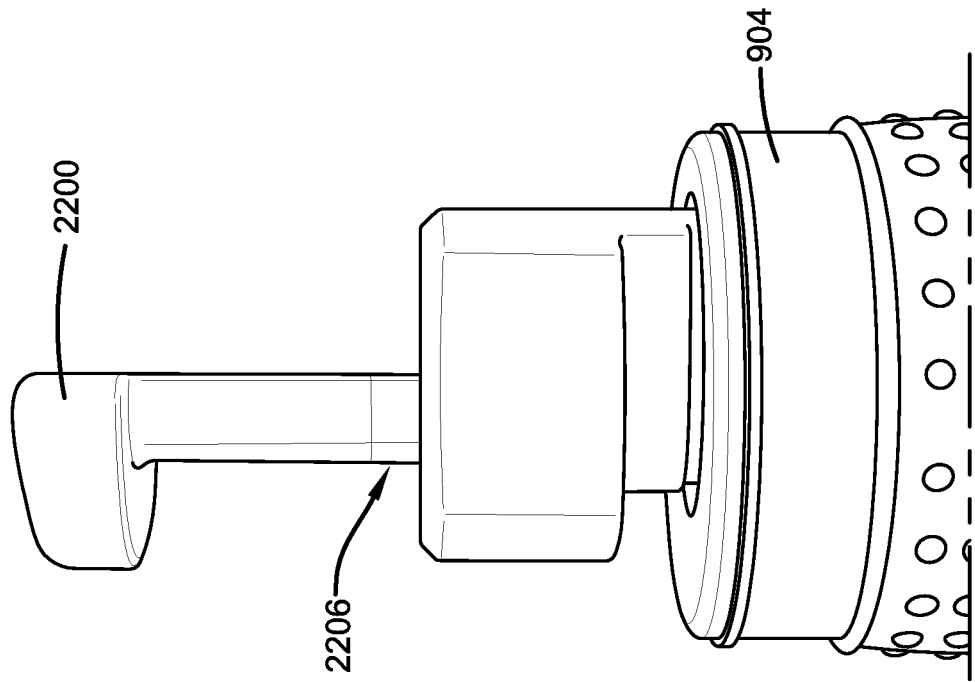
FIG. 68 is a side view of the proximal end of an inserter showing the impactor positioned within the inserter.
Figure 67:
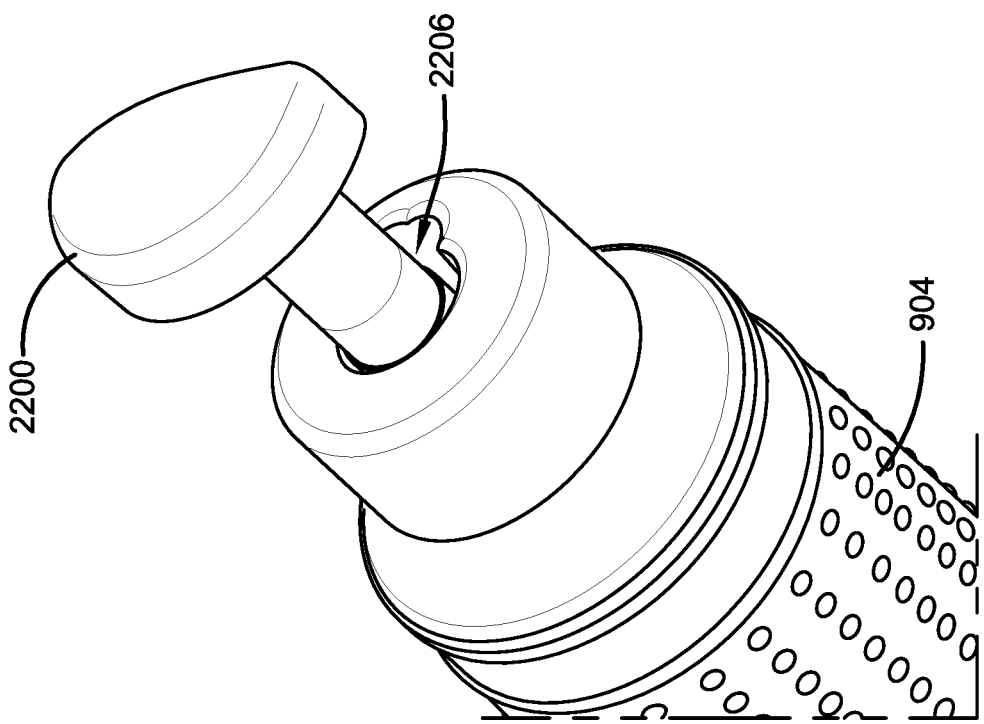
FIG. 67 is a perspective view of the proximal end of an inserter showing the impactor positioned within the inserter.
Figure 69:
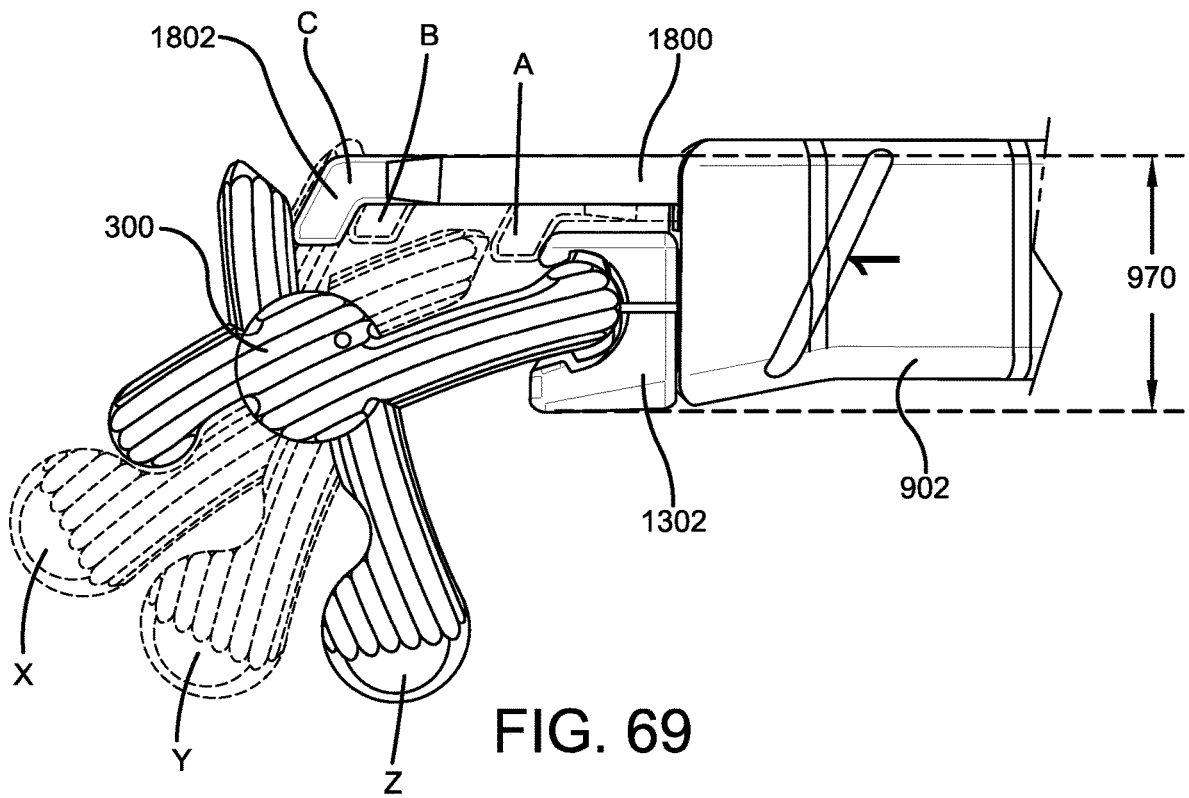
FIG. 69 is a top view of a gripper gripping a spinal implant and an inserter tamp being moved to deploy the spinal implant.
Figure 70:
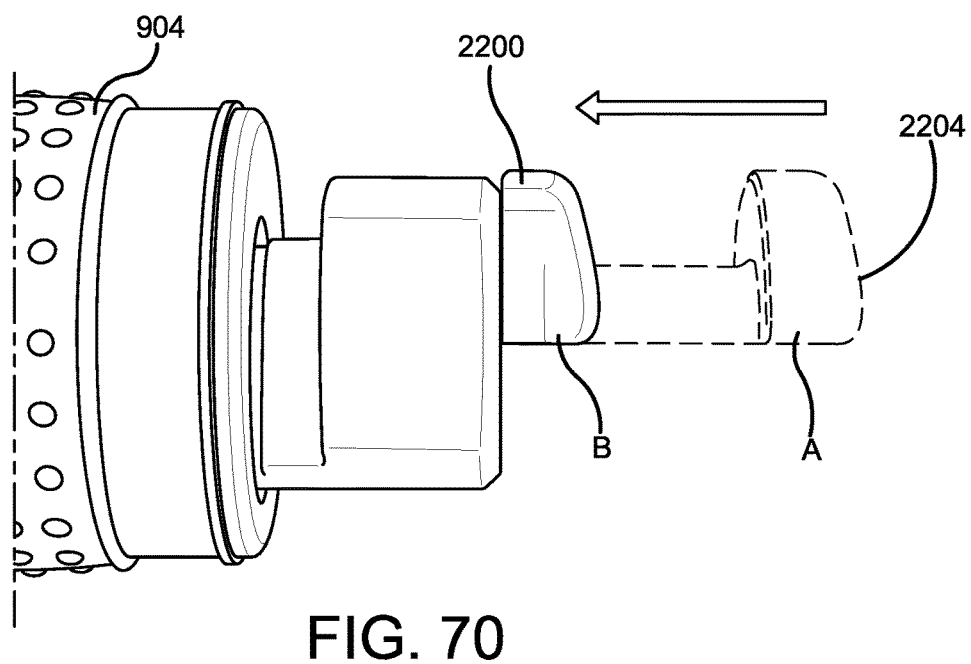
FIG. 70 is a side view of the proximal end of an inserter showing the impactor being moved to deploy the spinal implant.
Figure 71:
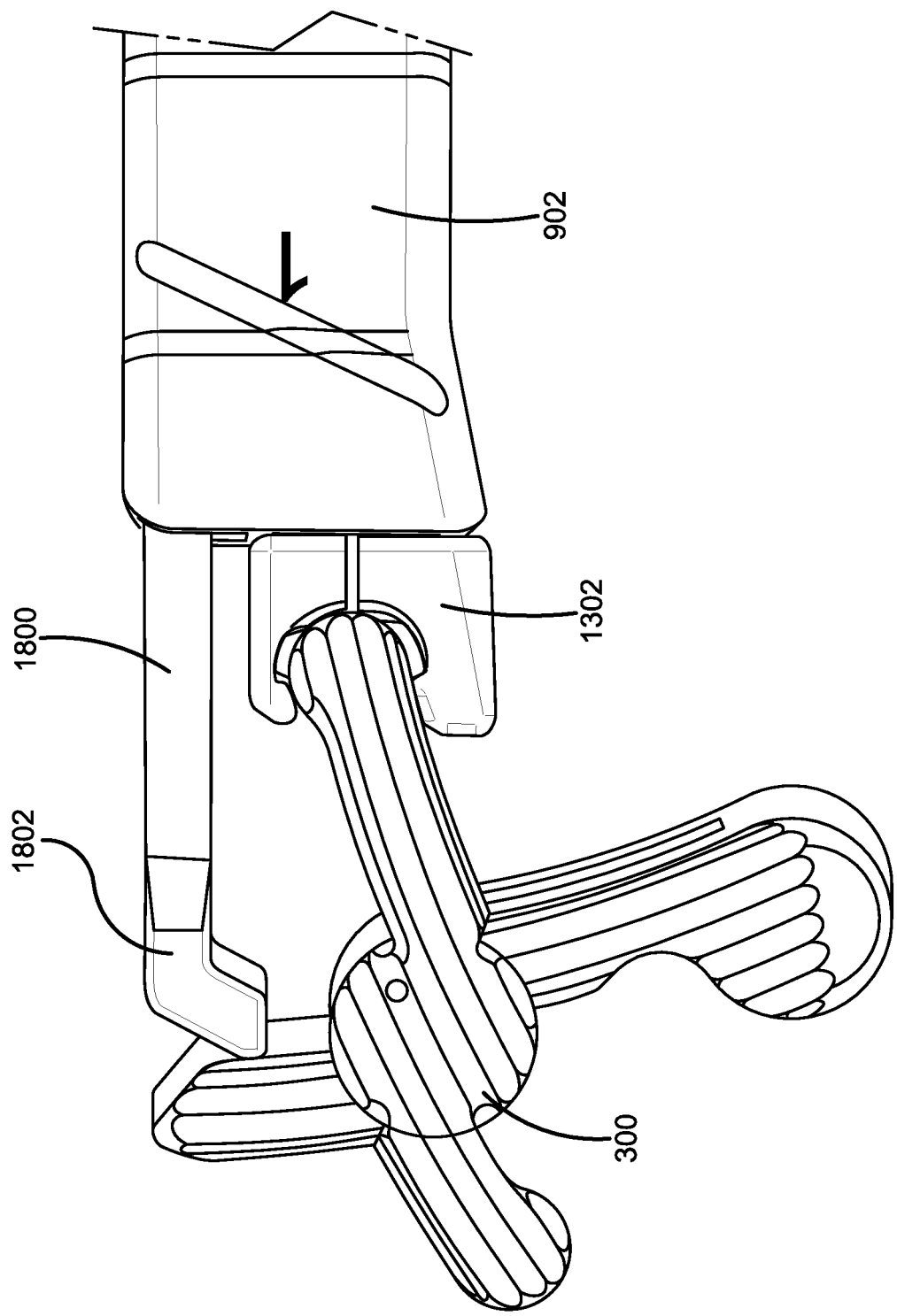
FIG. 71 is a top view of a gripper gripping a spinal implant and an inserter tamp extended to deploy the spinal implant.

With reference now to FIGS. 26, 33, 46-50 and 67-71, once the correct impactor has been selected, the surgeon may insert the distal end of the impactor 2200 into the proximal end of channel 920. The surgeon may push the impactor 2200 into the inserter 900 until marking 2206 is positioned at the proximal end of the inserter 900 as shown in FIGS. 67 and 68. In this condition, the contact surface 2202 of the impactor 2200 may contact the proximal end of the inserter tamp 1800 within channel 920. To adjust the tamp 1800 to deploy the implant 300, the surgeon may then use a mallet or other device against contact surface 2204 to move the impactor 2200 within the inserter 900. Specifically, the impactor 2200 may be moved from position A to position B (FIG. 70). This movement causes the contact surface 2202 of the impactor 2200 (see FIG. 50) to apply a force to the inserter tamp 1800 causing it to move from position A to position B to position C (FIG. 69). This movement of the inserter tamp 1800 causes the implant 300 to deploy by moving in turn from position X to position Y to position Z, also shown in FIG. 69. This distal movement of the impactor 2200 also moves impactor tab 2212 into button groove 944 and button tab 942 into impactor groove 2210. In this way, the impactor 2200 is latched to the inserter 900. FIG. 71 also shows the implant 300 in the deployed condition. The surgeon may use fluoroscopy and the relative positions of pins 332, 350, as described above, to confirm that the implant 300 is locked into the deployed condition.

With reference now to FIGS. 26, 33, 55-56 and 72-73, with the implant 300 positioned and deployed within the vertebral space, the surgeon may then detach the inserter 900 from the implant 300. This may be accomplished by rotating the tool 1400 in a counterclockwise direction, as shown in FIG. 73. This rotation may cause the rotational force converter 930 to rotate in the same direction extending the gripping device 1300 distally further out of the inserter 900 which in turn may cause the slot 1306 to enlarge so that the gripper 1302 releases the implant 300 as illustrated in FIG. 72. The surgeon may then remove the inserter 900 from the vertebral space. If desired, the surgeon may then adjust the position of the implant 300 with the freehand tamp 2800 (FIGS. 55-56), gripping the handle 2804, as needed.

With reference now to FIGS. 26, 33, 35-37 and 73-75, the surgical instruments may be disassembled from the inserter 900. FIG. 74 illustrates how the impactor 2200 and the inserter tamp 1800 may be easily removed. First, the button 918 may be pressed inwardly (upwardly in FIG. 74) to overcome the biasing force of biasing device 926 and thus to open the latch mechanism 916. While holding the button 918 in the inward position, the impactor 2200 and the inserter tamp 1800 are no longer latched and thus can easily be pulled out of the inserter channel 920 in directions A and B, respectively. The button 918 can then be released. Note that latch mechanism 950, if used, does not prevent removal of these components. To remove the gripping device 1300, the tool 1400 may be rotated in the counterclockwise direction as shown in FIG. 73. This rotation may cause the rotational force converter 930 to rotate in the same direction extending the gripping device 1300 distally further out of the inserter 900 until the rotational force converter 930 releases (disengages) the gripping device 1300. The gripping device 1300 can then, as shown in FIG. 75, simply be pulled out of the inserter channel 922 in direction C.

Figure 76:
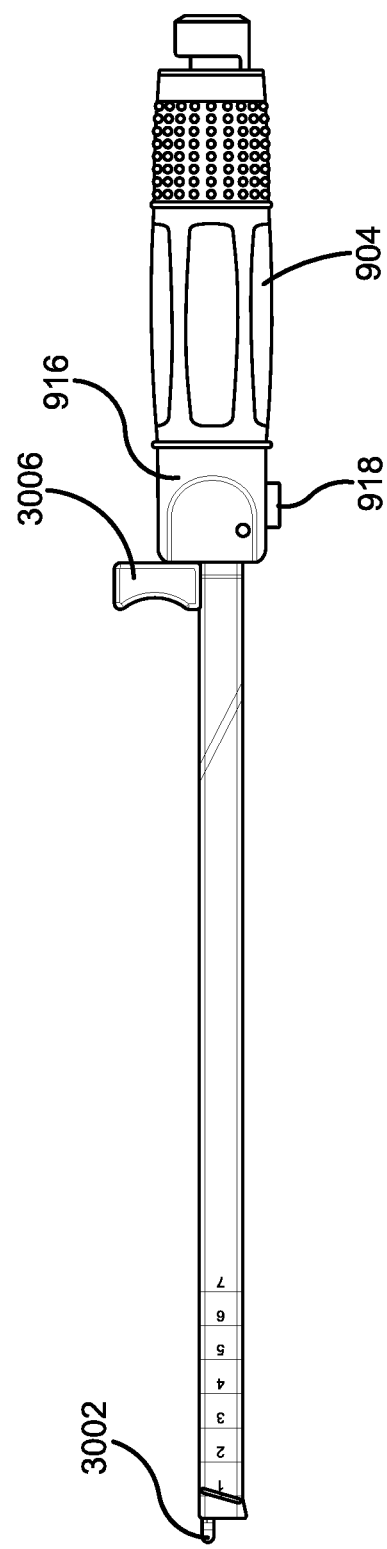
FIG. 76 is a side view showing a remover tamp being inserted into an inserter.
Figure 77:
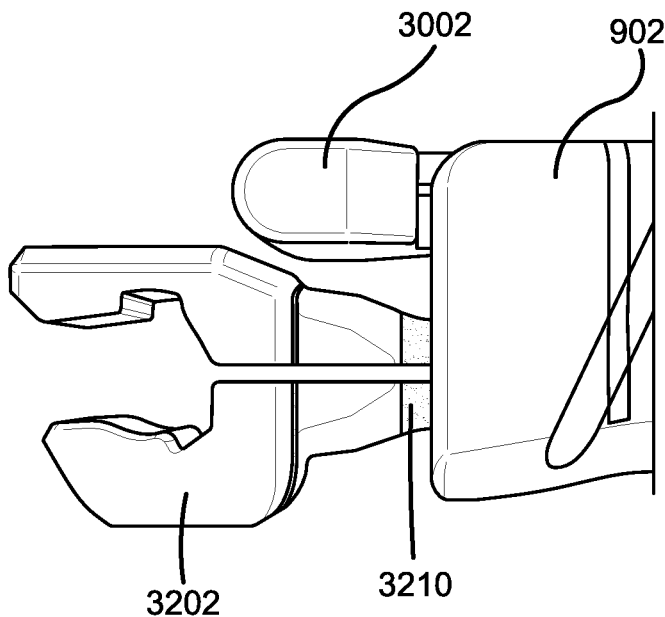
FIG. 77 is a close-up side view of the distal end of an inserter showing a remover tamp and gripping device.
Figure 78:
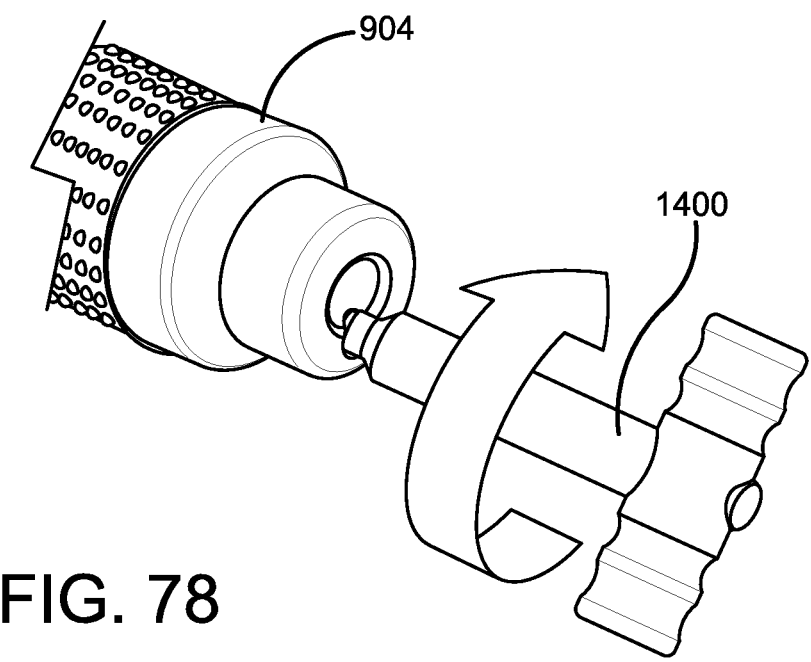
FIG. 78 is a perspective view of the proximal end of an inserter showing a tool being rotated to close a gripping device.
Figure 79:
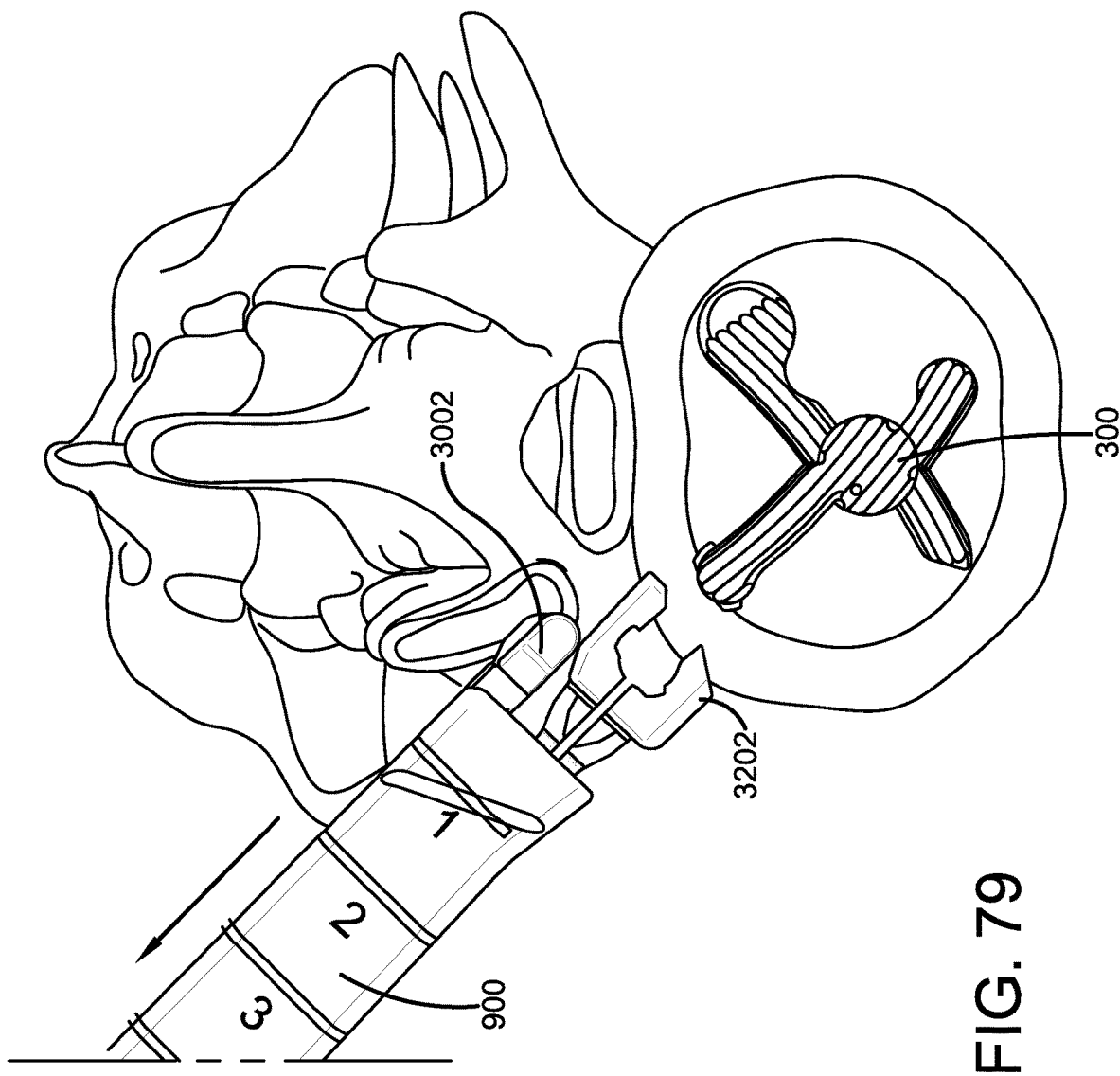
FIG. 79 illustrates a remover tamp and gripping device being positioned to engage a deployed spinal implant within a vertebral space.
Figure 80:
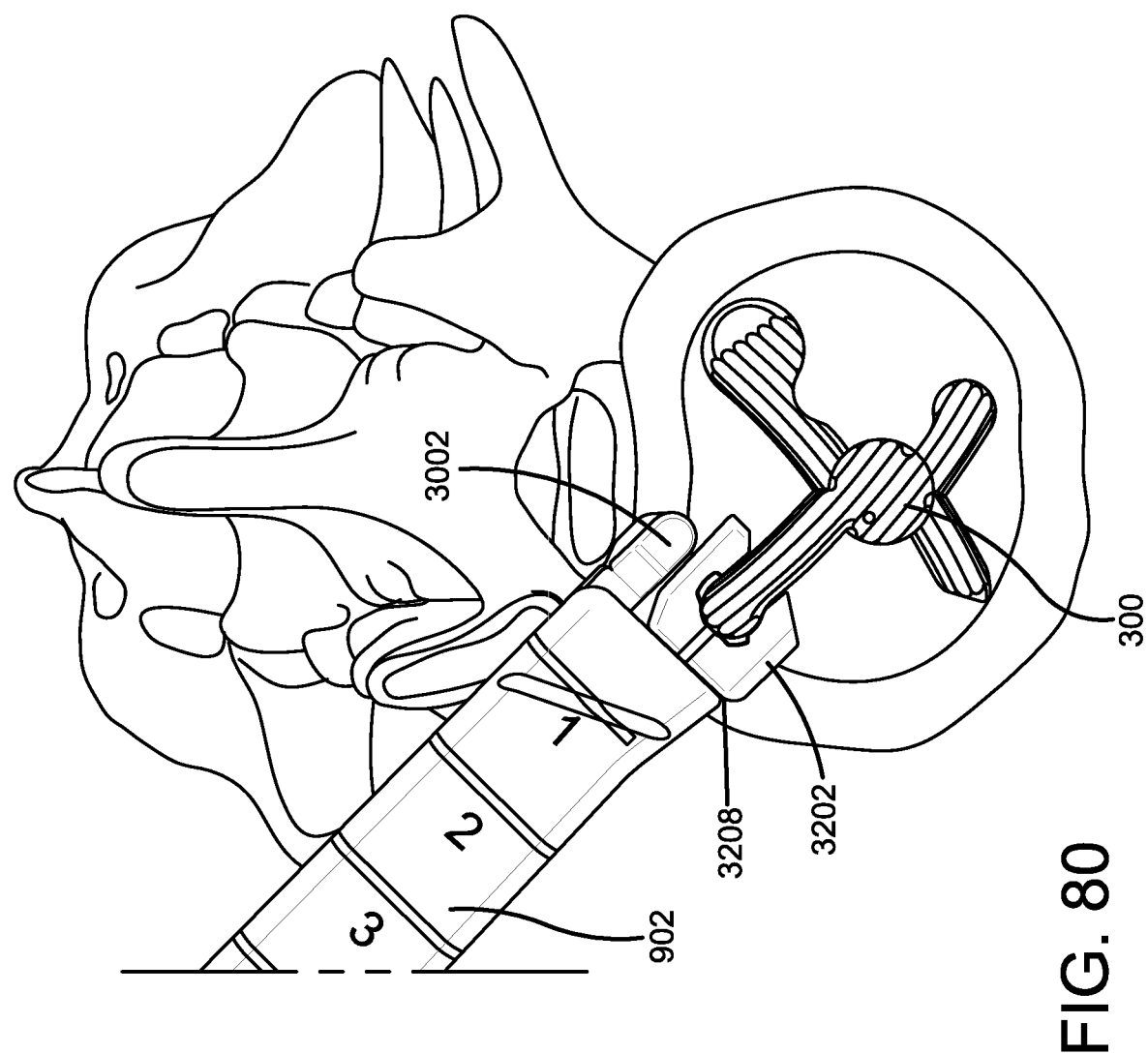
FIG. 80 illustrates a gripping device gripping a deployed spinal implant within a vertebral space.

With reference now to FIGS. 26, 33, 51-54, 76-80, in some cases, it may be necessary to remove the implant 300 from the vertebral space. In this case, the appropriate remover tamp 3000 may be attached to the inserter 900 in the same manner as inserter tamp 1800, described above. The result is shown in FIG. 76 with the trigger 3006 contacting a distal surface of the proximal end portion 904 of the inserter 900. Gripping device 3200 may be attached to the inserter in the same manner as gripping device 1300, described above. In this way, tool 1400 may be rotated in clockwise direction as indicated in FIG. 78 drawing gripping device 1300 to the position shown in FIG. 77. The inserter 900 may then be inserted into the vertebral space, as illustrated in FIG. 79, until the grip mechanism 3202 is positioned around an outer surface of the implant 300. The tool 1400 may then be rotated further in the clockwise direction, as shown in FIG. 78, until the marking 3208 is flush with the distal end of the inserter as illustrated in FIG. 80. This indicates that the grip mechanism 3202 has a tight grip on the implant 300.

Figure 83:
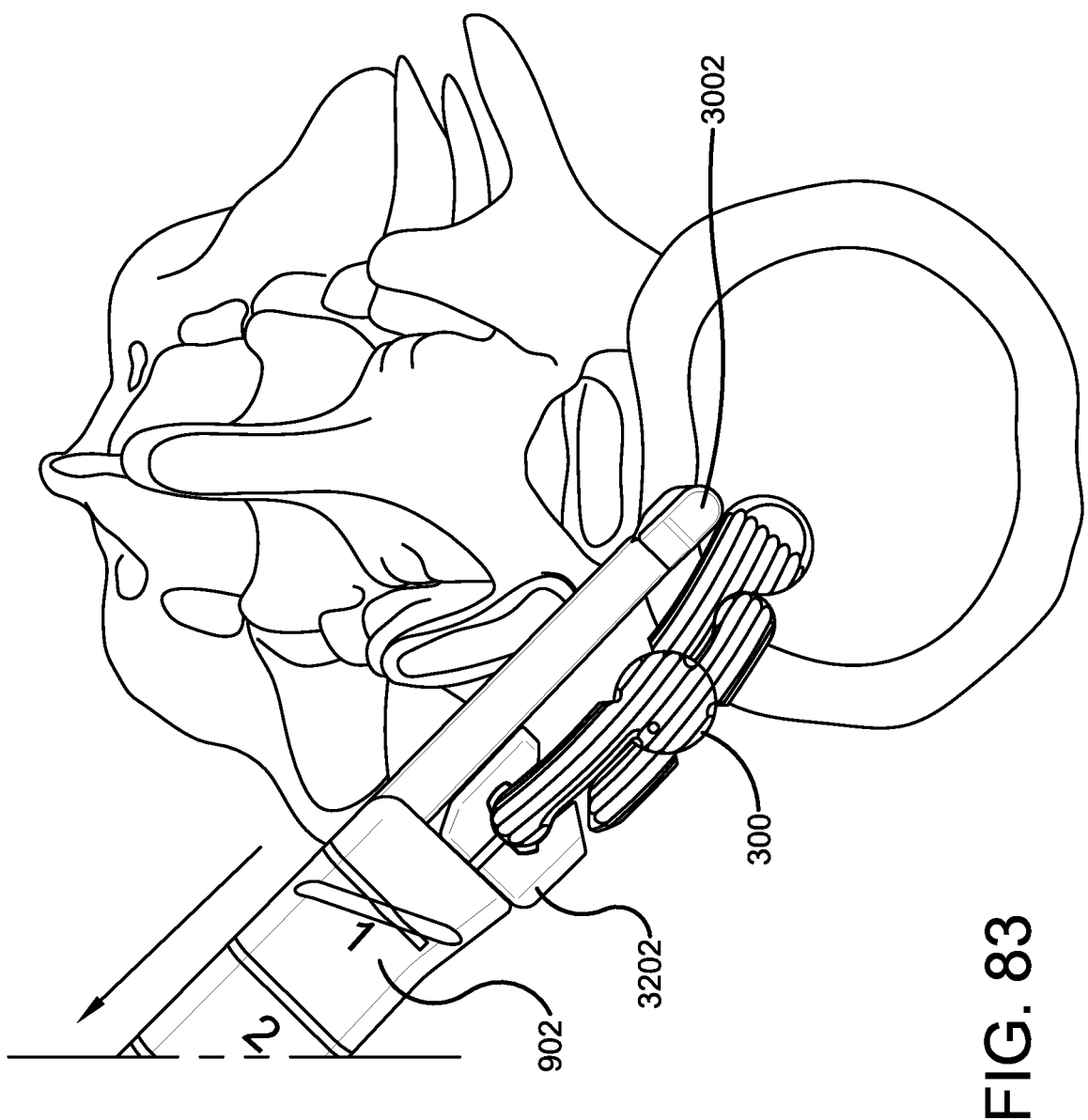
FIG. 83 illustrates a collapsed implant being removed from a vertebral space.
Figure 84:
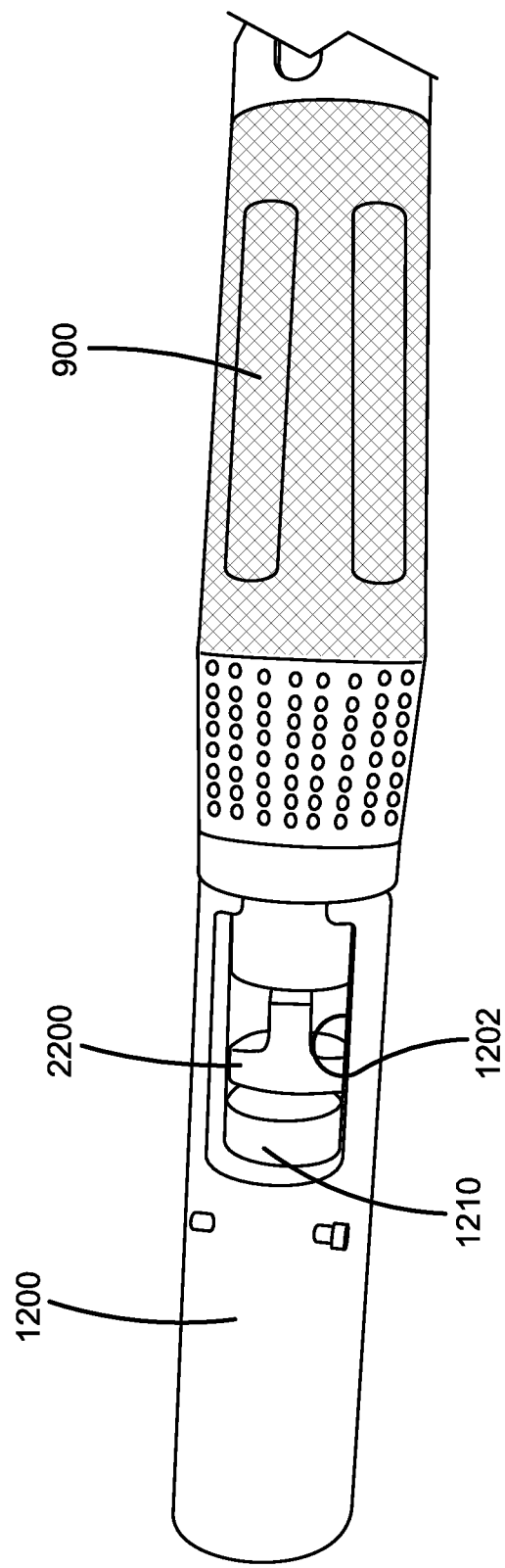
FIG. 84 shows a rotational force converter engaged to an inserter and impactor with the piston contacting the impactor.
Figure 85:
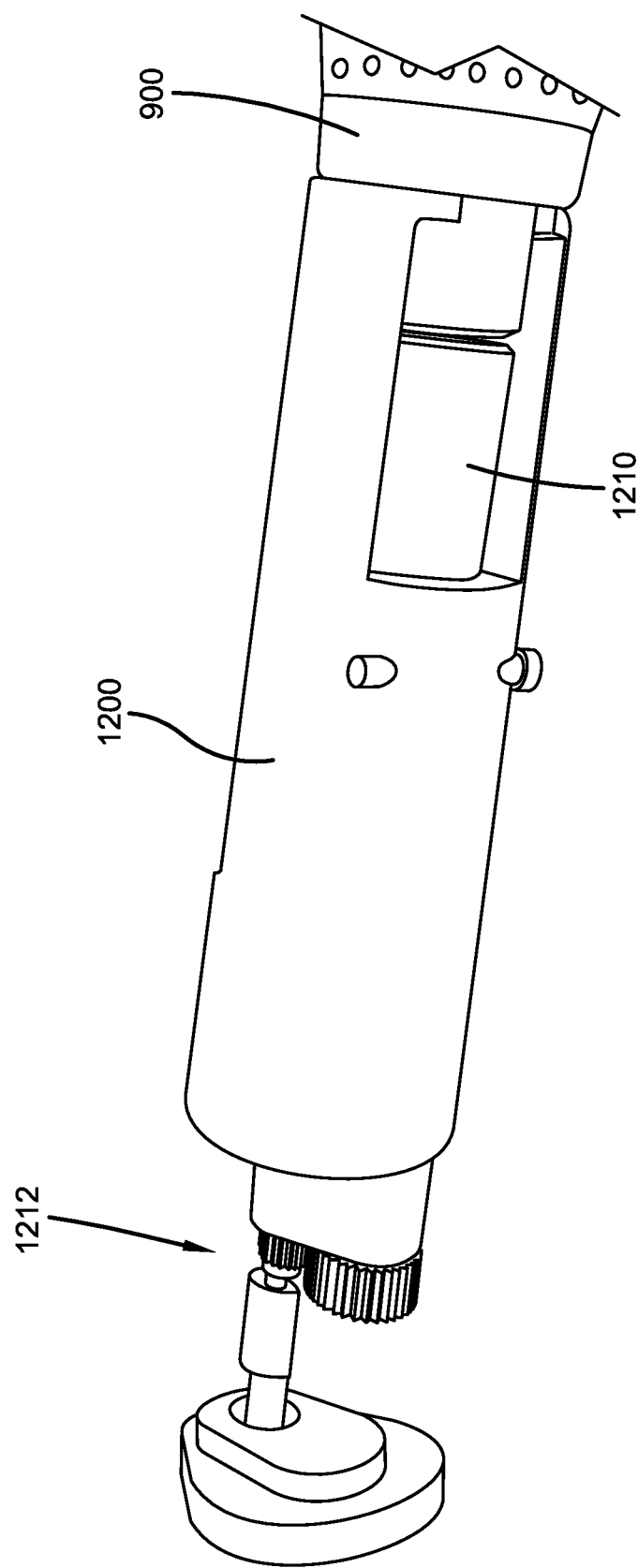
FIG. 85 shows the rotational force converter of FIG. 84 but with the piston extended distally and the piston drive assembly partially removed so it can be seen.
Figure 86:
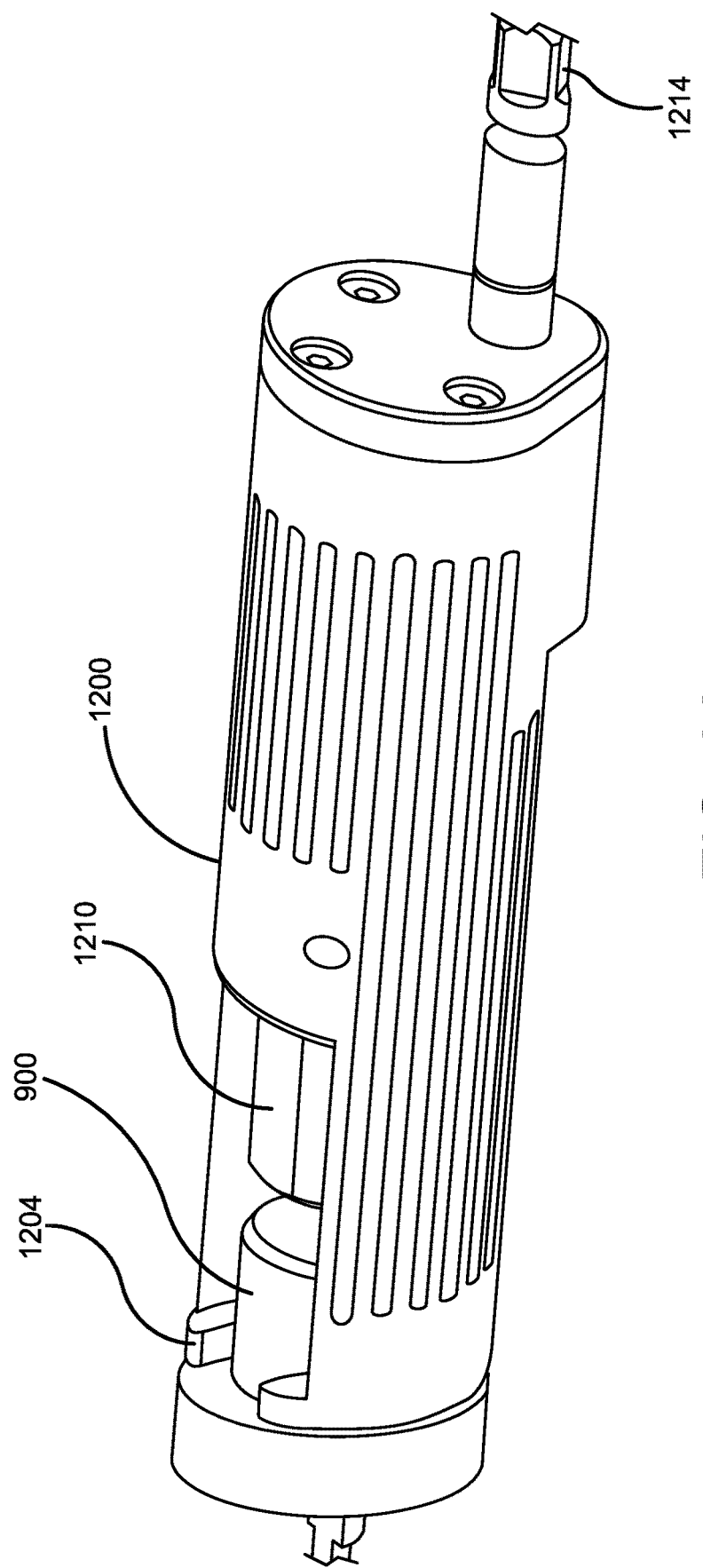
FIG. 86 shows a rotational force converter engaged to an inserter and impactor.
Figure 87:
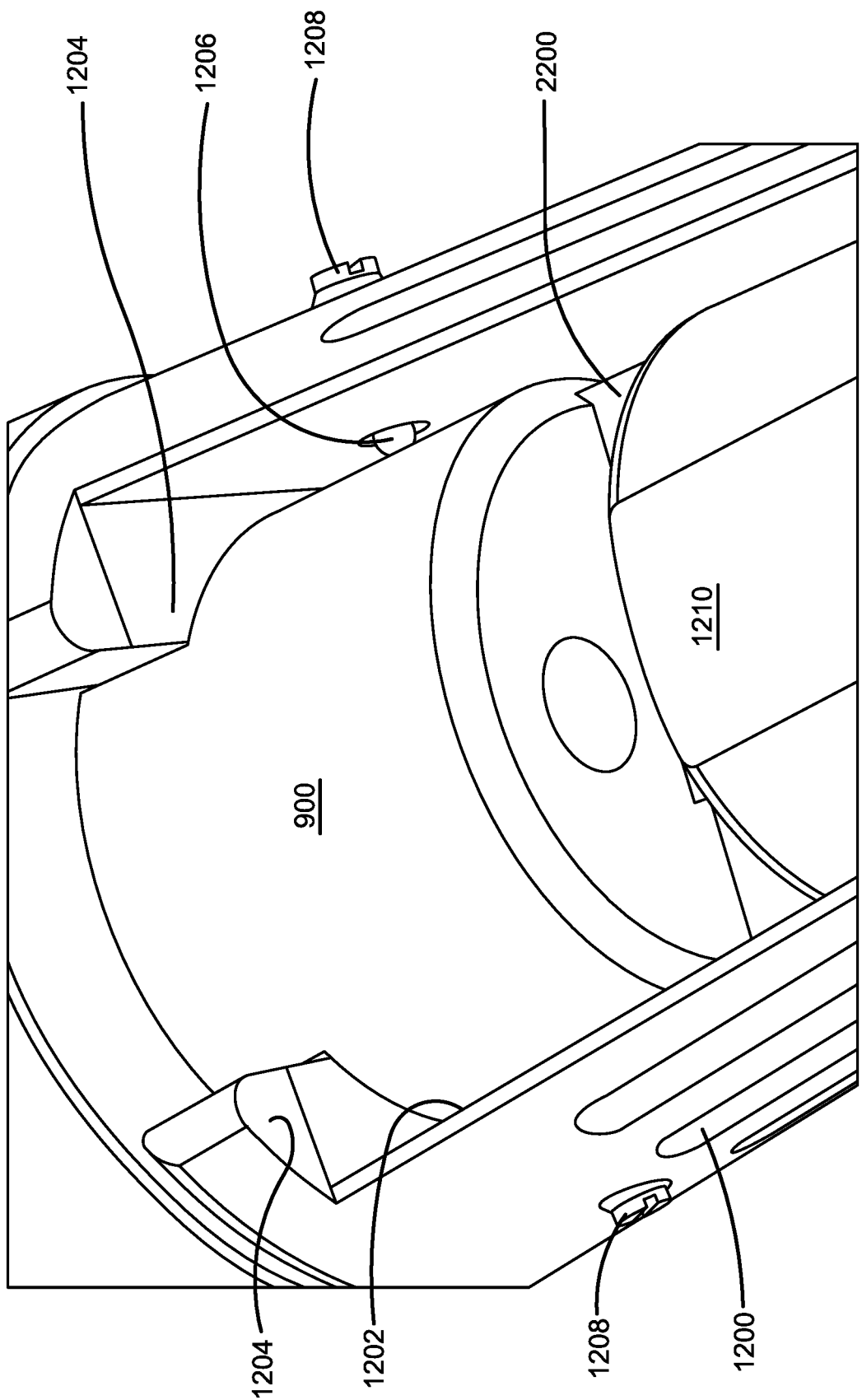
FIG. 87 shows a close-up view inside the reception cavity of the rotational force converter shown in FIG. 86.
Figure 88:
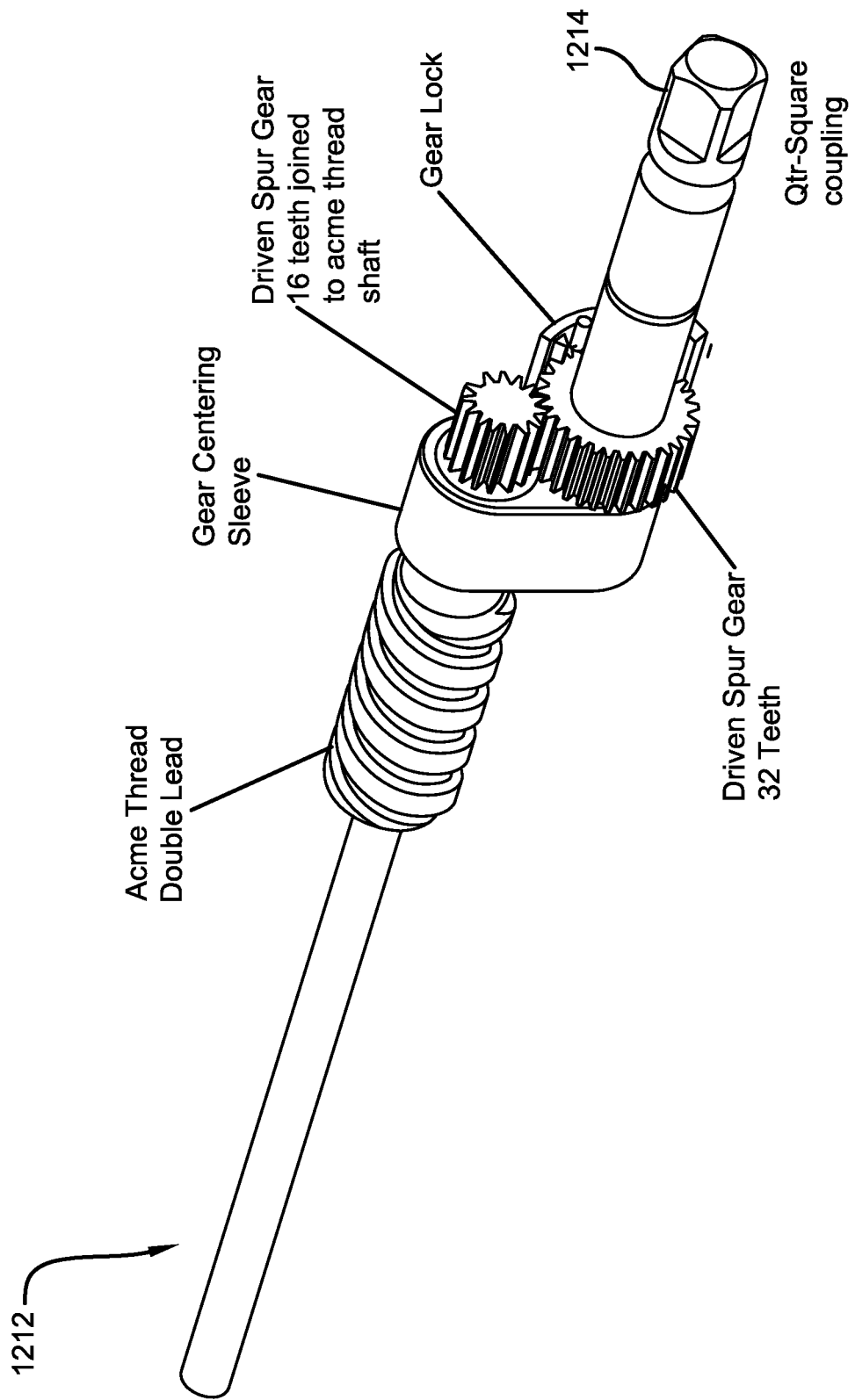
FIG. 88 shows an embodiment of a piston drive assembly in an assembled condition.
Figure 89:
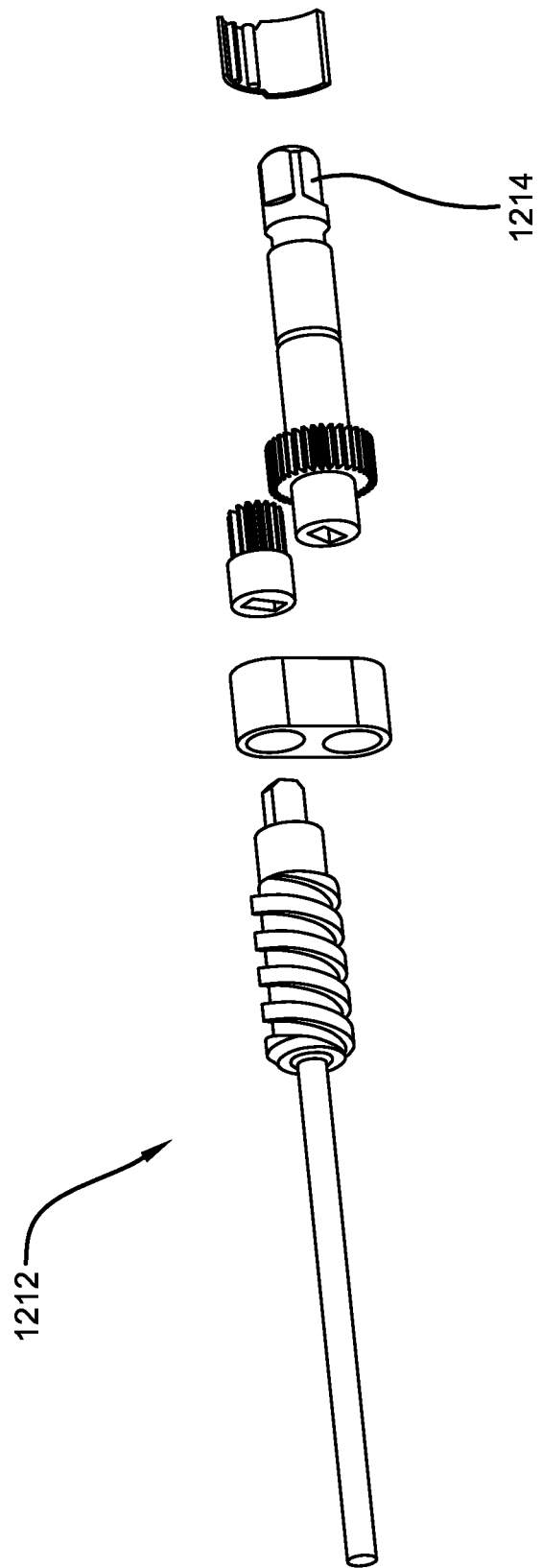
FIG. 89 shows the piston drive assembly of FIG. 88 but in a disassembled condition.

With reference now to FIGS. 19-20, 26, 33, 46-54 and 81-83, impactor 2200 may be used, as disclosed above and illustrated in FIG. 82. The surgeon may use a mallet or other device against contact surface 2204 to move impactor 2200 from position A to position B. This motion may cause the contact surface 2202 of the impactor 2200 (see FIG. 50) to apply additional force to the remover tamp 3000 causing it to extend from position A to position B as shown in FIG. 81. This extension of the tamp 3000 causes the implant 300 to adjust from the deployed condition to the collapsed condition as indicated in FIG. 81. This collapsing of the implant 300 may cause pin 332 to separate as shown in FIGS. 19-20 and described above. The surgeon may use fluoroscopy and the relative positions of pins 332 (now in the form of pin portions 344 and 346) and 350, as described above, to confirm that the implant 300 is unlocked and in the collapsed condition. With the implant 300 now maintained in the collapsed condition, it can then be removed from the vertebral space as shown in FIG. 83. The impactor 2200, remover tamp 3000 and gripping device 3200 may be removed from the inserter 900 in the same way as the previously described impactor, inserter tamp and gripping device.

As described above, the surgeon may use a mallet or similar device to move the impactor 2200 distally to deploy the implant 300 (see FIGS. 67-71) and/or to collapse the implant 300 (see FIGS. 81-83). With reference now to FIGS. 84-89, in other embodiments, in place of (or in addition to) a mallet, the surgeon may use a rotational force converter 1200 that converts a rotational force into a linear force to move the impactor 2200 distally. The rotational force converter 1200 may have a proximal end that receives the rotational force and a distal end that engages the proximal end of the inserter 900 and the proximal end of the impactor 2200.

With reference now to FIGS. 84-87, the distal end of the rotational force converter 1200 may have an engagement cavity 1202 into which both the proximal end of the inserter 900 and the proximal end of the impactor 2200 are received, as shown. The engagement cavity 1202 may have an inside diameter with a generally circular cross-section to match the generally circular cross-section of the proximal end of the inserter 900 and the generally semi-circular cross-section of the proximal end of the impactor 2200. The distal end of the engagement cavity 1202 may have one or more inwardly projecting tabs 1204 that are received in the grooves formed in the proximal end of the inserter 900, as seen best in FIG. 87. The distal end of the engagement cavity 1202 may have one or more inwardly projecting ball plungers 1206 (see FIG. 87) that may be held to the converter 1200 with screws 1208, that engage the outer surface of the inserter 900. The use of tabs 1204 and/or ball plungers 1206 help to provide a secure engagement of the converter 1200 to the inserter 900. It is thus easy for the surgeon to both engage and disengage the converter 1200 and the inserter 900. The engagement cavity 1202 may be open, as shown, so that the surgeon can easily see the engagements and positions of converter 1200, inserter 900 and impactor 2200 at all times.

With reference now to FIGS. 84-89, the rotational force converter 1200 may have a piston 1210 that applies a linear force to the impactor 2200 and a piston drive assembly 1212 that receives a rotational force and converts it to a linear force. In one embodiment, shown, the piston 1210 and piston drive assembly 1212 are positioned within or primarily within the converter 1200 body. While the piston drive assembly 1212 may be of any type chosen with the sound judgment of a person of skill in the art, one embodiment is shown with components labeled in FIG. 88. When the surgeon applies a rotational force to the input shaft 1214, such as with a handle, not shown, the piston drive assembly 1212 converts the rotational force to a linear force that moves the piston 1210 distally to move the impactor 2200 distally to deploy and/or to collapse the implant 300. By rotating the input shaft 1214 in the opposite direction the surgeon causes the piston 1210 to move proximally to remove the force from the impactor 2200. It should be understood that the rotational force converter 1200 is not limited to use with an impactor.

It may be desirable to reduce the medial/lateral profile (width) of the distal end 902 of the inserter 900. This width is shown with reference 970 in FIGS. 62 and 69. As explained above, the inserter tamp 1800 may be used to maintain the implant 300 in the contracted or non-deployed condition (as shown in FIG. 62) and to deploy the implant 300 (as shown in FIG. 69). The inserter width 970 can be reduced with embodiments discussed below.

With reference now to FIGS. 90-93, the surgical instrumentation according to some aspects of the present teaching may include an inserter 1600 having a distal end portion 1602 and a proximal end portion 1604. The outer surface of the proximal end portion 1604 may serve as a handle for the surgeon. The outer surface of the distal end portion 1602 may include markings, not shown, to assist the surgeon in properly positioning the inserter 1600 during surgery. The inserter 1600 may be used to insert and deploy an implant 300 as will be discussed further below.

Figure 90:
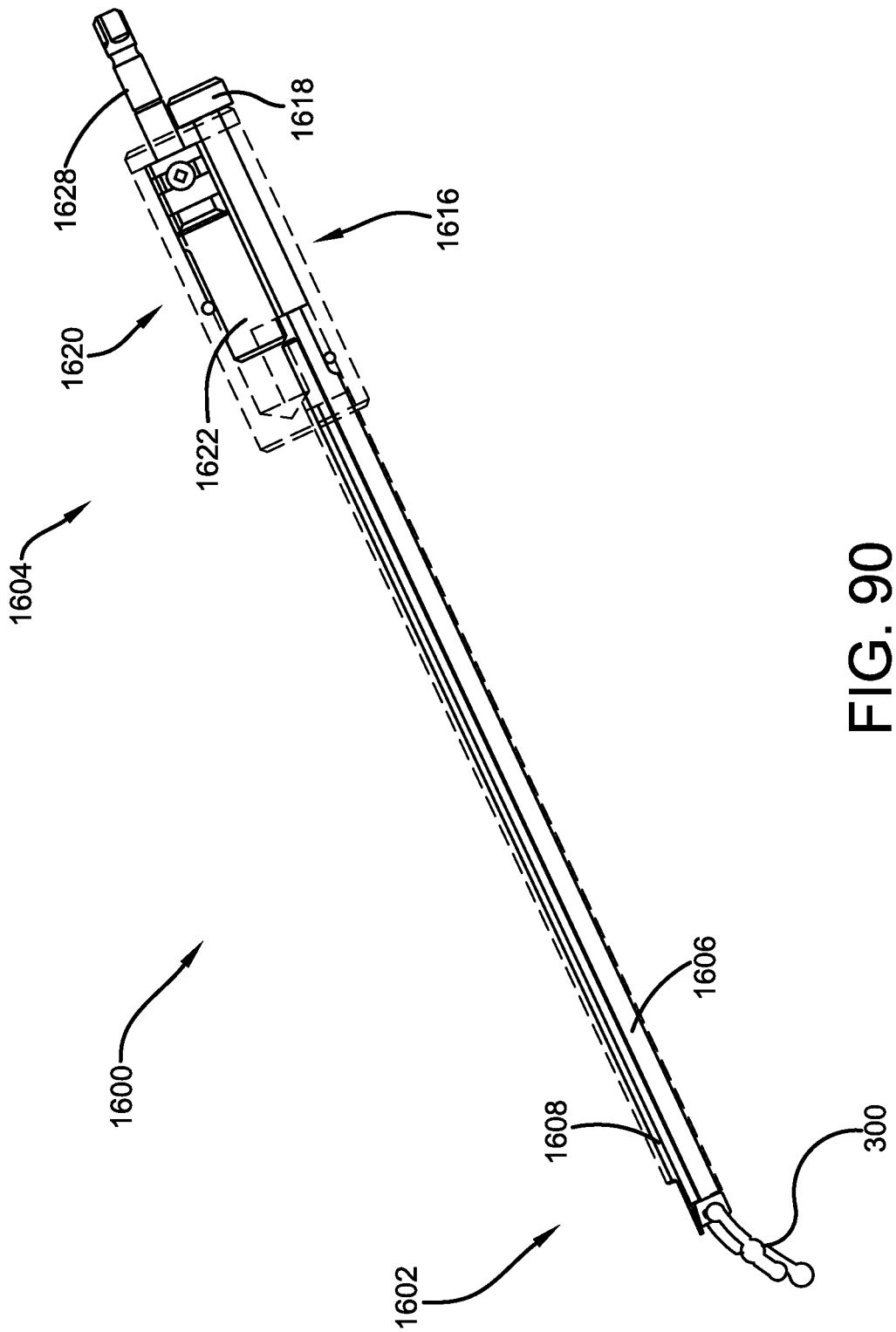
FIG. 90 shows an inserter in a "see-through" view so that internal components can be seen.
Figure 91:
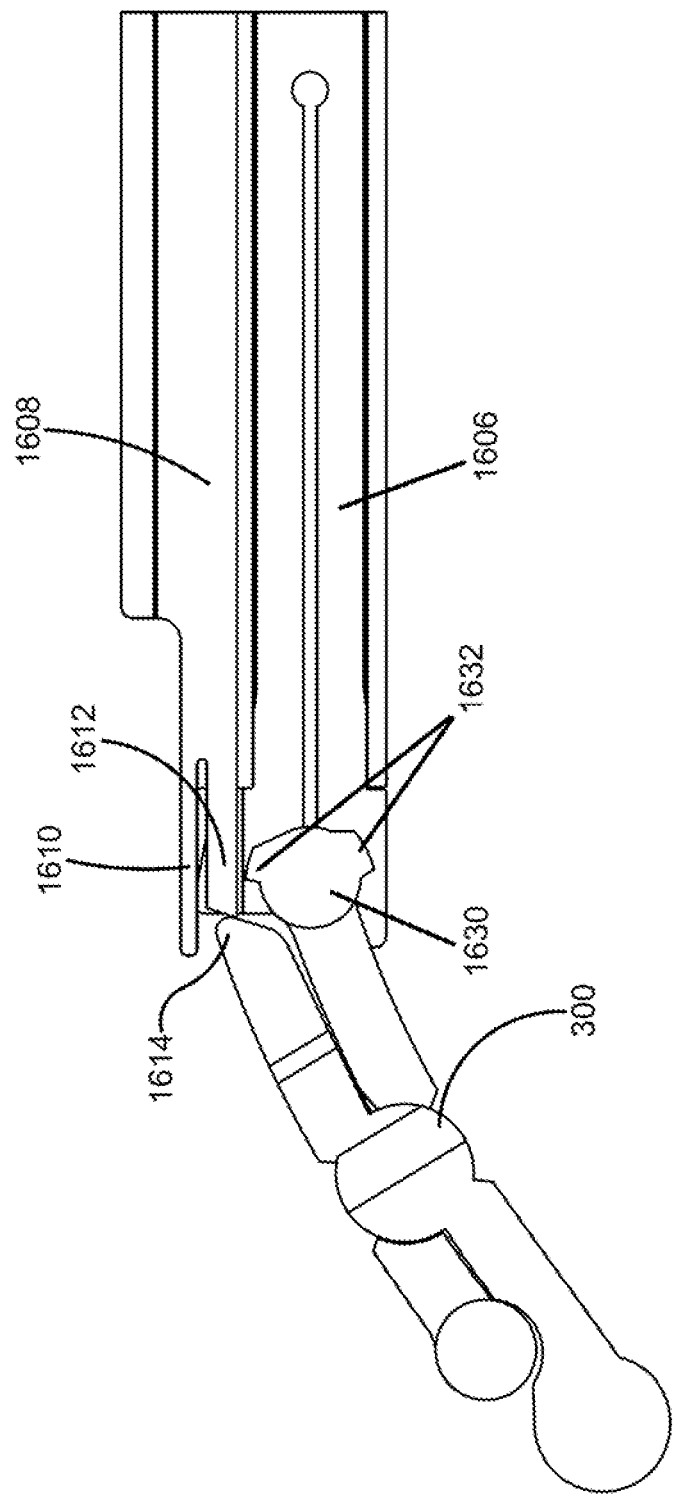
FIG. 91 shows the distal end of the inserter of FIG. 90 but in a sectional view.
Figure 92:
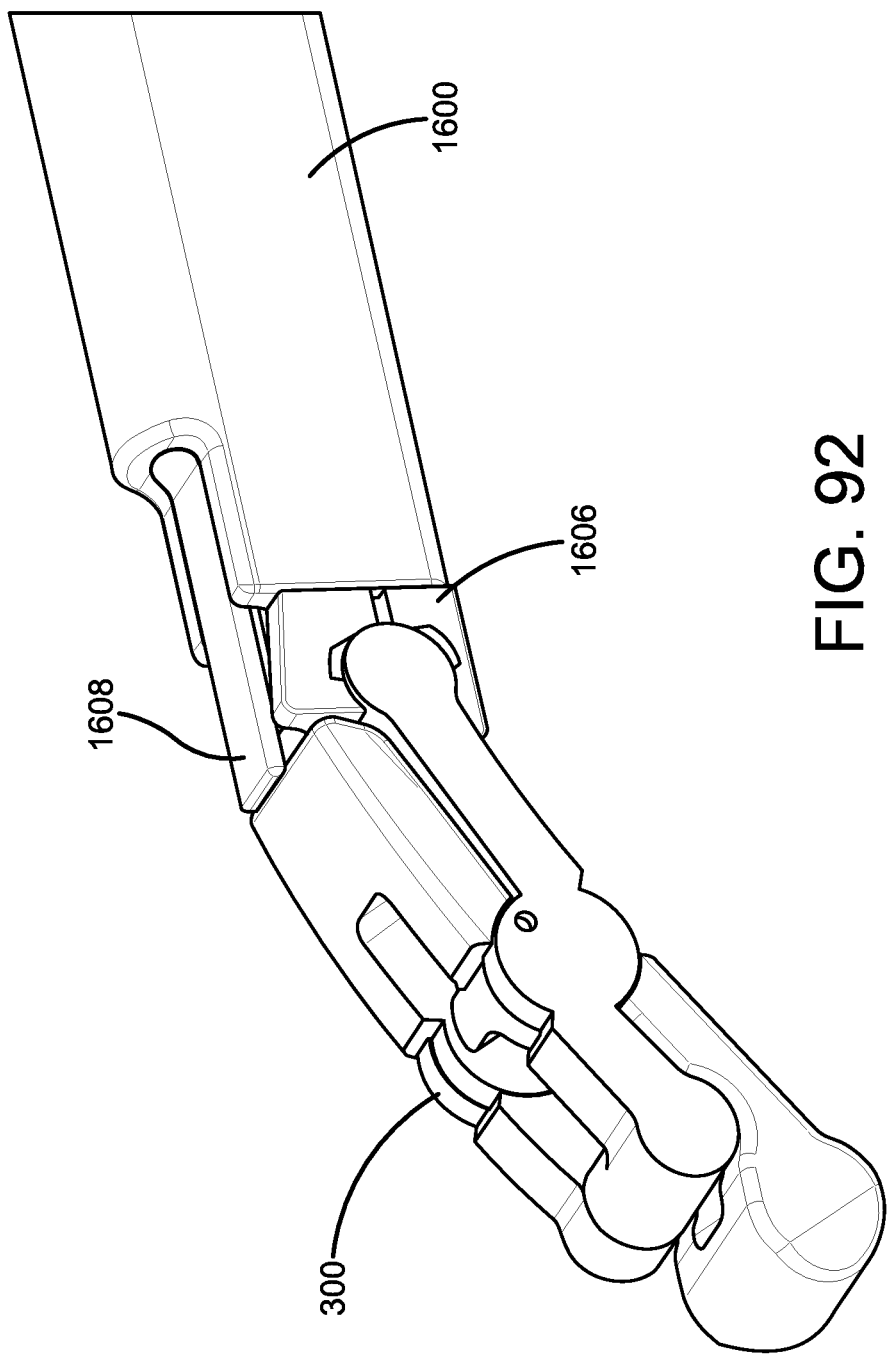
FIG. 92 shows the distal end of the inserter of FIG. 90 but in a perspective view.

With reference now to FIGS. 90-92, the distal end portion 1602 of the inserter 1600 may be a tube having two distinct longitudinally extending internal channels similar to those described above. One channel, the lower one shown in the FIGURES, may hold a gripping device 1606. Gripping device 1606 may operate similarly to previously described gripping device 3200 in holding and releasing implant 300. The other channel, the upper one shown in the FIGURES, may hold a pusher 1608. Pusher 1608 may be an axle that extends longitudinally, as shown, and may have a distal end that engages the implant 300. For the embodiment shown, the distal end of the pusher 1608 has an anti-deployment finger 1610 and a deployment finger 1612, distinct from the anti-deployment finger 1610. The anti-deployment finger 1610 is sized to restrict deployment because implant tip 1614 would contact finger 1610 limiting counterclockwise motion (as shown in FIG. 91) required for deployment. When the pusher 1608 is moved distally, however, deployment finger 1612 is able to push implant tip 1614 past finger 1610 permitting counterclockwise motion and implant deployment.

Figure 93:
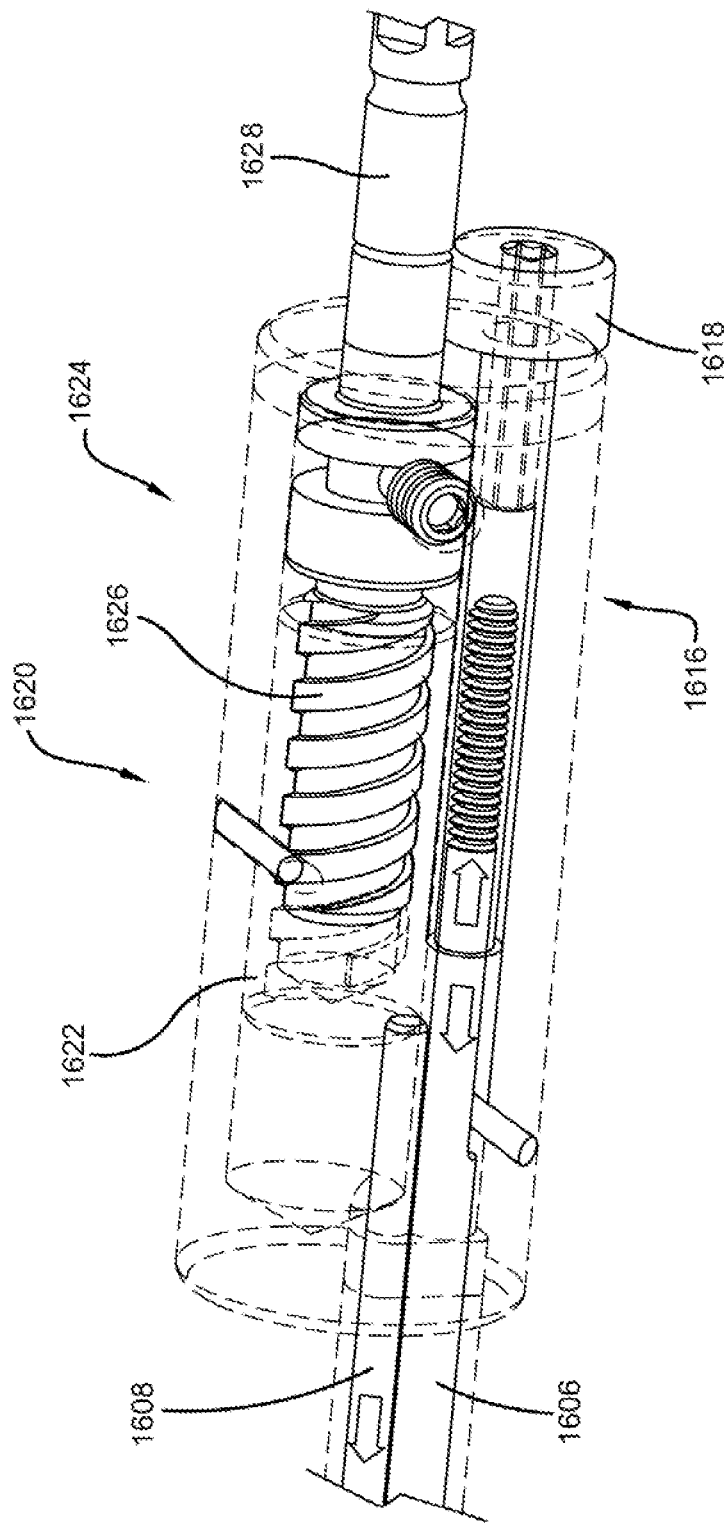
FIG. 93 shows the proximal end of the inserter of FIG. 90 in a "see-through" view.

With reference now to FIGS. 90 and 92-93, the proximal end portion 1604 of the inserter 1600 may have two rotational force converters 1616, 1620. Rotational force converter 1616 may operate similarly to previously described rotational force converter 930. The distal end of converter 930 may receive the threaded proximal end of the gripping device 1606. The proximal end of converter 930 may be attached to knob 1618. When the surgeon rotates knob 1618 in one direction, the converter 930 causes the gripping device 1606 to move proximally, causing the gripping device 1606 to grip the implant 300. When the surgeon rotates the knob 1618 in the opposite direction, the converter 930 causes the gripping device 1606 to move distally, causing the gripping device 1606 to release the implant 300.

With reference now to FIGS. 90-93, rotational force converter 1620 may operate similarly to previously described rotational force converter 1200. Rotational force converter 1620 may have a piston 1622 that applies a linear force to the proximal end of the pusher 1608 and a piston drive assembly 1624 that receives a rotational force and converts it to a linear force. While the piston drive assembly 1624 may be of any type chosen with the sound judgment of a person of skill in the art, in one embodiment it includes an acme threaded shaft 1626 connected to an input shaft 1628. When the surgeon applies a rotational force to the input shaft 1628, such as with a handle, not shown, the piston drive assembly 1624 converts the rotational force to a linear force that moves the piston 1622 distally to move the pusher 1608 distally to deploy the implant 300. By rotating the input shaft 1628 in the opposite direction the surgeon causes the piston 1622 to move proximally to remove the force from the pusher 1608.

With reference now to FIGS. 94-99, the surgical instrumentation according to some aspects of the present teaching may include an inserter 1700 having a distal end portion 1702, a proximal end portion 1704 and a mid-section 1706 between the distal and proximal end portions. The outer surface of the proximal end portion 1704 may serve as a handle for the surgeon. The outer surface of the mid-section 1706 and/or distal end portion 1702 may include markings, not shown, to assist the surgeon in properly positioning the inserter 1700 during surgery. The inserter 1700 may be used to insert and deploy an implant 300 as will be discussed further below.

With reference now to FIGS. 95-99, the mid-section 1706 may have a generally concentric design with a pusher 1708 in the center that is concentric within a longitudinally extending channel 1754 of tube-shaped gripping device 1710 (longitudinally extending channel 1754 may extend from the proximal end to the distal end of the gripping device 1710 and may give the gripping device 1710 a tube shape). The gripping device 1710 may be concentric within a longitudinally extending channel 1756 of a tube-shaped sheath 1712 (longitudinally extending channel 1756 may extend from the proximal end to the distal end of the sheath 1712 and may give the sheath 1712 a tube shape). The sheath 1712 may be concentric within a longitudinally extending channel 1758 of a tube-shaped outer cover 1714 (longitudinally extending channel 1758 may extend from the proximal end to the distal end of the outer cover 1714 and may give the outer cover 1714 a tube shape).

With continuing reference to FIGS. 95-99, the pusher 1708 may be an axle that extends longitudinally, as shown, with a proximal end having an outer surface that is threaded, as shown, for purposes to be discussed below. Attached to the distal end of the pusher 1708 may be an implant engagement finger 1716. The engagement finger 1716 may have first and second portions 1718, 1719. First portion 1718 may be at the proximal end of the engagement finger 1716 and may extend through a groove 1713 formed at the distal end of the gripping device 1710 and through a groove 1715 formed at the distal end of the sheath 1712. The grooves 1713, 1715 may extend longitudinally, as shown. For the embodiment shown, the first portion 1718 extends radially outward through the grooves 1713, 1715. The second portion 1719 of the engagement finger 1716 may extend longitudinally from the first portion 1718 toward the implant 300. For the embodiment shown, the second portion 1719 extends along the groove 1715 in the sheath 1712. Thus, the engagement finger 1716 may not be concentric with pusher 1708. For the embodiment shown, most of the second portion 1719 of the engagement finger 1716 is generally at the same radial position as the sheath 1712. The distal tip 1721 of the engagement finger 1716 may be shaped to contact the implant 300 to deploy the implant. It may, for example, extend radially inward, as shown.

Figure 99:
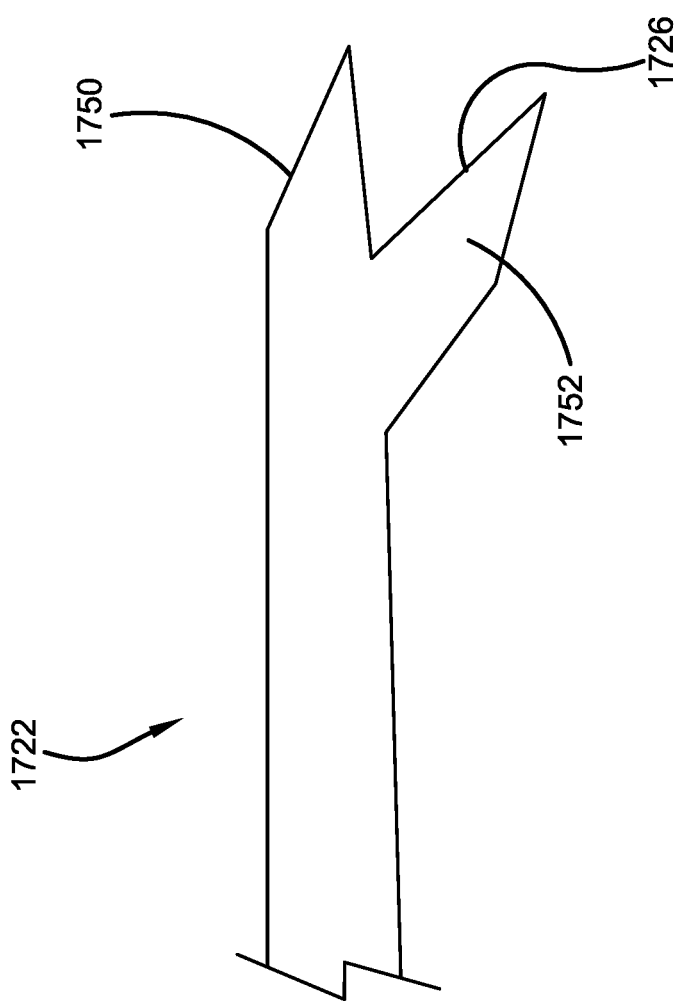
FIG. 99 shows the distal end of an alternate implant engagement finger.
Figure 100:
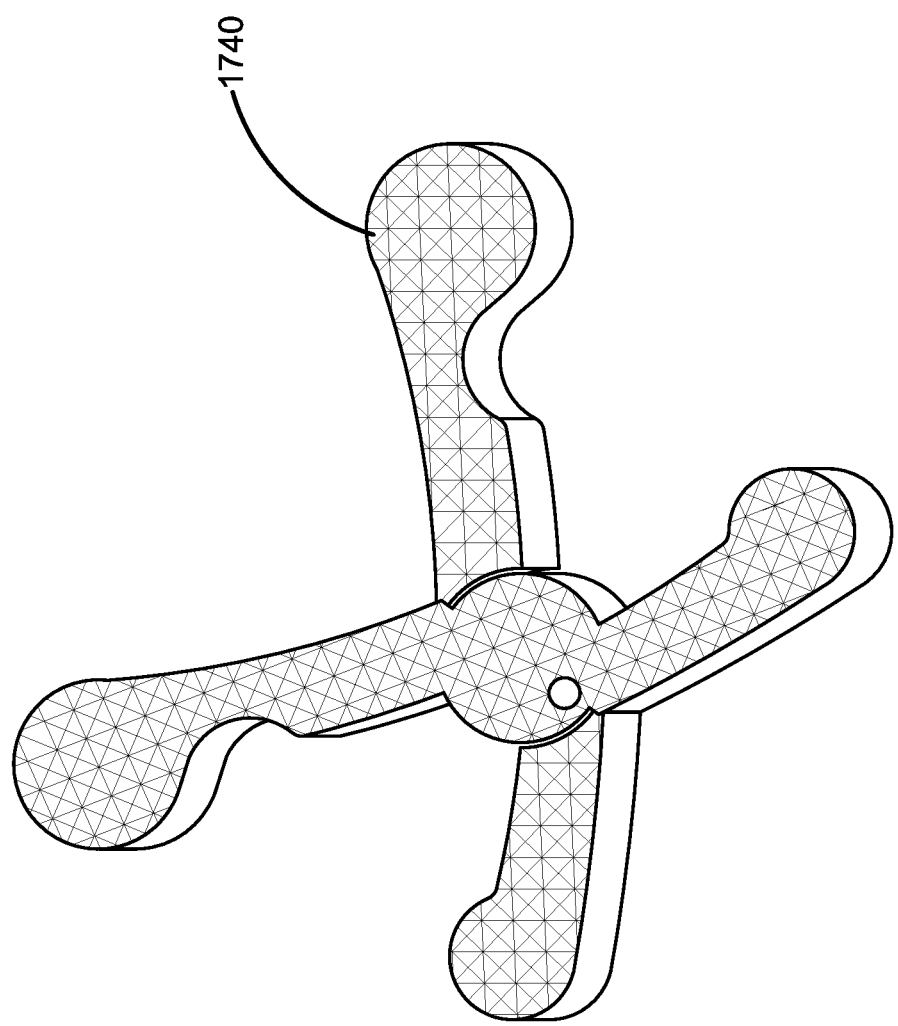
FIG. 100 shows a spinal implant.
Figure 101:
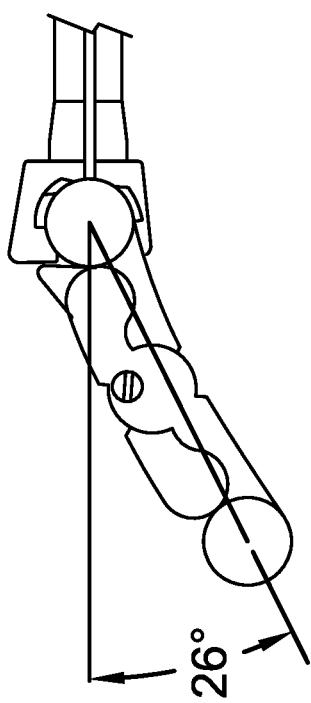
FIG. 101 shows a spinal implant at a 30 degree orientation.
Figure 102:
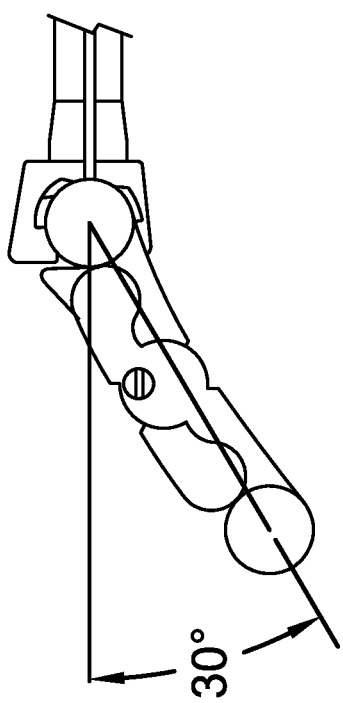
FIG. 102 shows a spinal implant at a 26 degree orientation.

FIG. 99 shows an implant engagement finger 1722 according to another embodiment. In this case, the distal end has a general C-shape or V-shape 1726 having an anti-deployment finger portion 1750 and a deployment finger portion 1752, distinct from the anti-deployment finger portion 1750. This may operate similar to the anti-deployment and deployment fingers 1610, 1612 discussed above. Thus, if a portion of the implant is received between the finger portions 1750, 1752 (such as implant portion 301 shown in FIG. 97) and the pusher 1708 has not been extended sufficiently distally to deploy the implant, the implant cannot be inadvertently deployed because anti-deployment finger portion 1750 prevents it.

With reference now to FIGS. 94-98, the proximal end of the gripping device 1710 may supported to the handle. The distal end of the gripping device 1710 may be used to grip and release the implant 300 similar to other gripping devices described above. The proximal end of the sheath 1712 may have an outer surface that is threaded, as shown, for purposes to be discussed below. The proximal end of the outer cover 1714 may have an outer rim 1724 that is used for purposes to be discussed below. The distal end of the outer cover 1714 may have one or more flaps 1726 that can be used to protect the implant 300 prior to deployment. The one or more flaps 1726 may, for example, be positionable juxtaposed to the implant, as shown.

Figure 94:
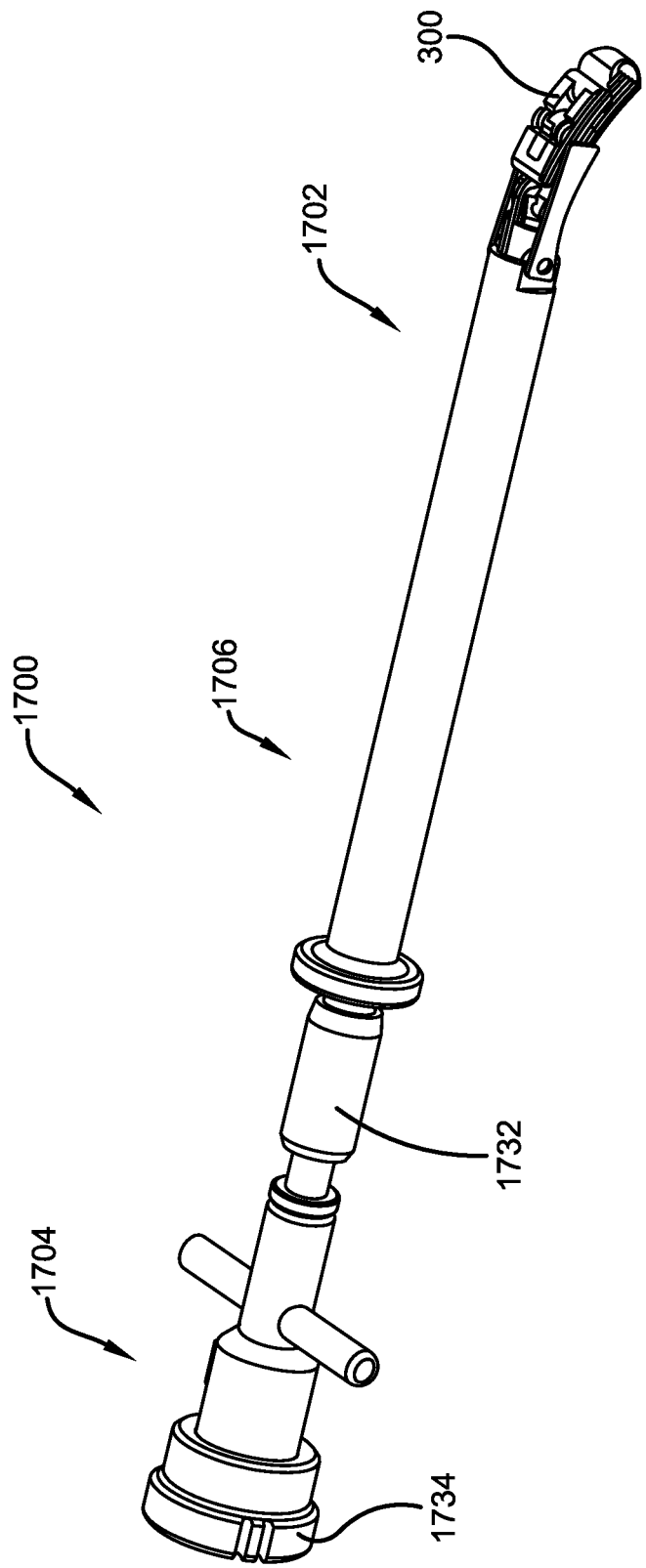
FIG. 94 shows an inserter.
Figure 95:
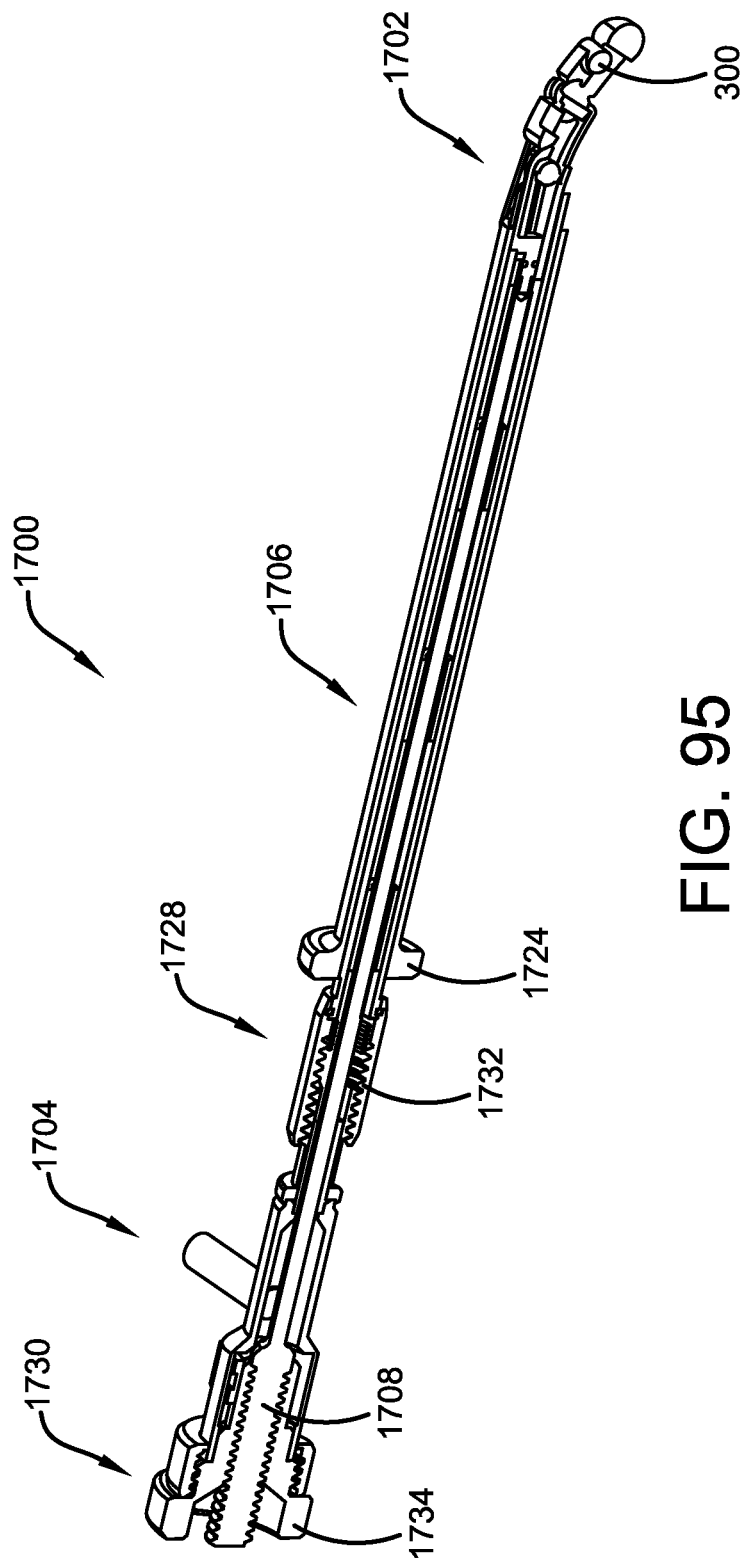
FIG. 95 is a sectional view of the inserter shown in FIG. 94.
Figure 96:
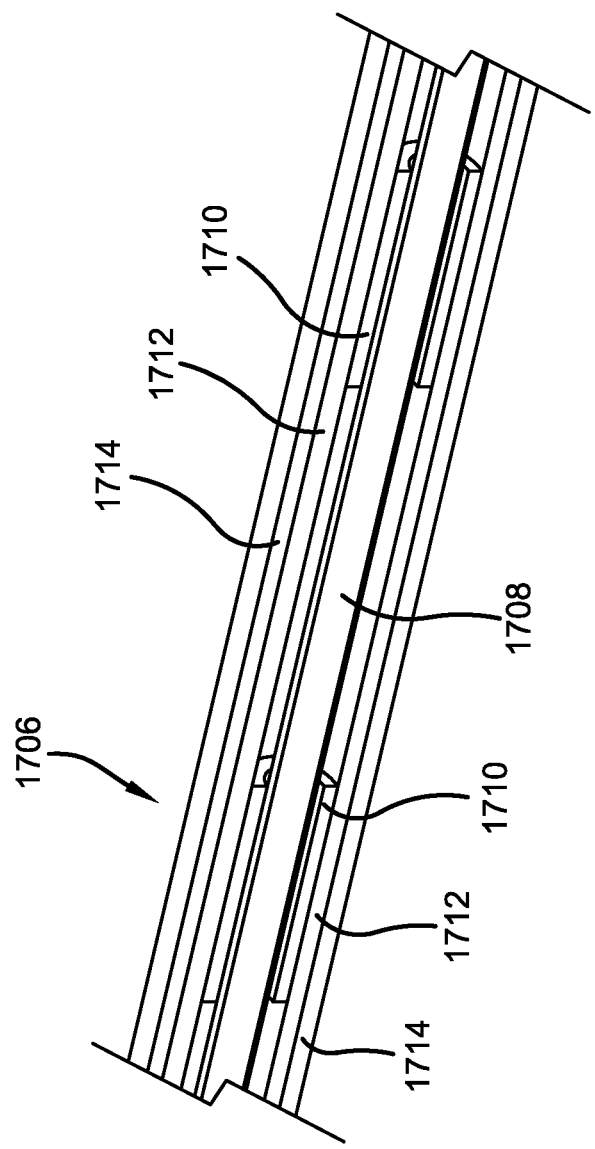
FIG. 96 is a close-up view of a portion of the mid-section of the inserter shown in FIG. 95.

With reference now to FIGS. 94-96, the proximal end portion 1704 of the inserter 1700 may have two rotational force converters 1728, 1730. Rotational force converter 1728 may include a rotatable knob 1732 having internal threads that receive the threads on the sheath 1712. Rotational force converter 1730 may include a rotatable knob 1734 having internal threads that receive/engage the threads on the pusher 1708.

Figure 97:
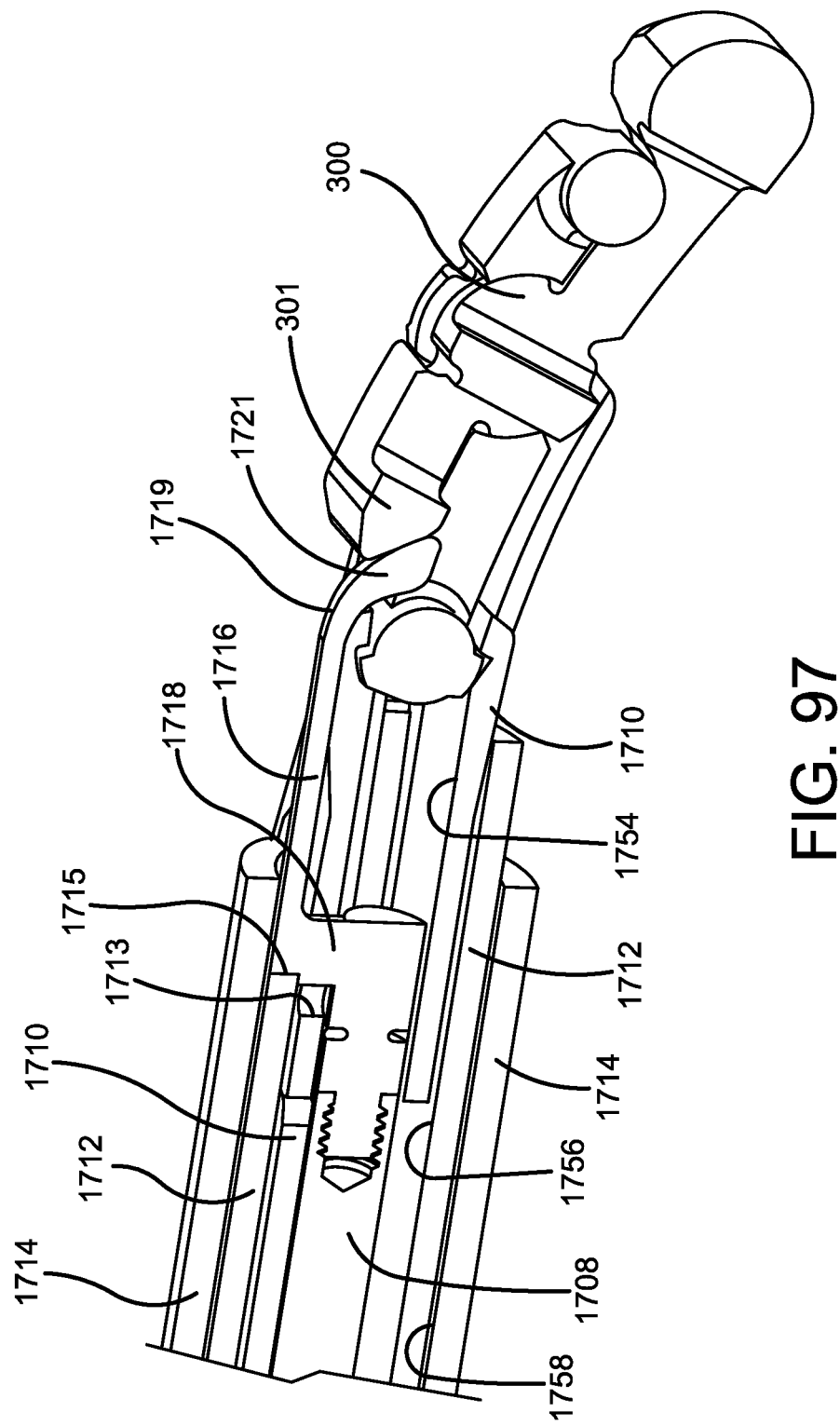
FIG. 97 is a close-up view of the distal end of the inserter shown in FIG. 95.
Figure 98:
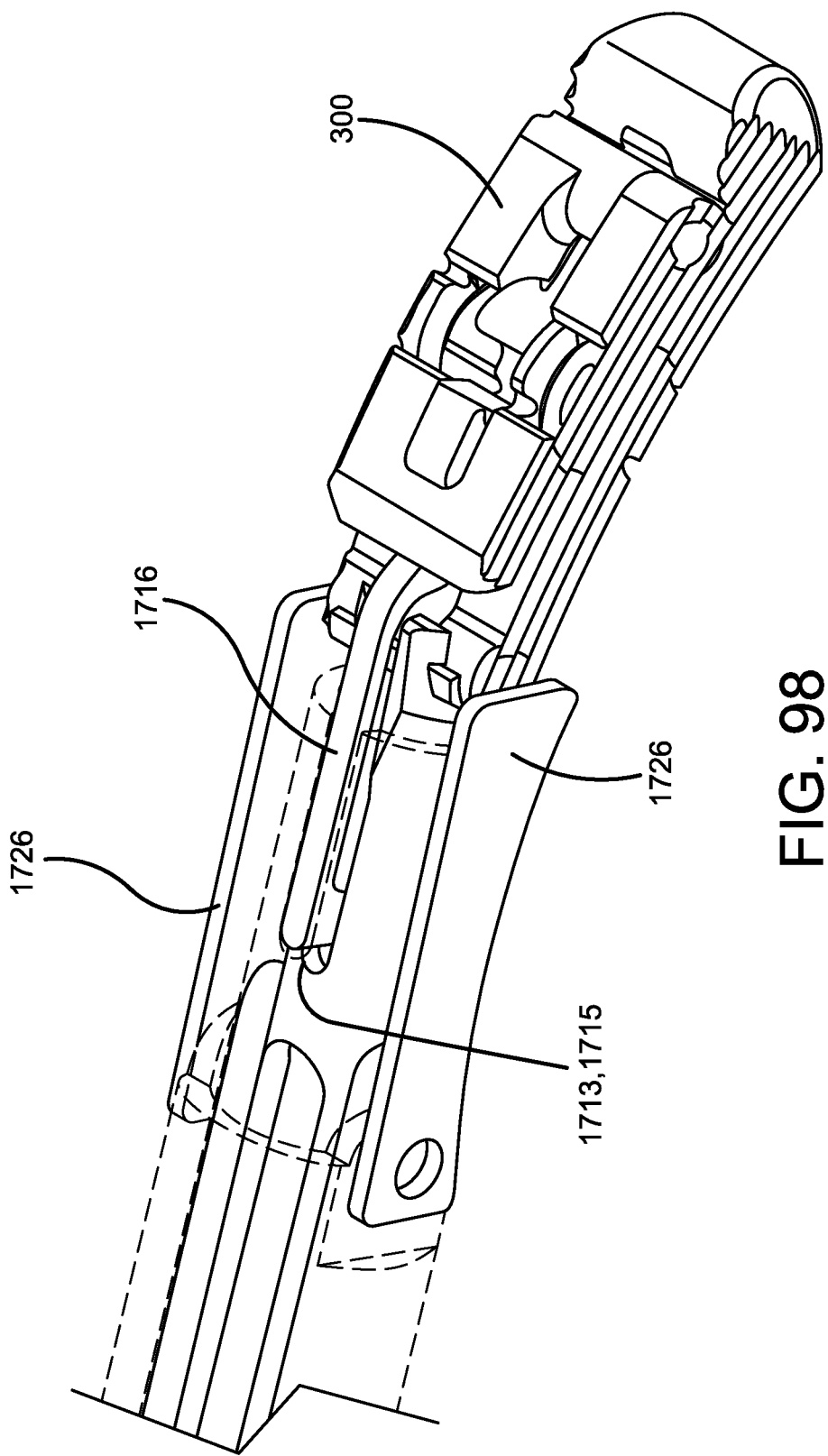
FIG. 98 is a view similar to that shown in FIG. 27 but not in a sectional view.

With reference now to FIGS. 94-99, to use the inserter 1700 the surgeon may slide the outer cover proximally (rim 1724 may be used for this motion if desired) to move the flaps 1726 away from the distal end of the gripping device 1710. Similarly, the surgeon may rotate knobs 1732 and 1734 to move sheath 1712 and pusher 1708, respectively, proximally away from the distal end of the gripping device 1710. The implant 300 may then be attached to the distal end of the gripping device 1710 as with other gripping devices explained above. The surgeon may then rotate knob 1732 to move the sheath 1712 distally to cause the gripping device 1710 to grip the implant 300. Knob 1734 may then be rotated to move pusher 1708 distally until engagement finger 1716 is positioned near to the implant 300 as shown in FIGS. 97 and 98. Next, the surgeon may slide the outer cover distally to move the flaps 1726 on either side of the implant 300 to protect it. The implant 300 may then be inserted into the patient.

With continuing reference to FIGS. 94-99, once implant 300 is positioned near the vertebral space, the surgeon may slide the outer cover proximally (rim 1724 may be used for this motion if desired) to move the flaps 1726 away from the implant 300. The implant 300 can then be positioned into the vertebral space. Next, knob 1734 may be rotated to move pusher 1708 distally until engagement finger 1716 deploys the implant 300. Knob 1734 may then be rotated to move pusher 1708 proximally to move engagement finger 1716 away from the implant 300. Finally, the surgeon may rotate knob 1732 to move the sheath 1712 proximally to cause the gripping device 1710 to release the implant 300. The inserter can now be removed from the patient.

With reference now to FIGS. 91 and 100-102, it should be noted that the posts of the implant can be simply modified to enable the implant to be used with anterior lumbar interbody fusion and with lateral interbody fusion. These use variations can be achieved by changing the post that is attached to the inserter and/or the angle of orientation of the nondeployed implant relative to the longitudinal axis of the shaft of the inserter. Compare, for example, the implant post 1740 shown in FIG. 100 having a circular cross-section to the post 1630 shown in FIG. 91 that has a pair of lugs 1632. Also, compare the 30 degree orientation shown in FIG. 101 to the 26 degree orientation shown in FIG. 102.

It should be understood that the implant can be inserted along any circumferential axis of the vertebral interspace. The drawings herein depict placement via a posterolateral approach. This includes customary, clinically accepted approaches for posterior lumbar interbody fusion (PLIF), transforaminal lumbar interbody fusion (TLIF) and extraforaminal lumbar interbody fusion (ELIF). The implant is also envisioned to be placed via lateral approaches such as lateral interbody fusion (LIF), direct lateral interbody fusion (DLIF), and anterolateral or oblique approaches (OLIF). It can also be placed as an anterior lumbar interbody fusion (ALIF). All that is required to achieve any of these approaches is a change in the orientation of the non-deployed implant relative to the long axis of the shaft of the inserter. This merely requires a modification of the post of the implant attached to the inserter, as originally envisioned with a sprocketed or clocked teeth in the post attached to the inserter to change the angle of insertion relative to the long axis of the inserter as to the surgeon's preference. In the case of anterior or anterolateral approaches, the inserter may be attached to modified anterior implant posts to allow implant deployment with a deployment force directed from the anterior posts to the posterior posts, reversed from the previously described posterior insertion with deployment forces directed from posterior to anterior.

Figure 103:
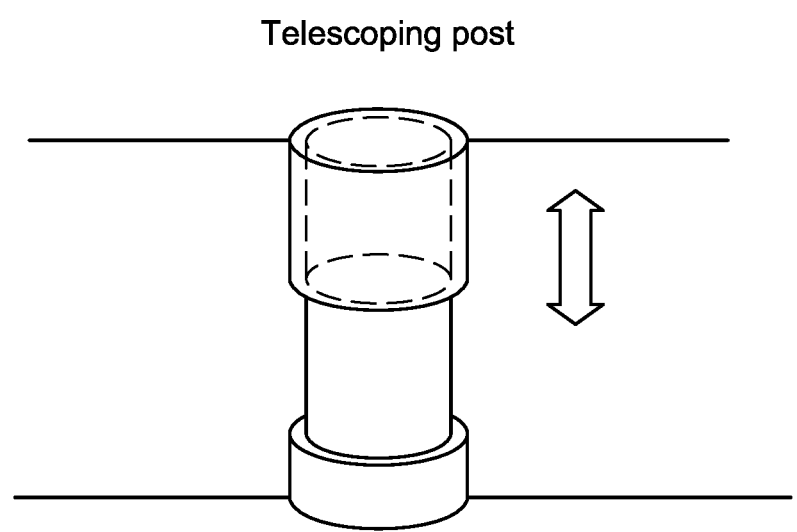
FIG. 103 illustrates a telescoping implant post.

The implants disclosed previously can be expanded horizontally; in the "X" and "Y" axes. In other embodiments, the implant may also expand vertically; in height or the "Z" axis. This may be accomplished by using a cam or ramp effect as the implant's first member pivots with respect to the second member between the non-deployed condition and the deployed condition. As described above and shown in FIG. 10, contact surfaces 318 and 322 are planar with generally circular shapes. In other embodiments, these contact surfaces may be angled relative to each other and/or have curved surfaces. This would create cam surfaces or ramp surfaces to elevate one member relative to the other member. In some embodiments, at maximum horizontal expansion the implant would also attain maximum height expansion. The contact surfaces may also have shapes other than circular. The final position may be held by the locking mechanism, or similar construct, as previously described. To achieve the height expansion, the implant posts 314, 314 may have a telescoping design such as shown in FIG. 103. In some embodiments, the opposite ends of member 308 may also have telescoping posts. The amount of height expansion may be limited by the maximum height expansion being self-locking to each individual post. As a non-limiting example, an implant labeled at a 10 mm height may have an additional Z-axis height expansion of 1 mm, or 1.5 mm or 2 mm per the design specifications for that specific implant. Thus, a 10 mm implant with a 2 mm height expansion would have a maximum static height of 12 mm at full deployment. The ramp surfaces can alternatively be described as a "helical flange." This could be either a "single helical flange" involving only one set of limbs in the same plane or a "double helical flange" involving two sets of limbs in two parallel planes (the top and bottom limbs for example). The calculation for the height changes may be B=A+"self-distracting convex taper" for the basic implant. For the "single helical flange" [SHF] and double helical flange" [DHF] versions the calculations would be as follows, respectively: SHF Height=B+hf; and DHF Height=B+2hf. The helical flanges in a double helical flange configuration could be asymmetrical, i.e., unequal, to assist with achieving various angulation values for lordosis (lordotic taper) of the implant.

Figure 104:
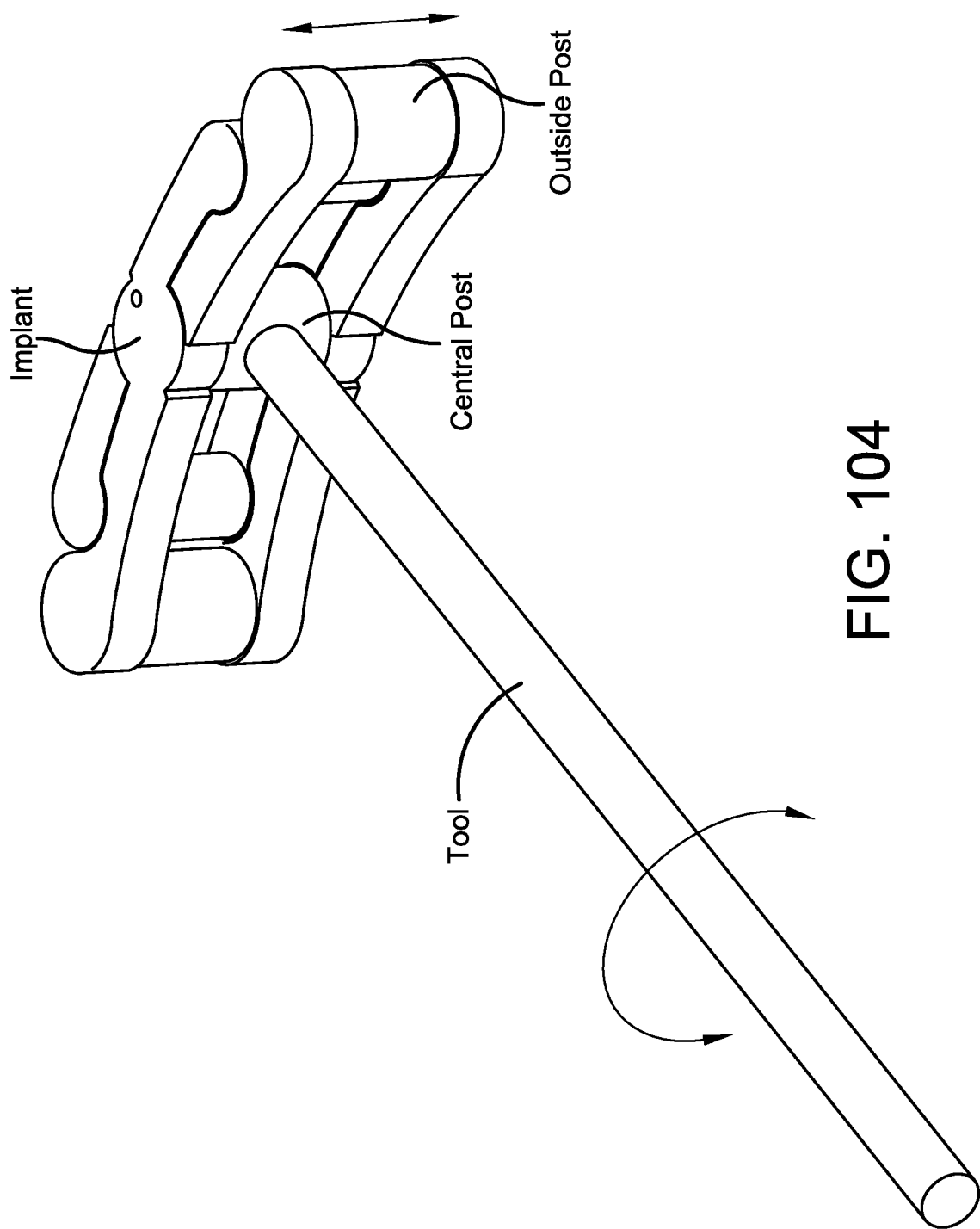
FIG. 104 illustrates a height adjustable implant.

The implants disclosed previously have a static lordosis. In other embodiments, the lordosis may be adjusted to any desired lordosis merely by changing the height of the anterior posts relative to the posterior posts. This allows for an extremely wide range of lordotic taper in the implant. In yet other embodiments, the implant may have dynamic lordosis features. This may be accomplished by the use of telescoping posts in the anterior portion and hinged posts in the posterior portion of the implant. There may be an axis of rotation when viewed in the lateral projection that shows that the posterior hinged posts would serve as the axis of rotation and the anterior posts, which may be be curved, would allow telescoping height increases to facilitate a change in the lordotic angle of the implant. The anterior posts in this depiction of the implant may be self-locking once the optimum lordosis would be achieved, per the surgeon's preferences and limited by the design max specifications of the implant. In yet other embodiments, the central portion of the implant may be formed of a telescoping post and may be height adjusted using height adjuster tool as illustrated in FIG. 104.

In other embodiments, the implant may be surface prepared for optimized in-growth of bone, either by manufactured surface preparation and/or material application. It may be made porous throughout as allowed and restricted only by the minimum structural requirements of the device per FDA and/or ASTM requirements.

In the patent claims that follow, it should be understood that any component referred to as being "associated" is not being claimed positively but rather indicates the environment in which the claimed invention is used. Thus, for two non-limiting examples, if a patent claim includes "surgical instrumentation for use with an associated vertebral space" or "surgical instrumentation for use with an associated spinal implant" then Applicant's intent is that infringement does not require a vertebral space or a spinal implant. Rather, infringement only requires the surgical instrumentation used with a vertebral space or spinal implant.

I claim:

1. Surgical instrumentation for use with an associated intradiscal space comprising a first vertebral body having a first endplate and a second vertebral body adjacent the first vertebral body having a second endplate, the surgical instrumentation comprising:
   an implant comprising:
      1) a first portion;
      2) a second portion that is pivotal with respect to the first portion;
      3) wherein the first and second portions define first and second contact surfaces adapted to contact the first and second endplates, respectively; and
      4) wherein the implant is deployable by pivoting the second portion with respect to the first portion;
   an inserter adapted to insert the implant into the associated intradiscal space when not deployed and to deploy the implant within the associated intradiscal space, the inserter comprising:
      1) a handle;
      2) a sheath including:
         (a) a proximal end supported to the handle;
         (b) a distal end, opposite the proximal end;
         (c) a longitudinally extending channel that extends from the proximal end to the distal end and gives the sheath a tube shape; and
         (d) a groove formed at the distal end that communicates with the longitudinally extending channel;
      3) a gripping device including:
         (a) a proximal end supported to the handle;
         (b) a distal end, opposite the proximal end, adapted to grip and release the first portion of the implant;
         (c) a longitudinally extending channel that extends from the proximal end to the distal end and gives the gripping device a tube shape;

(d) a groove formed at the distal end that communicates with the longitudinally extending channel; and
(e) wherein the gripping device is positioned within the longitudinally extending channel of the sheath;
4) a pusher including:
(a) a proximal end supported to the handle;
(b) a distal end, opposite the proximal end;
(c) an implant engagement finger supported to the distal end;
(d) wherein the pusher is positioned within the longitudinally extending channel of the gripping device; and
(e) wherein the implant engagement finger includes:
(i) a first portion that extends through the groove in the gripping device and into the groove in the sheath; and
(ii) a second portion that extends along the groove in the sheath and is adapted to contact the implant;
wherein:
1) the sheath is:
(a) operable to be moved distally to cause the gripping device to grip the first portion of the implant; and
(b) operable to be moved proximally to cause the gripping device to release the first portion of the implant; and
2) the pusher is:
(a) operable to be moved proximally away from the implant; and
(b) operable to be moved distally to cause the implant engagement finger to engage the second portion of the implant to deploy the implant when the gripping device grips the first portion of the implant.

2. The surgical instrumentation of claim 1 wherein:
the second portion of the implant engagement finger has a distal end that is adapted to contact the implant;
the distal end is C-shaped or V-shaped having an anti-deployment finger portion and a deployment finger portion; and
the anti-deployment finger portion is adapted to prevent the implant from deploying until the pusher is moved proximally away from the implant.

3. The surgical instrumentation of claim 1 further comprising:
an outer cover including:
1) a proximal end;
2) a distal end, opposite the proximal end;
3) a longitudinally extending channel that extends from the proximal end to the distal end and gives the outer cover a tube shape; and
4) a first flap that extends distally from the distal end of the outer cover;
wherein the sheath is positioned within the longitudinally extending channel of the outer cover; and,
wherein the outer cover is:
1) operable to be moved proximally away from the implant; and
2) operable to be moved distally to cause the first flap to be juxtaposed to the implant to thereby protect the implant.

4. The surgical instrumentation of claim 3 wherein:
the outer cover has a rim on the proximal end adapted to be used by an associated surgeon to move the outer cover proximally and distally with respect to the sheath;
the implant has a first side and a second side opposite the first side;
the outer cover has a second flap that extends distally from the distal end of the outer cover;
the outer cover is operable to be moved distally to cause:
1) the first flap to be juxtaposed to the first side of the implant to thereby protect the first side of the implant; and
2) the second flap to be juxtaposed to the second side of the implant to thereby protect the second side of the implant.

5. The surgical instrumentation of claim 1 wherein:
a pusher rotational force converter:
1) is supported to the handle;
2) is operable to convert a first pusher rotational force input into a first pusher output that moves the pusher distally; and
3) is operable to convert a second pusher rotational force input into a second pusher output that moves the pusher proximally.

6. The surgical instrumentation of claim 1 wherein:
a sheath rotational force converter:
1) is supported to the handle;
2) is operable to convert a first sheath rotational force input into a first sheath output that moves the sheath distally; and
3) is operable to convert a second sheath rotational force input into a second sheath output that moves the sheath proximally.

7. An inserter for use with:
an associated intradiscal space comprising a first vertebral body having a first endplate and a second vertebral body adjacent the first vertebral body having a second endplate; and,
an associated implant comprising:
1) a first portion;
2) a second portion that is pivotal with respect to the first portion;
3) wherein the first and second portions define first and second contact surfaces adapted to contact the first and second endplates, respectively; and
4) wherein the associated implant is deployable by pivoting the second portion with respect to the first portion;
the inserter being adapted to insert the associated implant into the associated intradiscal space when not deployed and to deploy the associated implant within the associated intradiscal space, the inserter comprising:
1) a handle;
2) a sheath including:
(a) a proximal end supported to the handle;
(b) a distal end, opposite the proximal end;
(c) a longitudinally extending channel that extends from the proximal end to the distal end and gives the sheath a tube shape; and
(d) a groove formed at the distal end that communicates with the longitudinally extending channel;
3) a gripping device including:
(a) a proximal end supported to the handle;
(b) a distal end, opposite the proximal end, adapted to grip and release the first portion of the associated implant;

(c) a longitudinally extending channel that extends from the proximal end to the distal end and gives the gripping device a tube shape;
(d) a groove formed at the distal end that communicates with the longitudinally extending channel; and
(e) wherein the gripping device is positioned within the longitudinally extending channel of the sheath;
4) a pusher including:
(a) a proximal end supported to the handle;
(b) a distal end, opposite the proximal end;
(c) an implant engagement finger supported to the distal end;
(d) wherein the pusher is positioned within the longitudinally extending channel of the gripping device; and
(e) wherein the implant engagement finger includes:
(i) a first portion that extends through the groove in the gripping device and into the groove in the sheath; and
(ii) a second portion that extends along the groove in the sheath and is adapted to contact the associated implant;
wherein:
1) the sheath is:
(a) operable to be moved distally to cause the gripping device to grip the first portion of the associated implant; and
(b) operable to be moved proximally to cause the gripping device to release the first portion of the associated implant; and
2) the pusher is:
(a) operable to be moved proximally away from the associated implant; and
(b) operable to be moved distally to cause the implant engagement finger to engage the second portion of the associated implant to deploy the associated implant when the gripping device grips the first portion of the associated implant.

8. The inserter of claim 7 further comprising:
an outer cover including:
1) a proximal end;
2) a distal end, opposite the proximal end;
3) a longitudinally extending channel that extends from the proximal end to the distal end and gives the outer cover a tube shape; and
4) a first flap that extends distally from the distal end of the outer cover;
wherein the sheath is positioned within the longitudinally extending channel of the outer cover; and,
wherein the outer cover is:
1) operable to be moved proximally away from the associated implant; and
2) operable to be moved distally to cause the first flap to be juxtaposed to the associated implant to thereby protect the associated implant.

9. The inserter of claim 8 wherein:
the outer cover has a rim on the proximal end adapted to be used by an associated surgeon to move the outer cover proximally and distally with respect to the sheath;
the associated implant has a first side and a second side opposite the first side;
the outer cover has a second flap that extends distally from the distal end of the outer cover;
the outer cover is operable to be moved distally to cause:
1) the first flap to be juxtaposed to the first side of the associated implant to thereby protect the first side of the associated implant; and
2) the second flap to be juxtaposed to the second side of the associated implant to thereby protect the second side of the associated implant.

10. The inserter of claim 7 wherein:
a pusher rotational force converter:
1) is supported to the handle;
2) is operable to convert a first pusher rotational force input into a first pusher output that moves the pusher distally; and
3) is operable to convert a second pusher rotational force input into a second pusher output that moves the pusher proximally.

11. The inserter of claim 10 wherein:
the proximal end of the pusher has threads;
the pusher rotational force converter comprises a knob having threads that engage the threads on the pusher;
rotating the knob in a first direction causes the pusher to move distally; and
rotating the knob in a second direction, opposite the first direction, causes the pusher to move proximally.

12. The inserter of claim 7 wherein:
a sheath rotational force converter:
1) is supported to the handle;
2) is operable to convert a first sheath rotational force input into a first sheath output that moves the sheath distally; and
3) is operable to convert a second sheath rotational force input into a second sheath output that moves the sheath proximally.

13. The inserter of claim 12 wherein:
the proximal end of the sheath has threads;
the sheath rotational force converter comprises a knob having threads that engage the threads on the sheath;
rotating the knob in a first direction causes the sheath to move distally; and
rotating the knob in a second direction, opposite the first direction, causes the sheath to move proximally.

14. The inserter of claim 7 wherein:
the second portion of the implant engagement finger has a distal end that is adapted to contact the associated implant;
the distal end is C-shaped or V-shaped having an anti-deployment finger portion and a deployment finger portion; and
the anti-deployment finger portion is adapted to prevent the associated implant from deploying until the pusher is moved proximally away from the associated implant.

* * * * *